US008697255B2

(12) United States Patent
Langer et al.

(10) Patent No.: US 8,697,255 B2
(45) Date of Patent: Apr. 15, 2014

(54) ORGANIC LIGHT-EMITTING DIODES COMPRISING AT LEAST ONE DISILYL COMPOUND SELECTED FROM DISILYLCARBAZOLES, DISILYLDIBENZOFURANS, DISILYLDIBENZOTHIOPHENES, DISILYLDIBENZOPHOLES, DISILYLDIBENZOTHIOPHENE S-OXIDES AND DISILYLDIBENZOTHIOPHENE S,S-DIOXIDES

(75) Inventors: Nicolle Langer, Heppenheim (DE); Klaus Kahle, Ludwigshafen (DE); Christian Lennartz, Schifferstadt (DE); Oliver Molt, Hirschberg (DE); Evelyn Fuchs, Mannheim (DE); Jens Rudolph, Worms (DE); Christian Schildknecht, Mannheim (DE); Soichi Watanabe, Mannheim (DE); Gerhard Wagenblast, Wachenheim (DE)

(73) Assignee: BASF SE, Ludwigshafen (DE)

( * ) Notice: Subject to any disclaimer, the term of this patent is extended or adjusted under 35 U.S.C. 154(b) by 141 days.

(21) Appl. No.: 12/667,765

(22) PCT Filed: Jun. 26, 2008

(86) PCT No.: PCT/EP2008/058207
§ 371 (c)(1),
(2), (4) Date: Oct. 26, 2010

(87) PCT Pub. No.: WO2009/003919
PCT Pub. Date: Jan. 8, 2009

(65) Prior Publication Data
US 2011/0031477 A1 Feb. 10, 2011

(30) Foreign Application Priority Data

Jul. 5, 2007 (EP) .................................... 07111824
Mar. 26, 2008 (EP) .................................... 08153306

(51) Int. Cl.
*H01L 51/54* (2006.01)
(52) U.S. Cl.
USPC ........... 428/690; 428/917; 313/504; 313/505; 313/506; 257/40; 257/E51.05; 257/E51.026; 257/E51.032; 546/18; 546/79; 546/81; 546/101; 548/304.4; 548/418; 548/440
(58) Field of Classification Search
USPC ................. 428/690, 917; 313/504, 505, 506; 257/40, E51.05, E51.026, E51.032; 546/18, 79, 81, 101; 548/304.4, 418, 548/440
See application file for complete search history.

(56) References Cited

U.S. PATENT DOCUMENTS

| 6,464,898 | B1* | 10/2002 | Tomoike et al. ......... 252/301.35 |
| 2001/0015432 | A1 | 8/2001 | Igarashi |
| 2001/0019782 | A1 | 9/2001 | Igarashi et al. |
| 2002/0024293 | A1 | 2/2002 | Igarashi et al. |
| 2002/0048689 | A1 | 4/2002 | Igarashi et al. |
| 2002/0055014 | A1 | 5/2002 | Okada et al. |
| 2002/0094453 | A1 | 7/2002 | Takiguchi et al. |
| 2005/0238919 | A1 | 10/2005 | Ogasawara |
| 2007/0224446 | A1* | 9/2007 | Nakano et al. ................ 428/690 |
| 2007/0262704 | A1* | 11/2007 | Tsai et al. ...................... 313/503 |
| 2008/0199731 | A1* | 8/2008 | Vogler et al. .................. 428/704 |
| 2008/0220287 | A1 | 9/2008 | Dotz et al. |
| 2008/0269485 | A1 | 10/2008 | Moonen et al. |
| 2009/0054657 | A1 | 2/2009 | Molt et al. |
| 2009/0096367 | A1 | 4/2009 | Fuchs et al. |
| 2009/0278119 | A1 | 11/2009 | Schildknecht et al. |

FOREIGN PATENT DOCUMENTS

| EP | 1 191 612 | 3/2002 |
| EP | 1 191 613 | 3/2002 |
| EP | 1 211 257 | 6/2002 |
| JP | 2003 133075 | 5/2003 |
| JP | 2004 200104 | 7/2004 |
| JP | 2004 253298 | 9/2004 |
| WO | 00 70655 | 11/2000 |
| WO | 01 41512 | 6/2001 |
| WO | 02 02714 | 1/2002 |
| WO | 02 15645 | 2/2002 |
| WO | 02 060910 | 8/2002 |
| WO | 2005 019373 | 3/2005 |
| WO | 2005 113704 | 12/2005 |
| WO | 2006 056418 | 6/2006 |

(Continued)

OTHER PUBLICATIONS

U.S. Appl. No. 13/143,651, filed Jul. 7, 2011, Langer, et al.

(Continued)

*Primary Examiner* — Gregory Clark
(74) *Attorney, Agent, or Firm* — Oblon, Spivak, McClelland, Maier & Neustadt, L.L.P.

(57) ABSTRACT

The present invention relates to an organic light-emitting diode comprising an anode and a cathode Ka and a light-emitting layer E and if appropriate at least one further layer, where the light-emitting layer E and/or the at least one further layer comprises at least one compound selected from disilylcarbazoles, disilyldibenzofurans, disilyldibenzothiophenes, disilyldibenzophospholes, disilyldibenzothiophene S-oxides and disilyldibenzothiophene S,S-dioxides, to a light-emitting layer comprising at least one of the aforementioned compounds, to the use of the aforementioned compounds as matrix material, hole/exciton blocker material, electron/exciton blocker material, hole injection material, electron injection material, hole conductor material and/or electron conductor material, and to a device selected from the group consisting of stationary visual display units, mobile visual display units and illumination units comprising at least one inventive organic light-emitting diode.

7 Claims, No Drawings

(56) References Cited

FOREIGN PATENT DOCUMENTS

| | | |
|---|---|---|
| WO | 2006 067074 | 6/2006 |
| WO | 2006 115301 | 11/2006 |
| WO | 2007 115970 | 10/2007 |
| WO | 2007 115981 | 10/2007 |
| WO | 2007 142083 | 12/2007 |

OTHER PUBLICATIONS

U.S. Appl. No. 12/738,104, filed Apr. 15, 2010, Molt, et al.
Baldo, M. A. et al., "Very High-Efficiency Green Organic Light-Emitting Devices Based on Electrophosphorescence", Applied Physics Letters, vol. 75, No. 1, pp. 4-6 (Jul. 5, 1999).
Tsai, Ming-Han et al., "Highly Efficient Organic Blue Electrophosphorescent Devices Based on 3,6,-Bis (triphenylsilyl)Carbazole as the Host Material", Advanced Materials, vol. 18, pp. 1216-1220 (2006).
Yang, Cheng-Han et al., "Blue-Emitting Heteroleptic Indium(III) Complexes Suitable for High-Efficiency Phosphorescent OLED$_s$", Angew.Chemie, vol. 119, pp. 2470-2473 (2007).
Gustafsson, G. et al., "Flexible Light-Emitting Diodes Made From Soluble Conducting Polymers", Letters to Nature, vol. 357, pp. 477-479 (Jun. 11, 1992).
Kirk-Othmer Encyclopedia of Chemical Technology/Photoconductive Polymers, Fourth Edition, vol. 18, pp. 837-860 (1996).
Gao, W. et al., "Controlled P Doping of the Hole-Transport Molecular Material N, N'—Diphenyl-N,N' bis (1-Naphthyl)-1, 1'—biphenyl-4,4'—Diamine With Tetrafluorotetracyanoquinodimethane", Journal of Applied Physics, vol. 94, No. 1, pp. 359-366(Jul. 1, 2003).
Werner, A.G. et al, "Pyronin B As a Donor for N-Type Doping of Organic Thin Films", Applied Physics Letters, vol. 82, No. 25, pp. 4495-4497 (Jun. 23, 2003).
Pfeiffer, M. et al., "Doped Organic Semiconductors: Physics and Application in Light Emitting Diodes", Organic Electronics, vol. 4, pp. 89-103 (2003).
Borsche, W., Annalen Der Chemie, vol. 359, pp. 49-80 (1908).
Drechsel, E., Journ. F. Parkt. Chemie,[2] vol. 38, pp. 65-74 (1888).
Park, M. et al., "A Convenient Synthesis of 3,6-Substituted Carbazoles Via Nickel Catalyzed Cross-Coupling", Tetrahedron, vol. 54 pp. 12707-12714 (1998).
Yang, W. et al., "Improvement of Color Purity in Blue-Emitting Polyfluorene by Copolymerization With Dibenzothiophene", J. Mater.Chem., vol. 13, pp. 1351-1355 (2003).
Tosa, M. et al., "Selective Oxidation Methods for Preparation of N-Alkylphenothiazine Sulfoxides and Sulfones", Heterocyclic Communications, vol. 7, No. 3, pp. 277-282 (2001).
Gilman, H. et al., "Some Derivatives of Phenothiazine", vol. 66, pp. 888-893 (1944).
Li, D. et al., "Synthesis of Bis(N-Phenylphenothiazinyl-3yl) toluene Iodide", Dyes and Pigments, vol. 49, pp. 181-186 (2001).
Gozlan, I. et al., "Phase Transfer Catalysis in N-Alkylation of the Pharmaceutical Intermediates Phenothiazine and 2-Chlorophenothiazine", J.Heterocyclic Chem., vol. 21, pp. 613-614 (1984).
U.S. Appl. No. 12/306,791, filed Dec. 29, 2008, Fuchs, et al.
U.S. Appl. No. 12/597,651, filed Oct. 26, 2009, Moonen, et al.
U.S. Appl. No. 12/667,619, filed Jan. 4, 2010, Langer, et al.

* cited by examiner

ORGANIC LIGHT-EMITTING DIODES COMPRISING AT LEAST ONE DISILYL COMPOUND SELECTED FROM DISILYLCARBAZOLES, DISILYLDIBENZOFURANS, DISILYLDIBENZOTHIOPHENES, DISILYLDIBENZOPHOLES, DISILYLDIBENZOTHIOPHENE S-OXIDES AND DISILYLDIBENZOTHIOPHENE S,S-DIOXIDES

CROSS-REFERENCE TO RELATED APPLICATIONS

This application is a National Stage of PCT/EP08/058207 filed Jun. 26, 2008 and claims the benefit of EP 07111824.4 filed Jul. 5, 2007 and EP 08153306.9 filed Mar. 26, 2008.

The present invention relates to an organic light-emitting diode comprising an anode An and a cathode Ka and a light-emitting layer E and if appropriate at least one further layer, where the light-emitting layer E and/or the at least one further layer comprises at least one compound selected from disilylcarbazoles, disilyldibenzofurans, disilyldibenzothiophenes, disilyldibenzophospholes, disilyldibenzothiophene S-oxides and disilyldibenzothiophene S,S-dioxides, to a light-emitting layer comprising at least one of the aforementioned compounds, to the use of the aforementioned compounds as matrix material, hole/exciton blocker material, electron/exciton blocker material, hole injection material, electron injection material, hole conductor material and/or electron conductor material, and to a device selected from the group consisting of stationary visual display units, mobile visual display units and illumination units comprising at least one inventive organic light-emitting diode.

Organic light-emitting diodes (OLEDs) exploit the property of materials of emitting light when they are excited by electrical current. OLEDs are of particular interest as an alternative to cathode ray tubes and to liquid-crystal displays for producing flat visual display units. Owing to the very compact design and the intrinsically low power consumption, devices comprising OLEDs are suitable especially for mobile applications, for example for applications in cellphones, laptops, etc., and for illumination.

The basic principles of the way in which OLEDs work and suitable structures (layers) of OLEDs are known to those skilled in the art and are specified, for example, in WO 2005/113704 and the literature cited therein. The light-emitting materials (emitters) used may, as well as fluorescent materials (fluorescence emitters), be phosphorescent materials (phosphorescence emitters). The phosphorescence emitters are typically organometallic complexes which, in contrast to the fluorescence emitters which exhibit singlet emission, exhibit triplet emission (triplet emitters) (M. A. Baldow et al., Appl. Phys. Lett. 1999, 75, 4 to 6). For quantum-mechanical reasons, when the triplet emitters (phosphorescence emitters) are used, up to four times the quantum efficiency, energy efficiency and power efficiency is possible. In order to implement the advantages of the use of the organometallic triplet emitters (phosphorescence emitters) in practice, it is necessary to provide device compositions which have a high operative lifetime, a good efficiency, a high stability to thermal stress and a low use and operating voltage.

Such device compositions may, for example, comprise specific matrix materials in which the actual light emitter is present in distributed form. In addition, the compositions may comprise blocker materials, it being possible for hole blockers, exciton blockers and/or electron blockers to be present in the device compositions. Additionally or alternatively, the device compositions may further comprise hole injection materials and/or electron injection materials and/or hole conductor materials and/or electron conductor materials. The selection of the aforementioned materials which are used in combination with the actual light emitter has a significant influence on parameters including the efficiency and the lifetime of the OLEDs.

The prior art proposes numerous different materials for use in the different layers of OLEDs.

US 2005/0238919 A1 relates to an organic light-emitting diode which comprises at least one aryl compound which comprises two or more silicon atoms. The materials specified in US 2005/0238919 A1 are preferably used as matrix materials in the light-emitting layer. Organic light-emitting diodes which comprise disilyldibenzofurans, disilyldibenzothiophenes, disilyldibenzophospholes, disilyldibenzothiophene S-oxides and disilyldibenzothiophene S,S-dioxides, or carbazoles which—when used exclusively in the light-emitting layer or simultaneously in the light-emitting layer and in the hole conductor layer—have at least one further heteroatom, are not disclosed in US 2005/0238919 A1. In addition, US 200570238919 A1 specifies a large number of differently substituted silicon-comprising compounds, but only silicon-comprising compounds of the formulae (1-1) and (1-2) which have the following formulae

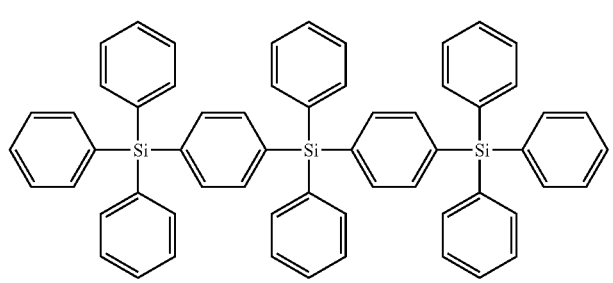

(1-1)

-continued

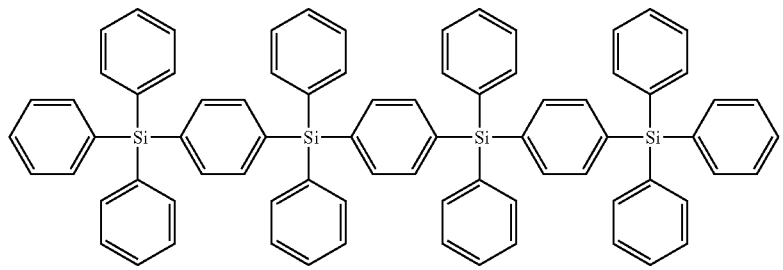

(1-2)

are used in the examples of the present application.

Tsai et al., Adv. Mater., 2006, Vol. 18, No. 9, pages 1216 to 1220 discloses organic blue-light emitting diodes which comprise 9-(4-tert-butylphenyl)-3,6-bis(triphenylsilyl)carbazole as matrix material.

Yang et al., Angew. Chem. 2007, 119, 2470 to 2473 relates to blue light-emitting heteroleptic iridium(III) complexes which are suitable for use in phosphorescent OLEDs. In the examples according to Yang et al., the hole transport material and exciton blocker material used, which lies between hole conductor layer and emitter layer, is 9-(4-tert-butylphenyl)-3,6-bis(triphenylsilyl)carbazole in addition to 9-(4-tert-butylphenyl)-3,6-bis(triphenylsilyl)carbazole as a matrix material.

JP 2004253298 A relates to organic white light-emitting diodes in which substituted triphenylsilanes are used as matrix materials.

It is therefore an object of the present invention, with respect to the prior art, to provide novel device compositions for OLEDs which comprise the novel materials for improving the performance of the OLED. The materials suitable for the novel device compositions should be easy to obtain and, in combination with the emitter(s), bring about good efficiencies and good lifetimes in OLEDs.

This object is achieved by the provision of an organic light-emitting diode comprising an anode An and a cathode Ka and a light-emitting layer E
and if appropriate at least one further layer selected from the group consisting of: at least one blocking layer for electrons/excitons, at least one blocking layer for holes/excitons, at least one hole injection layer, at least one hole conductor layer, at least one electron injection layer and a least one electron conductor layer,
wherein the organic light-emitting diode comprises at least one compound of the general formula I which is present in the light-emitting layer E and/or in the at least one further layer,

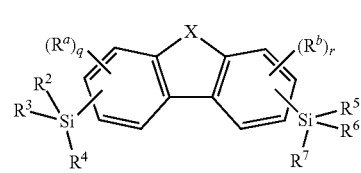

(I)

in which:
X is $NR^1$, S, O, $PR^1$, $SO_2$ or SO;
$R^1$ is substituted or unsubstituted $C_1$-$C_{20}$-alkyl, substituted or unsubstituted $C_6$-$C_{30}$-aryl, or substituted or unsubstituted heteroaryl having from 5 to 30 ring atoms;

$R^2$, $R^3$, $R^4$, $R^5$, $R^6$, $R^7$ are each independently substituted or unsubstituted $C_1$-$C_{20}$-alkyl, or substituted or unsubstituted $C_6$-$C_{30}$-aryl, or a structure of the general formula (c)

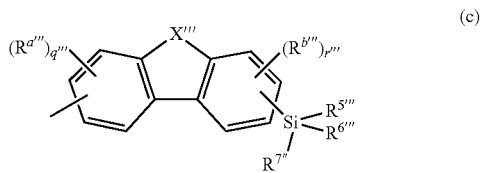

(c)

$R^a$, $R^b$ are each independently substituted or unsubstituted $C_1$-$C_{20}$-alkyl, substituted or unsubstituted $C_6$-$C_{30}$-aryl, or substituted or unsubstituted heteroaryl having from 5 to 30 ring atoms or a substituent with donor or acceptor action selected from the group consisting of: $C_1$-$C_{20}$-alkoxy, $C_6$-$C_{30}$-aryloxy, $C_1$-$C_{20}$-alkylthio, $C_6$-$C_{30}$-arylthio, $SiR^{14}R^{15}R^{16}$, halogen radicals, halogenated $C_1$-$C_{20}$-alkyl radicals, carbonyl (—CO($R^{14}$)), carbonylthio (—C=O($SR^{14}$)), carbonyloxy (—C=O($OR^{14}$)), oxycarbonyl (—OC=O($R^{14}$)), thiocarbonyl (—SC=O($R^{14}$)), amino (—$NR^{14}R^{15}$), OH, pseudohalogen radicals, amido (—C=O ($NR^{14}$)), —$NR^{14}$C=O($R^{15}$), phosphonate (—P(O)($OR^{14}$)$_2$), phosphate (—OP(O)($OR^{14}$)$_2$), phosphine (—$PR^{14}R^{15}$), phosphine oxide (—P(O)$R^{14}{}_2$), sulfate (—OS(O)$_2$$OR^{14}$), sulfoxide (—S(O)$R^{14}$), sulfonate (—S(O)$_2$$OR^{14}$), sulfonyl (—S(O)$_2$$R^{14}$), sulfonamide (—S(O)$_2$$NR^{14}R^{15}$), $NO_2$, boronic esters (—OB($OR^{14}$)$_2$), imino (—C=$NR^{14}R^{15}$)), borane radicals, stannane radicals, hydrazine radicals, hydrazone radicals, oxime radicals, nitroso groups, diazo groups, vinyl groups, sulfoximines, alanes, germanes, boroximes and borazines;

$R^{14}$, $R^{15}$, $R^{16}$
are each independently substituted or unsubstituted $C_1$-$C_{20}$-alkyl, or substituted or unsubstituted $C_6$-$C_{30}$-aryl;

q,r are each independently 0, 1, 2 or 3; where, in the case when q or r is 0, all substitutable positions of the aryl radical are substituted by hydrogen, where the radicals and indices in the group of the formula (c) $X'''$, $R^{5'''}$, $R^{6'''}$, $R^{7'''}$, $R^{a'''}$, $R^{b'''}$, q''' and r''' are each independently as defined for the radicals and indices of the compounds of the general formula (I) X, $R^5$, $R^6$, $R^7$, $R^a$, $R^b$, q and r;

where,
in the case that the compound of the general formula (I) is present exclusively in the light-emitting layer or in the light-emitting layer and in the hole conductor layer and the group X is $NR^1$, at least one of the $R^1$ to $R^7$, $R^a$ or $R^b$ radicals in the compounds of the formula (I) comprises at least one heteroatom.

The compounds of the general formula (I) are easy to obtain and have good efficiencies when used in OLEDs both when used as matrix materials in the light-emitting layer E and when used in at least one of the further layers of an OLED, and are suitable for providing OLEDs with a long lifetime.

Depending on their substitution pattern, the compounds of the formula (I) can be used as a matrix in the light-emitting layer E, as a hole/exciton blocker, as an electron/exciton blocker, as hole injection materials, as electron injection materials, as hole conductors and/or as electron conductors. Corresponding layers of OLEDs are known to those skilled in the art and are specified, for example, in WO 2005/113704 or WO 2005/019373.

Structure of the Inventive OLEDs

The inventive organic light-emitting diode (OLED) has the following structure:

an anode (An) and a cathode (Ka) and a light-emitting layer E which is arranged between the anode (An) and the cathode (Ka), and if appropriate at least one further layer selected from the group consisting of: at least one blocking layer for electrons/excitons, at least one blocking layer for holes/excitons, at least one hole injection layer, at least one hole conductor layer, at least one electron injection layer and at least one electron conductor layer.

It is additionally possible that a plurality of the aforementioned functions (electron/exciton blocker, hole/exciton blocker, hole injection, hole conduction, electron injection, electron conduction) are combined in one layer and, for example, are assumed by a single material present in this layer. For example, a material used in the hole conductor layer may, in one embodiment, simultaneously block excitons and/or electrons.

Furthermore, the individual aforementioned layers of the OLED may in turn be formed from 2 or more layers. For example, the hole conductor layer may be formed from a layer into which holes are injected from the electrode, and a layer which transports the holes away from the hole-injecting layer into the light-emitting layer. The electron conduction layer may likewise consist of a plurality of layers, for example a layer in which electrons are injected through the electrode, and a layer which receives electrons from the electron injection layer and transports them into the light-emitting layer. The layers mentioned are each selected according to factors such as energy level, thermal resistance and charge carrier mobility, and also energy difference of the layers mentioned with the organic layers or the metal electrodes. The person skilled in the art is capable of selecting the construction of the OLEDs such that it is adjusted optimally to the organic compounds used in accordance with the invention as emitter substances.

In order to obtain particularly efficient OLEDs, for example, the HOMO (highest occupied molecular orbital) of the hole conductor layer should be matched to the work function of the anode, and the LUMO (lowest unoccupied molecular orbital) of the electron conductor layer should be matched to the work function of the cathode, when the aforementioned layers are present in the inventive OLEDs.

The inventive OLED may for example—in a preferred embodiment—be composed of the following layers:
1. anode
2. hole conductor layer
3. light-emitting layer
4. blocking layer for holes/excitons
5. electron conductor layer
6. cathode Layer sequences different from the aforementioned construction are also possible, and are known to those skilled in the art. For example, it is possible that the OLED does not have all of the layers mentioned; for example, an OLED comprising layers (1) (anode), (3) (light-emitting layer) and (6) (cathode) is likewise suitable, in which case the functions of layers (2) (hole conductor layer) and (4) (blocking layer for holes/excitons) and (5) (electron conductor layer) are assumed by the adjacent layers. OLEDs which have layers (1), (2), (3) and (6) or layers (1), (3), (4), (5) and (6) are likewise suitable. In addition, the OLEDs may have a blocking layer for electrons/excitons between the anode (1) and the hole conductor layer (2).

The anode (1) is an electrode which provides positive charge carriers. It may be constructed, for example, from materials which comprise a metal, a mixture of different metals, a metal alloy, a metal oxide or a mixture of different metal oxides. Alternatively, the anode may be a conductive polymer. Suitable metals comprise the metals of groups Ib, IVa, Va and VIa of the Periodic Table of the Elements, and the transition metals of group VIIIa. When the anode is to be transparent, generally mixed metal oxides of groups IIb, IIIb and IVb of the Periodic Table of the Elements (old IUPAC version) are used, for example indium tin oxide (ITO). It is likewise possible that the anode (1) comprises an organic material, for example polyaniline, as described, for example, in Nature, Vol. 357, pages 477 to 479 (Jun. 11, 1992). At least either the anode or the cathode should be at least partly transparent in order to be able to emit the light formed. The material used for the anode (1) is preferably ITO.

Suitable hole conductor materials for layer (2) of the inventive OLEDs are disclosed, for example, in Kirk-Othmer Encyclopedia of Chemical Technology, 4th edition, vol. 18, pages 837 to 860, 1996. Both hole-transporting molecules and polymers can be used as hole transport material. Customarily used hole-transporting molecules are selected from the group consisting of tris[N-(1-naphthyl)-N-(phenylamino)]triphenylamine (1-NaphDATA), 4,4'-bis[N-(1-naphthyl)-N-phenylamino]biphenyl (α-NPD), N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino)benzaldehyde diphenyl hydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), 4,4',4"-tris(N,N-diphenylamino)tri-phenylamine (TDTA), porphyrin compounds and phthalocyanines such as copper phthalocyanines. Customarily used hole-transporting polymers are selected from the group consisting of polyvinylcarbazoles, (phenylmethyl)polysilanes and polyanilines. It is likewise possible to obtain hole-transporting polymers by doping hole-transporting molecules into polymers such as polystyrene and polycarbonate. Suitable hole-transporting molecules are the molecules already mentioned above.

In addition—in a preferred embodiment—carbene complexes can be used as hole conductor materials, in which case the band gap of the at least one hole conductor material is generally greater than the band gap of the emitter material used. In the context of the present application, band gap is understood to mean the triplet energy. Suitable carbene complexes are, for example, carbene complexes as described in WO 2005/019373 A2, WO 2006/056418 A2 and WO 2005/113704 and in the prior European patent applications EP 06 112 228.9 and EP 06 112 198.4, which were yet to be published at the priority date of the present application.

The light-emitting layer (3) comprises at least one emitter material. This may in principle be a fluorescence or phosphorescence emitter, suitable emitter materials being known to those skilled in the art. The at least one emitter material is preferably a phosphorescence emitter. The phosphorescence emitter compounds used with preference are based on metal complexes, and especially the complexes of the metals Ru, Rh, Ir, Pd and Pt, in particular the complexes of Ir, have gained significance. The compounds of the formula I used in accordance with the invention are suitable particularly for use together with such metal complexes. In a preferred embodiment, the compounds of the formula (I) are used as matrix materials and/or hole/exciton blocker materials and/or electron/exciton blocker materials. In particular, they are suitable for use as matrix materials and/or hole/exciton blocker materials and/or electron/exciton blocker materials together with complexes of Ru, Rh, Ir, Pd and Pt, more preferably for use together with complexes of Ir.

Suitable metal complexes for use in the inventive OLEDs are described, for example, in documents WO 02/60910 A1, US 2001/0015432 A1, US 2001/0019782 A1, US 2002/0055014 A1, US 2002/0024293 A1, US 2002/0048689 A1, EP 1 191 612 A2, EP 1 191 613 A2, EP 1 211 257 A2, US 2002/0094453 A1, WO 02/02714 A2, WO 00/70655 A2, WO 01/41512 A1, WO 02/15645 A1, WO 2005/019373 A2, WO 2005/113704 A2, WO 2006/115301 A1, WO 2006/067074 A1 and WO 2006/056418.

Further suitable metal complexes are the commercially available metal complexes tris(2-phenylpyridine)iridium (III), tris(2-(4-tolyppyridinato-N,$C^{2'}$)iridium(III), tris(1-phenylisoquinoline)iridium(III), bis(2-(2'-benzothienyl)pyridinato-N,$C^{3'}$)(acetylacetonato)iridium(III), iridium(III) bis(2-(4,6-difluorophenyl)pyridinato-N,$C^2$)picolinate, iridium(III) bis(1-phenylisoquinoline)(acetylacetonate), iridium(III) bis(dibenzo[f,h]quinoxaline)(acetylacetonate), iridium(III) bis(2-methyldibenzo[f,h]quinoxaline)(acetylacetonate) and tris(3-methyl-1-phenyl-4-trimethylacetyl-5-pyrazoline)terbium (III).

In addition, the following commercially available materials are suitable: tris(dibenzoylacetonato)mono(phenanthroline)europium(III), tris(dibenzoylmethane)-mono(phenanthroline)europium(III), tris(dibenzoylmethane)mono(5-aminophenan-throline)europium(III), tris(di-2-naphthoylmethane)mono(phenanthroline)europium(III), tris(4-bromobenzoylmethane)mono(phenanthroline)europium (III), tris(di(biphenylmethane))mono(phenanthroline)europium(III), tris(dibenzoylmethane)mono(4,7-diphenylphenanthroline)europium(III), tris(dibenzoylmethane)mono(4,7-dimethylphenanthroline) europium(III), tris(dibenzoylmethane)mono(4,7-dimethylphenanthroline-disulfonic acid)europium(III) disodium salt, tris[di(4-(2-(2-ethoxyethoxy)ethoxy)benzoylmethane)]mono(phenanthroline)europium(III) and tris[di[4-(2-(2-ethoxyethoxy)-ethoxy)benzoylmethane)]mono(5-aminophenanthroline)europium(III).

Particularly preferred triplet emitters are carbene complexes. In a preferred embodiment of the present invention, the compounds of the formula (I) are used in the light-emitting layer as a matrix material together with carbene complexes as triplet emitters. Suitable carbene complexes are known to those skilled in the art and are specified in some of the aforementioned applications and below. In a further preferred embodiment, the compounds of the formula (I) are used as hole/exciton blocker material together with carbene complexes as triplet emitters. The compounds of the formula (I) may additionally be used both as matrix materials and as hole/exciton blocker materials together with carbene complexes as triplet emitters.

Suitable metal complexes for use together with the compounds of the formula I as matrix materials and/or hole/exciton block materials and/or electron/exciton blocker materials in OLEDs are thus, for example, also carbene complexes as described in WO 2005/019373 A2, WO 2006/056418 A2 and WO 2005/113704, and in the prior European applications EP 06 112 228.9 and EP 06 112 198.4, which were yet to be published at the priority date of the present application. Reference is hereby made explicitly to the disclosure of the WO and EP applications mentioned, and these disclosures shall be incorporated into the content of the present application.

The blocking layer for holes/excitons (4) may typically comprise hole blocker materials used in OLEDs, such as 2,9-dimethyl-4,7-diphenyl-1,10-phenanthroline (bathocuproin, (BCP)), bis(2-methyl-8-quinolinato)-4-phenylphenylato)aluminum(III) (BAlq), phenothiazine S,S-dioxide derivatives and 1,3,5-tris(N-phenyl-2-benzylimidazole)-benzene (TPBI), TPBI also being suitable as an electron-conducting material. In a further embodiment, compounds which comprise aromatic or heteroaromatic rings bonded via groups comprising carbonyl groups, as disclosed in WO2006/100298, may be used as blocking layer for holes/excitons (4) or as matrix materials in the light-emitting layer (3).

In addition, the blocking layer for holes/excitons may comprise a compound of the general formula (I), in which case compounds of the formula (I) suitable with preference as hole blocker/exciton blocker materials are specified below.

In a preferred embodiment, the present invention relates to an inventive OLED comprising layers (1) anode, (2) hole conductor layer, (3) light-emitting layer, (4) blocking layer for holes/excitons, (5) electron conductor layer and (6) cathode, and if appropriate further layers, the blocking layer for holes/excitons comprising at least one compound of the formula (I).

In a further preferred embodiment, the present invention relates to an inventive OLED comprising layers (1) anode, (2) hole conductor layer, (3) light-emitting layer, (4) blocking layer for holes/excitons, (5) electron conductor layer and (6) cathode, and if appropriate further layers, the light-emitting layer (3) comprising at least one compound of the formula (I), and the blocking layer for holes/excitons at least one compound of the formula (I).

In a further embodiment, the present invention relates to an inventive OLED comprising layers (1) anode, (2) hole conductor layer and/or (2') blocking layer for electrons/excitons (the OLED may comprise both layers (2) and (2'), or else either layer (2) or layer (2')), (3) light-emitting layer, (4) blocking layer for holes/excitons, (5) electron conductor layer and (6) cathode, and if appropriate further layers, the blocking layer for electrons/excitons and/or the hole conductor layer and if appropriate the light-emitting layer (3) comprising at least one compound of the formula (I).

Suitable electron conductor materials for layer (5) of the inventive OLEDs comprise metals chelated with oxinoid compounds, such as 2,2',2"-(1,3,5-phenylene)tris[1-phenyl-1H-benzimidazole] (TPBI), tris(8-quinolinolato)aluminum ($Alq_3$), compounds based on phenanthroline, such as 2,9-dimethyl-4,7-diphenyl-1,10-phenanthroline (DDPA=BCP) or 4,7-diphenyl-1,10-phenanthroline (DPA), and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ). The layer (5) may serve either to facilitate electron transport or as a buffer layer or as a barrier layer in order to prevent quenching of the exciton at the interfaces of the layers of the OLED. The layer (5) preferably improves the mobility of the electrons and reduces quenching of the exciton. In a preferred embodiment, TPBI is used as the electron conductor material.

Among the materials mentioned above as hole conductor materials and electron conductor materials, some may fulfill several functions. For example, some of the electron-conducting materials are simultaneously hole-blocking materials when they have a low-lying HOMO. These may be used, for example, in the blocking layer for holes/excitons (4). However, it is likewise possible that the function as a hole/exciton blocker is also assumed by layer (5), such that layer (4) can be dispensed with.

The charge transport layers may also be electronically doped in order to improve the transport properties of the materials used, in order firstly to make the layer thicknesses more generous (avoidance of pinholes/short circuits) and in order secondly to minimize the operating voltage of the device. For example, the hole conductor materials may be doped with electron acceptors; for example, it is possible to dope phthalocyanines or arylamines such as TPD or TDTA with tetrafluorotetracyanoquinodimethane (F4-TCNQ). The electron conductor materials may, for example, be doped with alkali metals, for example $Alq_3$ with lithium. Electronic doping is known to those skilled in the art and is disclosed, for example, in W. Gao, A. Kahn, J. Appl. Phys., Vol. 94, No. 1, Jul. 1, 2003 (p-doped organic layers); A. G. Werner, F. Li, K. Harada, M. Pfeiffer, T. Fritz, K. Leo. Appl. Phys. Lett., Vol. 82, No. 25, Jun. 23, 2003 and Pfeiffer et al., Organic Electronics 2003, 4, 89-103.

The cathode (6) is an electrode which serves to introduce electrons or negative charge carriers. Suitable materials for the cathode are selected from the group consisting of alkali metals of group Ia, for example Li, Cs, alkaline earth metals of group IIa, for example calcium, barium or magnesium, metals of group IIb of the Periodic Table of the Elements (old IUPAC version), comprising the lanthanides and actinides, for example samarium. In addition, it is also possible to use metals such as aluminum or indium, and combinations of all metals mentioned. In addition, lithium-comprising organometallic compounds or LiF may be applied between the organic layer and the cathode in order to reduce the operating voltage.

The OLED according to the present invention may additionally comprise further layers which are known to those skilled in the art. For example, between the layer (2) and the light-emitting layer (3) may be applied a layer which facilitates the transport of the positive charge and/or matches the band gap of the layers to one another. Alternatively, this further layer may serve as a protective layer. In an analogous manner, additional layers may be present between the light-emitting layer (3) and the layer (4) in order to facilitate the transport of the negative charge and/or to match the band gap between the layers to one another. Alternatively, this layer may serve as a protective layer.

In a preferred embodiment, the inventive OLED comprises, in addition to layers (1) to (6), at least one of the further layers specified below:
- a hole injection layer between the anode (1) and the hole-transporting layer (2);
- a blocking layer for electrons between the hole-transporting layer (2) and the light-emitting layer (3);
- an electron injection layer between the electron-transporting layer (5) and the cathode (6).

Those skilled in the art are aware of how suitable materials have to be selected (for example on the basis of electrochemical studies). Suitable materials for the individual layers are known to those skilled in the art and are disclosed, for example, in WO 00/70655.

In addition, it is possible that some of the layers used in the inventive OLED are surface-treated in order to increase the efficiency of charge carrier transport. The selection of the materials for each of the layers mentioned is preferably determined so as to obtain an OLED with high efficiency and lifetime.

The inventive OLED can be produced by methods known to those skilled in the art. In general, the inventive OLED is produced by successive vapor deposition of the individual layers onto a suitable substrate. Suitable substrates are, for example, glass, inorganic semiconductors or polymer films. For the vapor deposition, it is possible to use customary techniques such as thermal evaporation, chemical vapor deposition (CVD), physical vapor deposition (PVD) and others. In an alternative process, the organic layers of the OLEDs may be coated from solutions or dispersions in suitable solvents, for which coating techniques known to those skilled in the art are employed.

In general, the different layers have the following thicknesses: anode (1) from 50 to 500 nm, preferably from 100 to 200 nm; hole-conducting layer (2) from 5 to 100 nm, preferably from 20 to 80 nm, light-emitting layer (3) from 1 to 100 nm, preferably from 10 to 80 nm, blocking layer for holes/excitons (4) from 2 to 100 nm, preferably from 5 to 50 nm, electron-conducting layer (5) from 5 to 100 nm, preferably from 20 to 80 nm, cathode (6) from 20 to 1000 nm, preferably from 30 to 500 nm. The relative position of the recombination zone of holes and electrons in the inventive OLED in relation to the cathode and hence the emission spectrum of the OLED can be influenced, inter alia, by the relative thickness of each layer. This means that the thickness of the electron transport layer should preferably be selected such that the position of the recombination zone is matched to the optical resonator property of the diode and hence to the emission wavelength of the emitter. The ratio of the layer thicknesses of the individual layers in the OLED depends on the materials used. The layer thicknesses of any additional layers used are known to those skilled in the art. It is possible that the electron-conducting layer and/or the hole-conducting layer has/have greater thicknesses than the layer thicknesses specified when they are electrically doped.

According to the invention, the light-emitting layer E and/or at least one of the further layers optionally present in the inventive OLED comprises at least one compound of the general formula (I). While the at least one compound of the general formula (I) is present in the light-emitting layer E as a matrix material, the at least one compound of the general formula (I) can be used in the at least one further layer of the inventive OLED in each case alone or together with at least one of the further aforementioned materials suitable for the corresponding layers.

Substituted or unsubstituted $C_1$-$C_{20}$-alkyl is understood to mean alkyl radicals having from 1 to 20 carbon atoms. Preference is given to $C_1$- to $C_{10}$-alkyl radicals, particular preference to $C_1$- to $C_6$-alkyl radicals. The alkyl radicals may be either straight-chain or branched or cyclic, where the alkyl radicals in the case of cyclic alkyl radicals have at least 3 carbon atoms. In addition, the alkyl radicals may be substituted by one or more substituents selected from the group consisting of $C_1$-$C_{20}$-alkoxy, halogen, preferably F, and $C_6$-$C_{30}$-aryl which may in turn be substituted or unsubstituted. Suitable aryl substituents and suitable alkoxy and halogen substituents are specified below. Examples of suitable alkyl groups are methyl, ethyl, propyl, butyl, pentyl, hexyl, heptyl and octyl, and also derivatives of the alkyl groups mentioned substituted by $C_6$-$C_{30}$-aryl, $C_1$-$C_{20}$-alkoxy and/or halogen, especially F, for example $CF_3$. Also included are both the n-isomers of the radicals mentioned and branched isomers such as isopropyl, isobutyl, isopentyl, sec-butyl, tert-butyl, neopentyl, 3,3-dimethylbutyl, 3-ethylhexyl etc. Preferred alkyl groups are methyl, ethyl, tert-butyl and $CF_3$.

Examples of suitable cyclic alkyl groups, which may likewise be unsubstituted or substituted by the above radicals specified for the alkyl groups, are cyclopropyl, cyclobutyl, cyclopentyl, cyclohexyl, cycloheptyl, cyclooctyl, cyclononyl and cyclodecyl. If appropriate, the ring systems may also be polycyclic ring systems such as decalinyl, norbornyl, bornanyl or adamantyl.

Suitable $C_1$-$C_{20}$-alkoxy and $C_1$-$C_{20}$-alkylthio groups derive correspondingly from the aforementioned $C_1$-$C_{20}$-alkyl radicals. Examples here include $OCH_3$, $OC_2H_5$, $OC_3H_7$, $OC_4H_9$ and $OC_8H_{17}$, and also $SCH_3$, $SC_2H_5$, $SC_3H_7$, $SC_4H_9$ and $SC_8H_{17}$. $C_3H_7$, $C_4H_9$ and $C_8H_{17}$ are understood to mean both the n-isomers and branched isomers such as isopropyl, isobutyl, sec-butyl, tert-butyl and 2-ethylhexyl. Particularly preferred alkoxy or alkylthio groups are methoxy, ethoxy, n-octyloxy, 2-ethylhexyloxy and $SCH_3$.

Suitable halogen radicals or halogen substituents in the context of the present application are fluorine, chlorine, bromine and iodine, preferably fluorine, chlorine and bromine, more preferably fluorine and chlorine, most preferably fluorine.

Suitable pseudohalogen radicals in the context of the present application are CN, SCN, OCN, $N_3$ and SeCN, preference being given to CN and SCN. Very particular preference is given to CN.

In the present invention, $C_6$-$C_{30}$-aryl refers to radicals which are derived from monocyclic, bicyclic or tricyclic aromatics which do not comprise any ring heteroatoms. When the system is not a monocyclic system, the saturated form (perhydro form) or the partly unsaturated form (for example the dihydro form or tetrahydro form) are also possible for the second ring in case of the designation "aryl", provided that the particular forms are known and stable. In other words, the term "aryl" in the present invention also comprises, for example, bicyclic or tricyclic radicals in which either both or all three radicals are aromatic, and also bicyclic or tricyclic radicals in which only one ring is aromatic, and also tricyclic radicals in which two rings are aromatic. Examples of aryl are: phenyl, naphthyl, indanyl, 1,2-dihydronaphthenyl, 1,4-dihydronaphthenyl, indenyl, anthracenyl, phenanthrenyl or 1,2,3,4-tetrahydronaphthyl. Particular preference is given to $C_6$-$C_{10}$-aryl radicals, for example phenyl or naphthyl, very particular preference to $C_6$-aryl radicals, for example phenyl.

The $C_6$-$C_{30}$-aryl radicals may be unsubstituted or substituted by one or more further radicals. Suitable further radicals are selected from the group consisting of $C_1$-$C_{20}$-alkyl, $C_6$-$C_{30}$-aryl or substituents with donor or acceptor action, suitable substituents with donor or acceptor action being specified below. The $C_6$-$C_{30}$-aryl radicals are preferably unsubstituted or substituted by one or more $C_1$-$C_{20}$-alkoxy groups, CN, $CF_3$, F or amino groups ($NR^{14}R^{15}$, where suitable $R^{14}$ and $R^{15}$ radicals are specified above). Further preferred substitutions of the $C_6$-$C_{30}$-aryl radicals depend on the end use of the compounds of the general formula (I) and are specified below.

Suitable $C_6$-$C_{30}$-aryloxy, $C_6$-$C_{30}$-alkylthio radicals derive correspondingly from the aforementioned $C_6$-$C_{30}$-aryl radicals. Particular preference is given to phenoxy and phenylthio.

Unsubstituted or substituted heteroaryl having from 5 to 30 ring atoms is understood to mean monocyclic, bicyclic or tricyclic heteroaromatics which derive partly from the aforementioned aryl, in which at least one carbon atom in the aryl base skeleton has been replaced by a heteroatom. Preferred heteroatoms are N, O and S. The heteroaryl radicals more preferably have from 5 to 13 ring atoms. Especially preferably, the base skeleton of the heteroaryl radicals is selected from systems such as pyridine and five-membered heteroaromatics such as thiophene, pyrrole, imidazole or furan. These base structures may optionally be fused to one or two six-membered aromatic radicals. Suitable fused heteroaromatics are carbazolyl, benzimidazolyl, benzofuryl, dibenzofuryl or dibenzothiophenyl. The base structure may be substituted at one, more than one or all substitutable positions, suitable substituents being the same as have already been specified under the definition of $C_6$-$C_{30}$-aryl. However, the heteroaryl radicals are preferably unsubstituted. Suitable heteroaryl radicals are, for example, pyridin-2-yl, pyridin-3-yl, pyridin-4-yl, thiophen-2-yl, thiophen-3-yl, pyrrol-2-yl, pyrrol-3-yl, furan-2-yl, furan-3-yl and imidazol-2-yl, and also the corresponding benzofused radicals, especially carbazolyl, benzimidazolyl, benzofuryl, dibenzofuryl or dibenzothiophenyl.

In the context of the present application, groups with donor or acceptor action are understood to mean the following groups:

$C_1$-$C_{20}$-alkoxy, $C_6$-$C_{30}$-aryloxy, $C_1$-$C_{20}$-alkylthio, $C_6$-$C_{30}$-arylthio, $SiR^{14}R^{15}R^{16}$, halogen radicals, halogenated $C_1$-$C_{20}$-alkyl radicals, carbonyl (—$CO(R^{14})$), carbonylthio (—C=$O(SR^{14})$), carbonyloxy (—C=$O(OR^{14})$), oxycarbonyl (—OC=$O(R^{14})$), thiocarbonyl (—SC=$O(R^{14})$), amino (—$NR^{14}R^{15}$), OH, pseudohalogen radicals, amido (—C=O($NR^{14}$)), —$NR^{14}$C=$O(R^{15})$, phosphonate (—$P(O)(OR^{14})_2$, phosphate (—$OP(O)(OR^{14})_2$), phosphine (—$PR^{14}R^{15}$), phosphine oxide (—$P(O)R^{14}{}_2$), sulfate (—$OS(O)_2OR^{14}$), sulfoxide ($S(O)R^{14}$), sulfonate (—$S(O)_2OR^{14}$), sulfonyl (—$S(O)_2R^{14}$), sulfonamide (—$S(O)_2NR^{14}R^{15}$), $NO_2$, boronic esters (—$OB(OR^{14})_2$), imino (—C=$NR^{14}R^{15}$)), borane radicals, stannane radicals, hydrazine radicals, hydrazone radicals, oxime radicals, nitroso groups, diazo groups, vinyl groups and boric acid groups, sulfoximines, alanes, germanes, boroximes and borazines.

Preferred substituents with donor or acceptor action are selected from the group consisting of:

$C_1$- to $C_{20}$-alkoxy, preferably $C_1$-$C_6$-alkoxy, more preferably ethoxy or methoxy; $C_6$-$C_{30}$-aryloxy, preferably $C_6$-$C_{10}$-aryloxy, more preferably phenyloxy; $SiR^{14}R^{15}R^{16}$ where $R^{14}$, $R^{15}$ and $R^{16}$ are preferably each independently substituted or unsubstituted alkyl or substituted or unsubstituted phenyl; at least one of the $R^{14}$, $R^{15}$ or $R^{16}$ radicals is more preferably substituted or unsubstituted phenyl; at least one of the $R^{14}$, $R^{15}$ and $R^{16}$ radicals is most preferably substituted phenyl, suitable substituents having been specified above; halogen radicals, preferably F, Cl, Br, more preferably F or Cl, most preferably F, halogenated $C_1$-$C_{20}$-alkyl radicals, preferably halogenated $C_1$-$C_6$-alkyl radicals, most preferably fluorinated $C_1$-$C_6$-alkyl radicals, e.g. $CF_3$, $CH_2F$, $CHF_2$ or $C_2F_5$; amino, preferably dimethylamino, diethylamino or diphenylamino; OH, pseudohalogen radicals, preferably CN, SCN or OCN, more preferably CN, —$C(O)OC_1$-$C_4$-alkyl, preferably —$O(O)OMe$, $P(O)R_2$, preferably $P(O)Ph_2$, or $SO_2R_2$, preferably $SO_2Ph$.

Very particularly preferred substituents with donor or acceptor action are selected from the group consisting of methoxy, phenyloxy, halogenated $C_1$-$C_4$-alkyl, preferably $CF_3$, $CH_2F$, $CHF_2$, $C_2F_5$, halogen, preferably F, CN, $SiR^{14}R^{15}R^{16}$, where suitable $R^{14}$, $R^{15}$ and $R^{16}$ radicals have already been mentioned, diphenylamino, —$O(O)OC_1$-$C_4$-alkyl, preferably —$C(O)OMe$, $P(O)Ph_2$, $SO_2Ph$.

The aforementioned groups with donor or acceptor action are not intended to rule out the possibility that further aforementioned radicals and groups may also have donor or acceptor action. For example, the aforementioned heteroaryl groups are likewise groups with donor or acceptor action, and the $C_1$-$C_{20}$-alkyl radicals are groups with donor action.

The $R^{14}$, $R^{15}$ and $R^{16}$ radicals mentioned in the aforementioned groups with donor or acceptor action are each as already defined above, i.e. $R^{14}$, $R^{15}$, $R^{16}$ each independently: substituted or unsubstituted $C_1$-$C_{20}$-alkyl or substituted or unsubstituted $C_6$-$C_{30}$-aryl, suitable and preferred alkyl and aryl radicals having been specified above. More preferably, the $R^{14}$, $R^{15}$ and $R^{16}$ radicals are $C_1$-$C_6$-alkyl, e.g. methyl, ethyl or i-propyl, phenyl. In a preferred embodiment—in the case of $SiR^{14}R^{15}R^{16}$—$R^{14}$, $R^{15}$ and $R^{16}$ are preferably each independently substituted or unsubstituted $C_1$-$C_{20}$-alkyl or substituted or unsubstituted phenyl; more preferably, at least one of the $R^{14}$, $R^{15}$ and $R^{16}$ radicals is substituted or unsubstituted phenyl; most preferably, at least one of the $R^{14}$, $R^{15}$ and $R^{16}$ radicals is substituted phenyl, suitable substituents having been specified above.

The expressions "electron-donating substituents" and "electron-withdrawing substituents" used additionally in the present application are substituents with donor action (electron-donating substituents) or substituents with acceptor action (electron-withdrawing substituents). Suitable electron-donating and electron-withdrawing substituents are thus the substituents which have already been specified above for the substituents with donor or acceptor action.

Compounds of the Formula (I)

The compounds of the formula (I) are disilyl compounds in which the radicals and indices are each defined as follows:

X is $NR^1$, S, O, $PR^1$, $SO_2$ or SO; preferably $NR^1$, S or O;

$R^1$ is substituted or unsubstituted $C_1$-$C_{20}$-alkyl, substituted or unsubstituted $C_6$-$C_{30}$-aryl, or substituted or unsubstituted heteroaryl having from 5 to 30 ring atoms; preferably substituted or unsubstituted $C_1$-$C_{20}$-alkyl or substituted or unsubstituted $C_6$-$C_{30}$-aryl, more preferably substituted or unsubstituted $C_6$-$C_{10}$-aryl or unsubstituted $C_1$-$C_{20}$-alkyl, most preferably substituted or unsubstituted phenyl, suitable substituents having been specified above;

$R^2$, $R^3$, $R^4$, $R^5$, $R^6$, $R^7$
are each independently substituted or unsubstituted $C_1$-$C_{20}$-alkyl or substituted or unsubstituted $C_6$-$C_{30}$-aryl or a structure of the general formula (c);
preferably at least one of the $R^2$, $R^3$ and $R^4$ radicals and/or at least one of the $R^5$, $R^6$ and $R^7$ radicals is substituted or unsubstituted $C_6$-$C_{30}$-aryl, more preferably substituted or unsubstituted $C_6$-$C_{10}$-aryl, most preferably substituted or unsubstituted phenyl, suitable substituents having been specified above, and/or one of the $R^2$, $R^3$ and $R^4$ radicals and/or one of the $R^5$, $R^6$ and $R^7$ radicals is a radical of the structure (c);

$R^a$, $R^b$ are each independently substituted or unsubstituted $C_1$-$C_{20}$-alkyl, substituted or unsubstituted $C_6$-$C_{30}$-aryl, substituted or unsubstituted heteroaryl having from 5 to 30 ring atoms, or a substituent with donor or acceptor action, suitable and preferred substituents with donor or acceptor action having been specified above;

$R^{14}$, $R^{15}$, $R^{16}$
are each independently substituted or unsubstituted $C_1$-$C_{20}$-alkyl or substituted or unsubstituted $C_6$-$C_{30}$-aryl, preferably substituted or unsubstituted $C_1$-$C_6$-alkyl or substituted or unsubstituted $C_6$-$C_{10}$-aryl, where $R^{14}$, $R^{15}$ and $R^{16}$ are more preferably each independently substituted or unsubstituted $C_1$-$C_{20}$-alkyl or substituted or unsubstituted phenyl; more preferably, at least one of the $R^{14}$, $R^{15}$ and $R^{16}$ radicals is substituted or unsubstituted phenyl; most preferably, at least one of the $R^{14}$, $R^{15}$ and $R^{16}$ radicals is substituted phenyl, suitable substituents having been specified above;

q,r are each independently 0, 1, 2 or 3, where, when q or r is 0, all substitutable positions of the aryl radical bear hydrogen atoms, preferably 0.

In one embodiment, the present invention relates to an inventive organic light-emitting diode in which, in the case that the compound of the general formula (I) is present exclusively in the light-emitting layer or in the light-emitting layer and in the hole conductor layer and the X group is $NR^1$, at least one of the $R^1$ to $R^7$, $R^a$ and $R^b$ radicals in the compounds of the formula (I) comprises at least one heteroatom. Preferred heteroatoms are N, Si, halogen, especially F or Cl, O, S or P. The heteroatom may be present in the form of a substituent on at least one of the $R^1$ to $R^7$, $R^a$ or $R^b$ radicals, or in the form of part of a substituent, or be present in the base structure of at least one of the $R^1$ to $R^7$, $R^a$ or $R^b$ radicals. Suitable substituents or base structures are known to those skilled in the art and are specified under the definitions of the $R^1$ to $R^7$, $R^a$ or $R^b$ radicals.

A preferred embodiment of the present invention relates to an organic light-emitting diode according to the present invention, in which at least one of the $R^2$, $R^3$ and $R^4$ radicals and/or at least one of the $R^5$, $R^6$ and $R^7$ radicals in the compounds of the formula (I) is substituted or unsubstituted $C_6$-$C_{30}$-aryl. Preferred aryl radicals and their substituents have already been specified above.

A further embodiment of the present invention relates to an inventive organic light-emitting diode in which the compound of the general formula (I) is a 3,6-disilyl-substituted compound of the general formula (Ia):

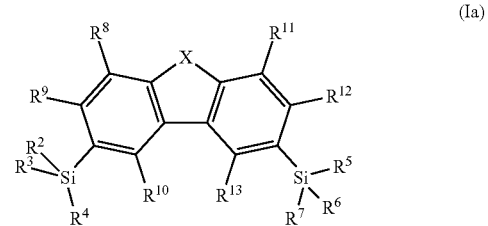

(Ia)

in which:

X is $NR^1$, S, O, $PR^1$, $SO_2$ or SO; preferably $NR^1$, S or O; more preferably $NR^1$;

$R^1$ is substituted or unsubstituted $C_1$-$C_{20}$-alkyl, substituted or unsubstituted $C_6$-$C_{30}$-aryl, or substituted or unsubstituted heteroaryl having from 5 to 30 ring atoms; preferably substituted or unsubstituted $C_6$-$C_{30}$-aryl or substituted or unsubstituted $C_1$-$C_{20}$-alkyl, more preferably substituted or unsubstituted $C_6$-$C_{10}$-aryl or unsubstituted $C_1$-$C_{20}$-alkyl, most preferably substituted or unsubstituted phenyl, suitable substituents having been specified above;

$R^2$, $R^3$, $R^4$, $R^5$, $R^6$, $R^7$
are each independently substituted or unsubstituted $C_1$-$C_{20}$-alkyl or substituted or unsubstituted $C_6$-$C_{30}$-aryl or a structure of the general formula (c);
preferably at least one of the $R^2$, $R^3$ and $R^4$ radicals and/or at least one of the $R^5$, $R^6$ and $R^7$ radicals is substituted or unsubstituted $C_6$-$C_{30}$-aryl, more preferably substituted or unsubstituted $C_6$-$C_{10}$-aryl, most preferably substituted or unsubstituted phenyl, suitable substituents having been specified above, and/or one of the $R^2$, $R^3$ and $R^4$ radicals and/or one of the $R^5$, $R^6$ and $R^7$ radicals is a radical of the structure (c);

$R^8, R^9, R^{10}, R^{11}, R^{12}, R^{13}$
are each independently hydrogen or are as defined for $R^a$ and $R^b$, i.e. are each independently substituted or unsubstituted $C_1$-$C_{20}$-alkyl, substituted or unsubstituted $C_6$-$C_{30}$-aryl, substituted or unsubstituted heteroaryl having from 5 to 30 ring atoms or a substituent with donor or acceptor action, suitable substituents with donor or acceptor action having been specified above; preferably hydrogen, substituted or unsubstituted $C_1$-$C_6$-alkyl, substituted or unsubstituted $C_6$-$C_{10}$-aryl or $SiR^{14}R^{15}R^{16}$; more preferably hydrogen, methyl, ethyl, phenyl, $CF_3$ or $SiR^{14}R^{15}R^{16}$, where $R^{14}$, $R^{15}$ and $R^{16}$ are preferably each independently substituted or unsubstituted $C_1$-$C_{20}$-alkyl or substituted or unsubstituted phenyl; more preferably, at least one of the $R^{14}$, $R^{15}$ and $R^{16}$ radicals is substituted or unsubstituted phenyl; most preferably, at least one of the $R^{14}$, $R^{15}$ and $R^{16}$ radicals is substituted phenyl, suitable substituents having been specified above;

and the further radicals and indices $R^{14}$, $R^{15}$, $R^{16}$ are each as defined above;

where, in the case that the compound of the general formula (I) is present exclusively in the light-emitting layer or in the light-emitting layer and in the hole conductor layer and the group X is $NR^1$, at least one of the $R^1$ to $R^7$, $R^a$ or $R^b$ radicals in the compounds of the formula (I) comprises at least one heteroatom.

In a particularly preferred embodiment, the compounds of the formula (I) used in the inventive organic light-emitting diodes have the following definitions for the $R^1$ to $R^7$, $R^a$ and $R^b$ radicals and the X group:

X is $NR^1$;

$R^1$ is substituted or unsubstituted $C_5$-$C_{30}$-aryl or substituted or unsubstituted heteroaryl having from 5 to 30 ring atoms, preferably substituted or unsubstituted $C_6$-$C_{10}$-aryl, more preferably substituted or unsubstituted phenyl, suitable substituents having been specified above;

$R^2, R^3, R^4, R^5, R^6, R^7$
are each independently substituted or unsubstituted $C_1$-$C_{20}$-alkyl or substituted or unsubstituted $C_6$-$C_{30}$-aryl, or a structure of the general formula (c), preferably each independently substituted or unsubstituted $C_1$-$C_6$-alkyl or substituted or unsubstituted $C_6$-$C_{10}$-aryl, more preferably substituted or unsubstituted $C_1$-$C_6$-alkyl or substituted or unsubstituted phenyl; where, in one embodiment, at least one of the $R^2$, $R^3$ and $R^4$ radicals and/or at least one of the $R^5$, $R^6$ and $R^7$ radicals is substituted or unsubstituted $C_6$-$C_{30}$-aryl, preferably substituted or unsubstituted $C_6$-$C_{10}$-aryl, more preferably substituted or unsubstituted phenyl; preferred substituents having been specified above;

$R^8, R^9, R^{10}, R^{11}, R^{12}, R^{13}$
are each independently hydrogen or are each as defined for $R^a$ and $R^b$, i.e. are each independently substituted or unsubstituted $C_1$-$C_{20}$-alkyl, substituted or unsubstituted $C_6$-$C_{30}$-aryl, substituted or unsubstituted heteroaryl having from 5 to 30 ring atoms or a substituent with donor or acceptor action, suitable substituents with donor or acceptor action already having been specified above; preferably hydrogen, substituted or unsubstituted $C_1$-$C_6$-alkyl, substituted or unsubstituted $C_6$-$C_{10}$-aryl or $SiR^{14}R^{15}R^{16}$; more preferably hydrogen, methyl, ethyl, phenyl, $CF_3$ or $SiR^{14}R^{15}R^{16}$;

$R^{14}, R^{15}, R^{16}$
are each independently substituted or unsubstituted $C_1$-$C_{20}$-alkyl or substituted or unsubstituted $C_6$-$C_{30}$-aryl, preferably substituted or unsubstituted $C_1$-$C_6$-alkyl or substituted or unsubstituted $C_6$-$C_{10}$-aryl, where $R^{14}$, $R^{15}$ and $R^{16}$ are more preferably each independently substituted or unsubstituted $C_1$-$C_{20}$-alkyl, or substituted or unsubstituted phenyl; more preferably, at least one of the $R^{14}$, $R^{15}$ and $R^{16}$ radicals is substituted or unsubstituted phenyl; most preferably, at least one of the $R^{14}$, $R^{15}$ and $R^{16}$ radicals is substituted phenyl, suitable substituents having been specified above;

where, in the case that the compound of the general formula (I) is present exclusively in the light-emitting layer or in the light-emitting layer and in the hole conductor layer, at least one of the $R^1$ to $R^7$, $R^a$ or $R^b$ radicals in the compounds of the formula (I) comprises at least one heteroatom.

Preferred compounds of the formula (I) for use in the inventive OLEDs are detailed below:

i) preferred compounds of the formula (I) in which X is $NR^1$ or $PR^1$ (the preferred carbazole derivatives ($X=NR^1$) are detailed hereinafter). The present invention likewise comprises those compounds in which the N in the formulae below is replaced by $P(X=PR^1)$:

ia) compounds of the formula (I) which are more preferably suitable as a matrix and/or electron/exciton blocker:

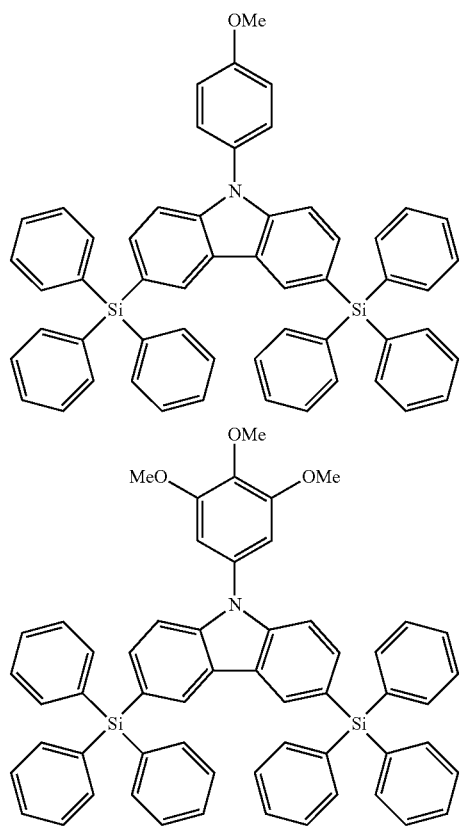

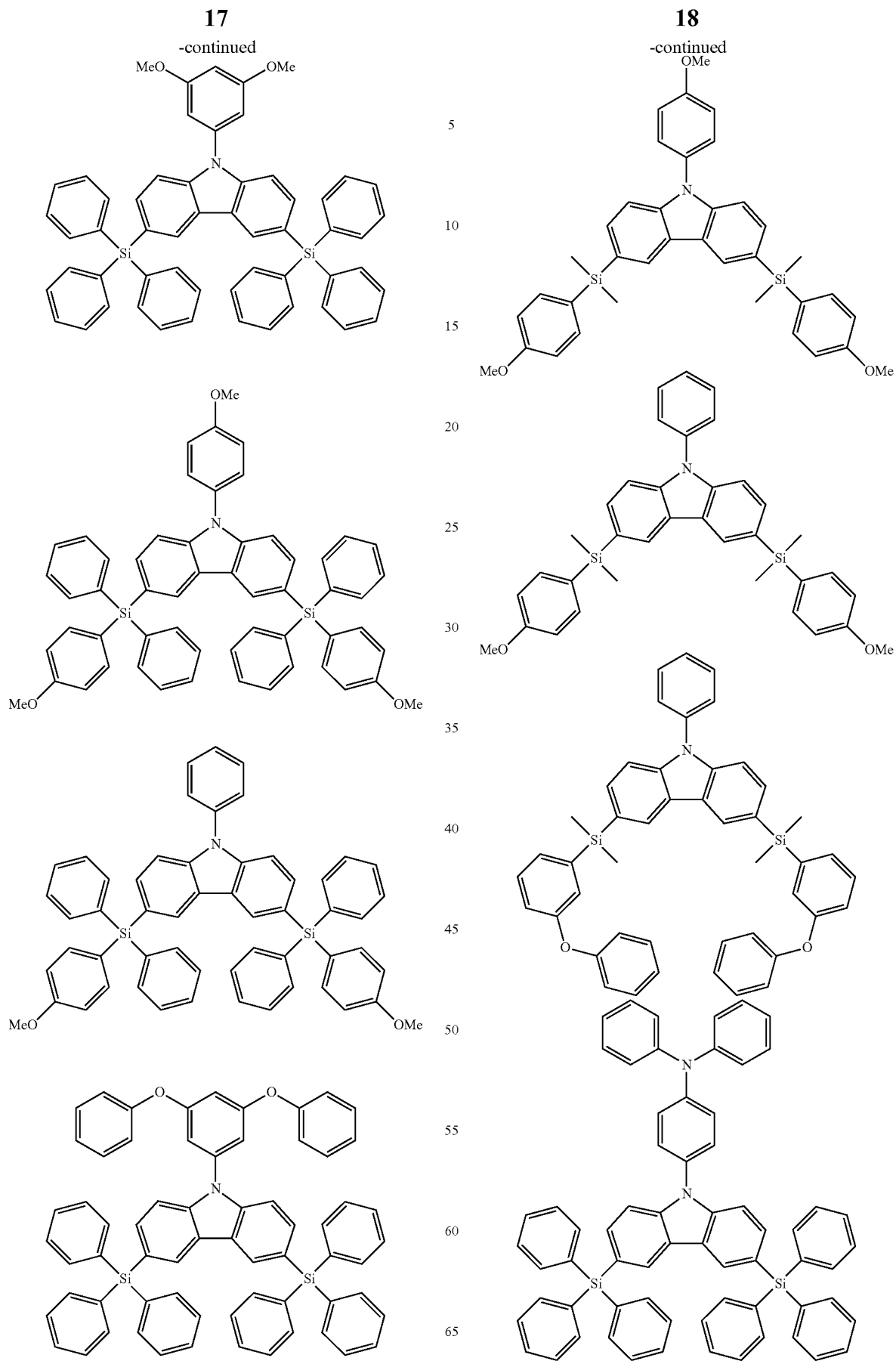

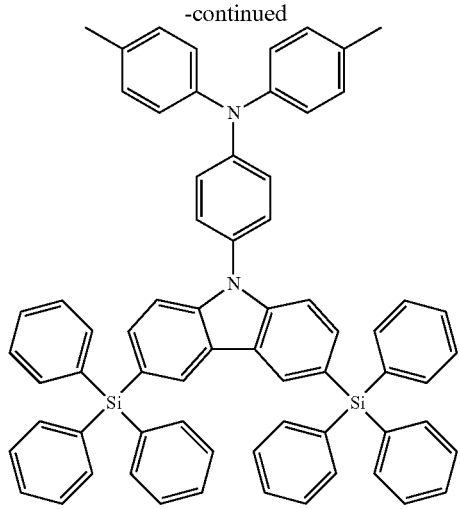
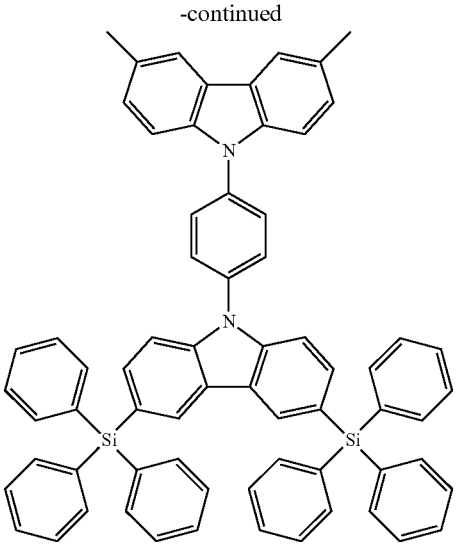
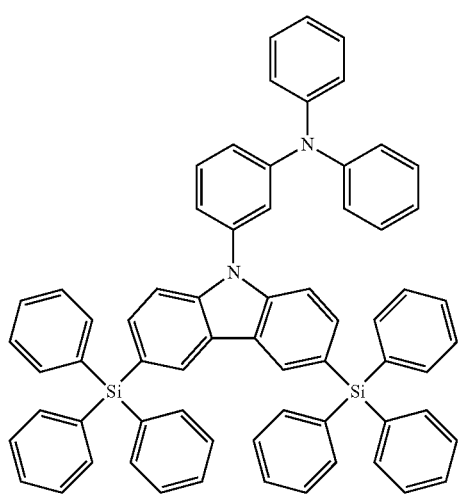
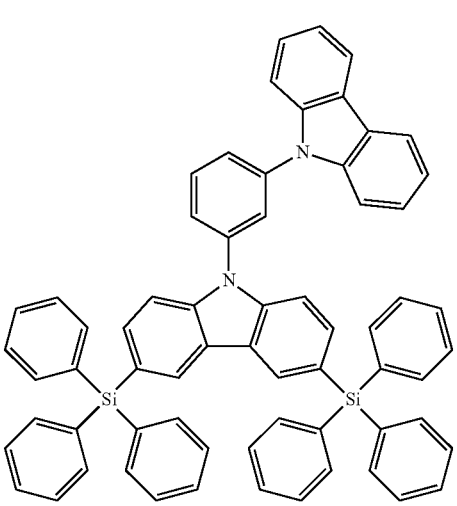
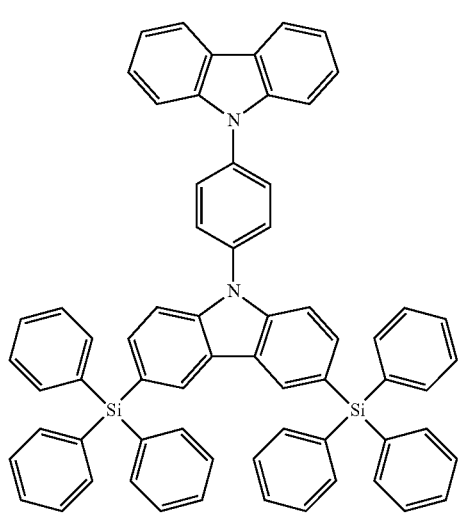
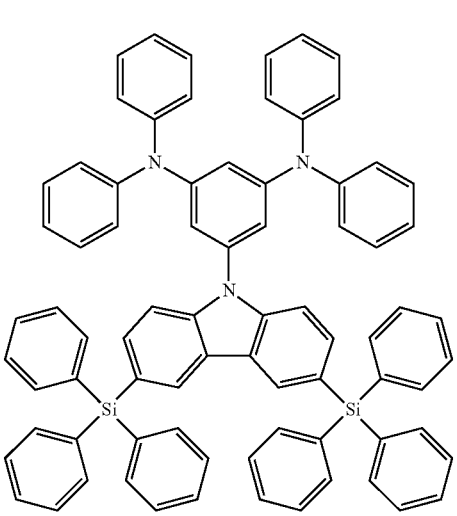

-continued
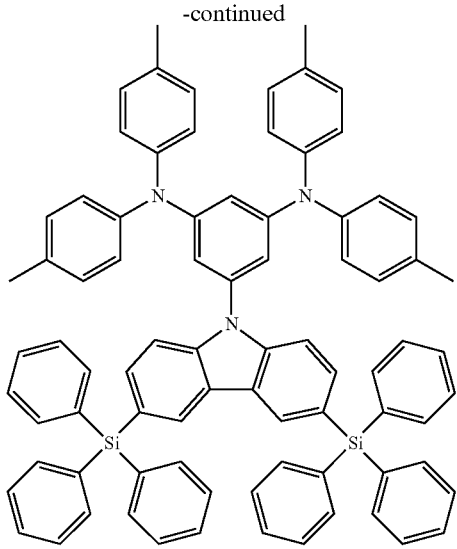
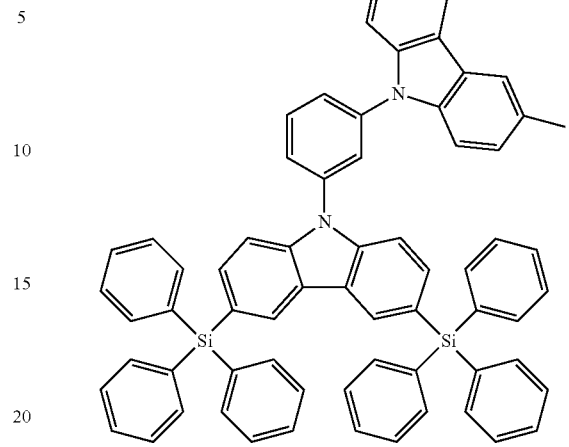
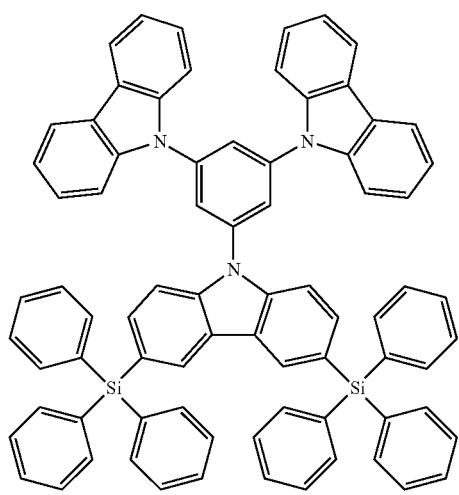
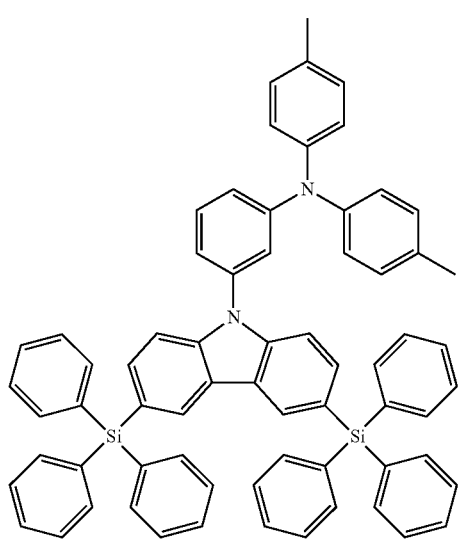
ib) compounds of the formula (I) which are more preferably suitable as a matrix and/or hole/exciton blocker:
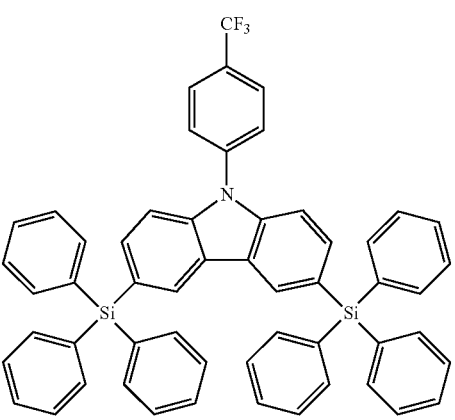

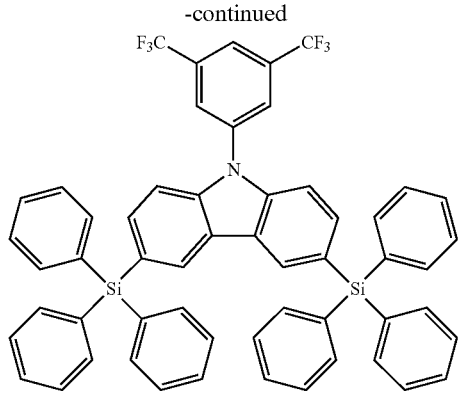
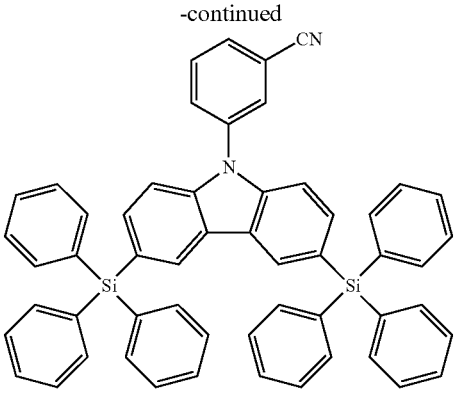
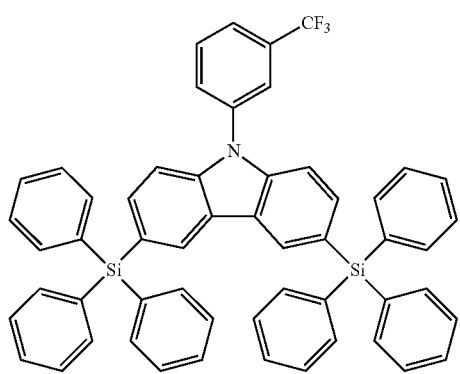
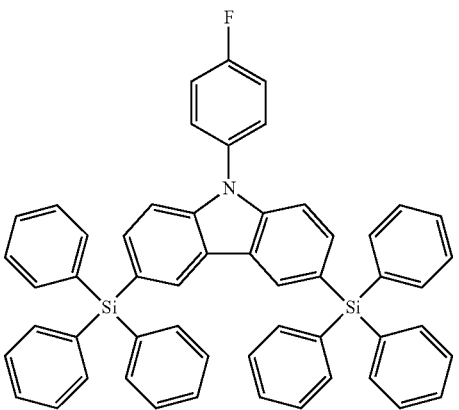
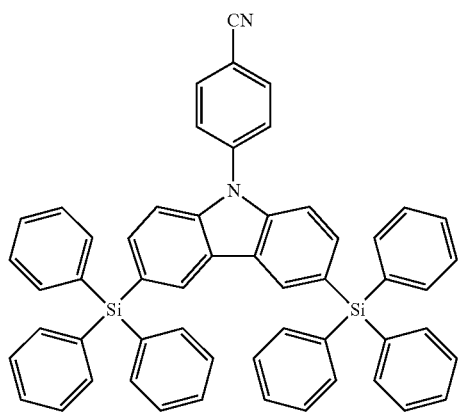
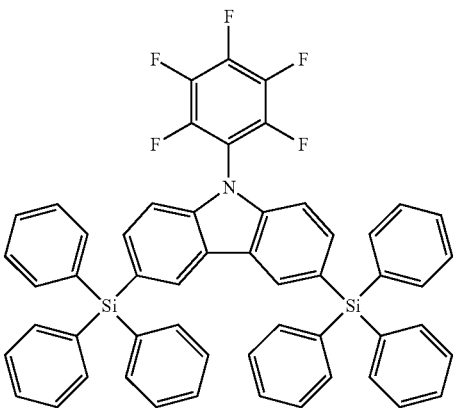
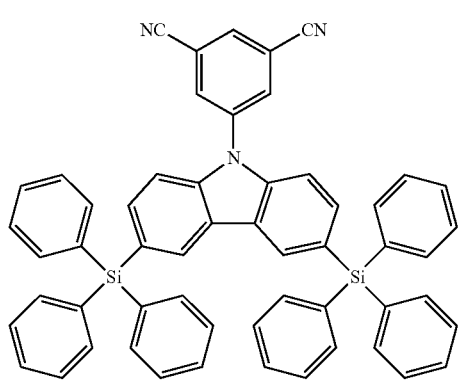
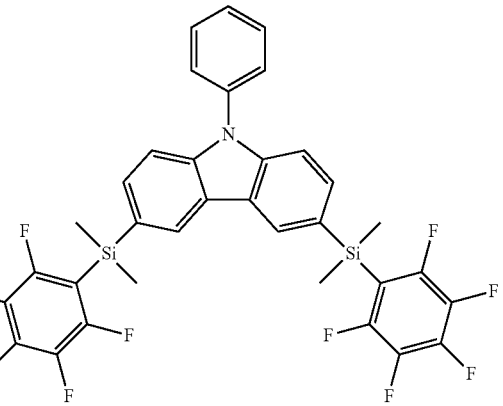

-continued
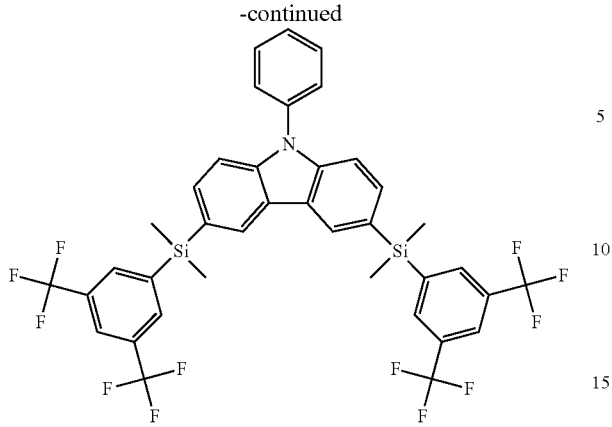
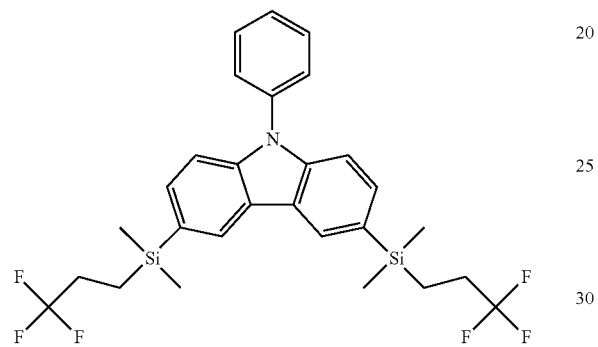
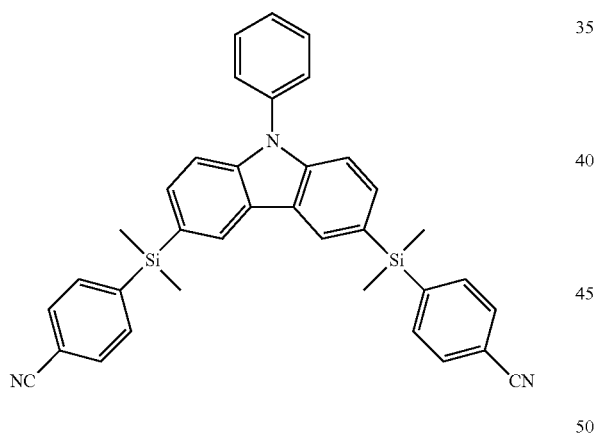
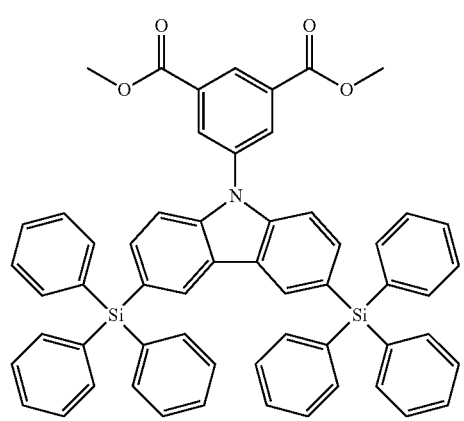
-continued
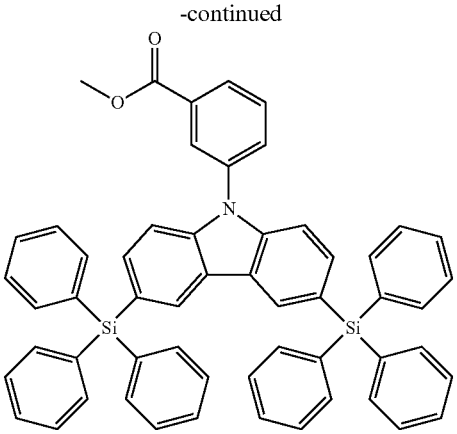
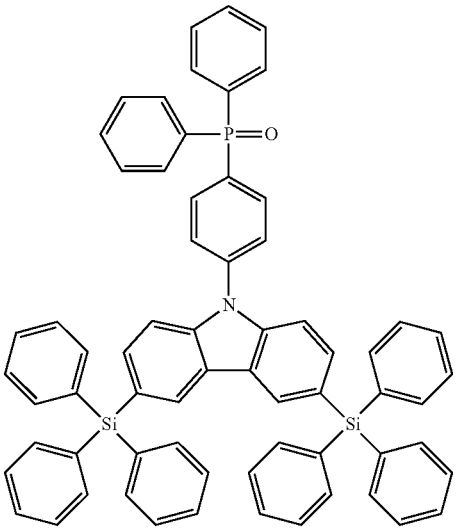
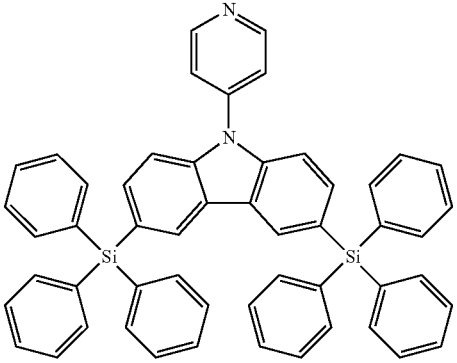
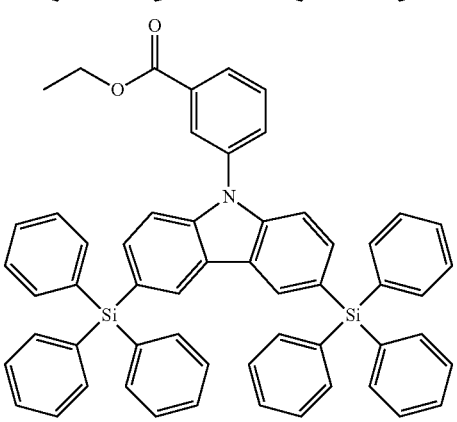

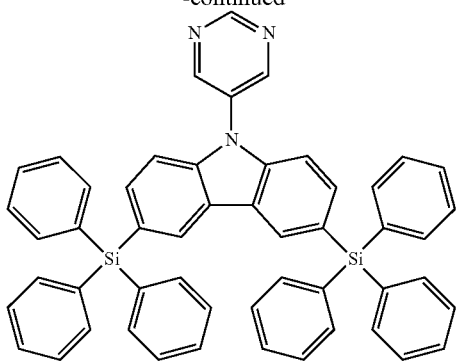
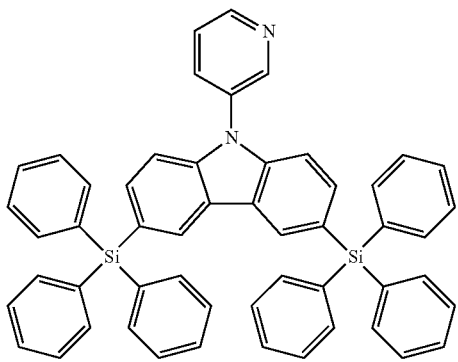
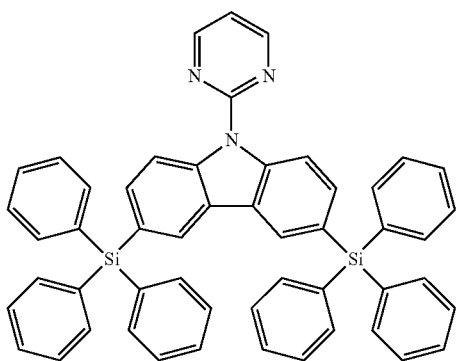
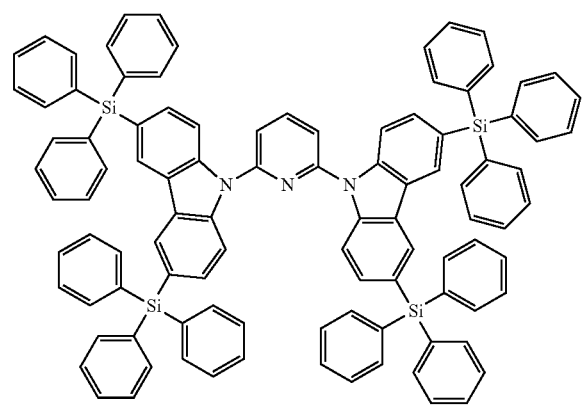
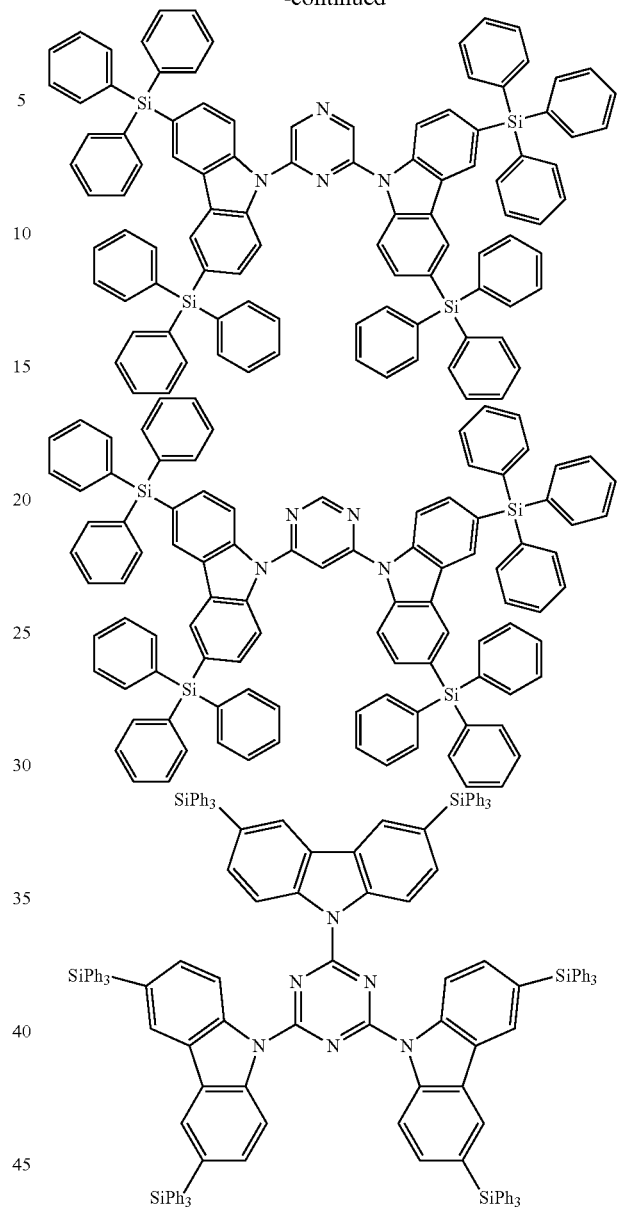
ic) compounds of the formula (I) which are more preferably suitable as a matrix:
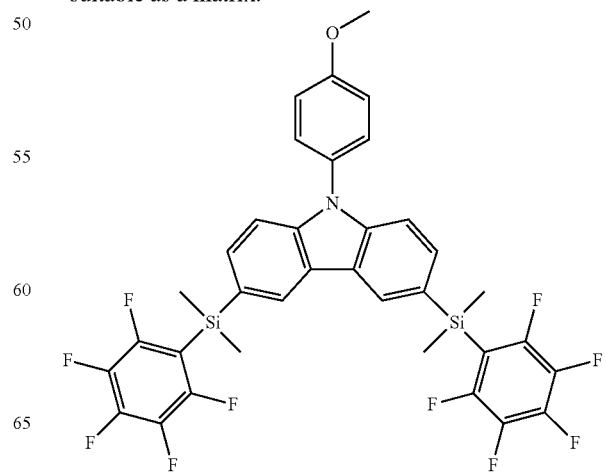

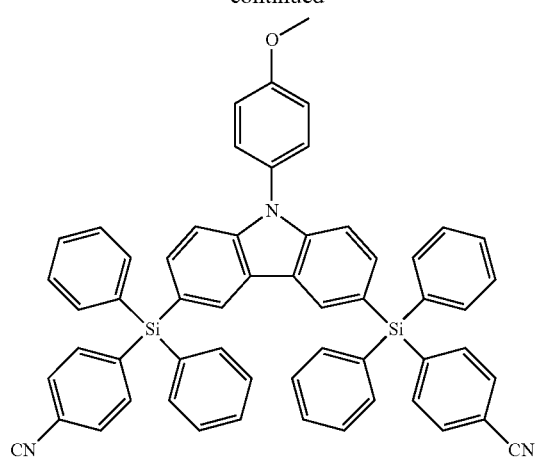
id) further preferred compounds of the formula (I) which are more preferably used suitably as a matrix and/or hole/exciton blocker and/or electron/exciton blocker:
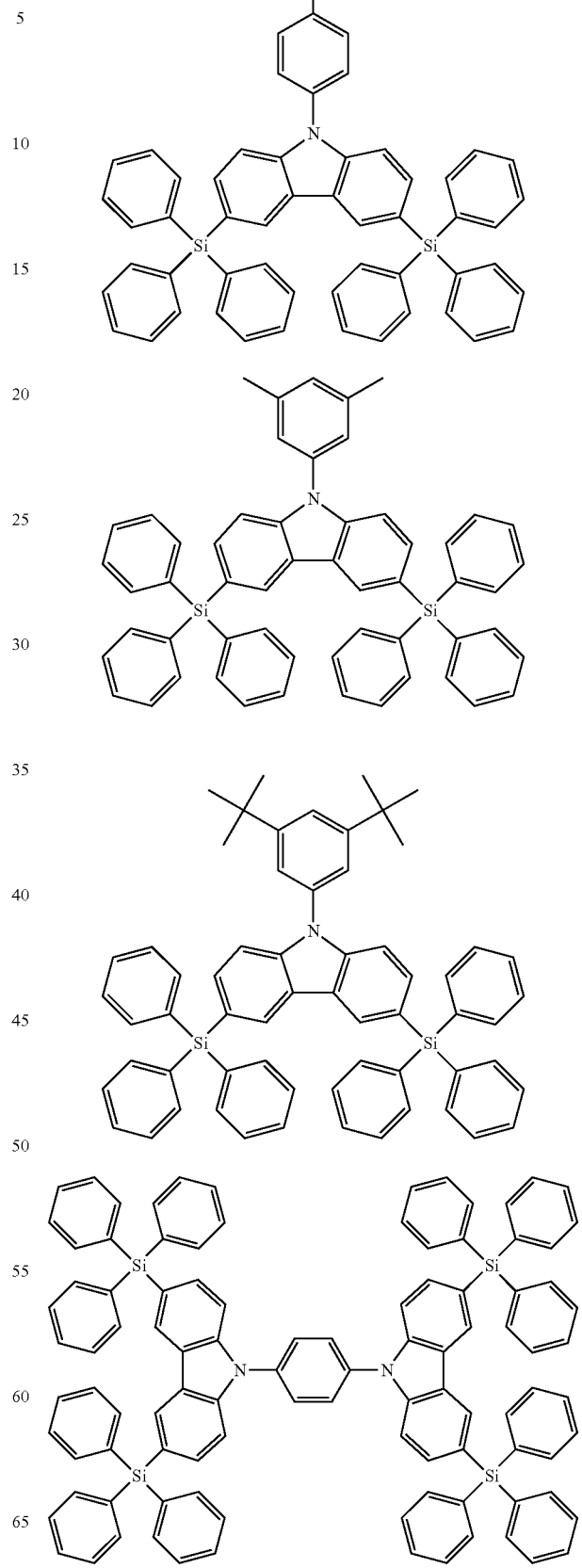

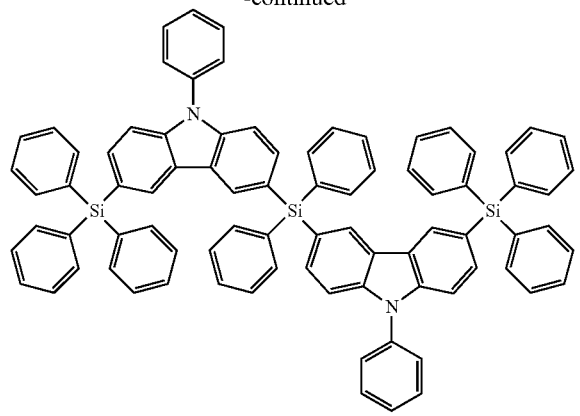
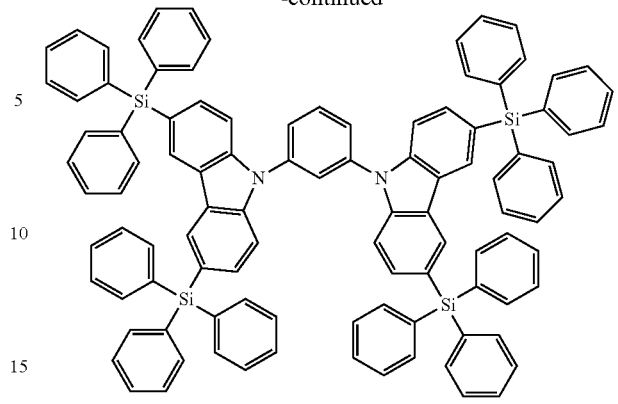
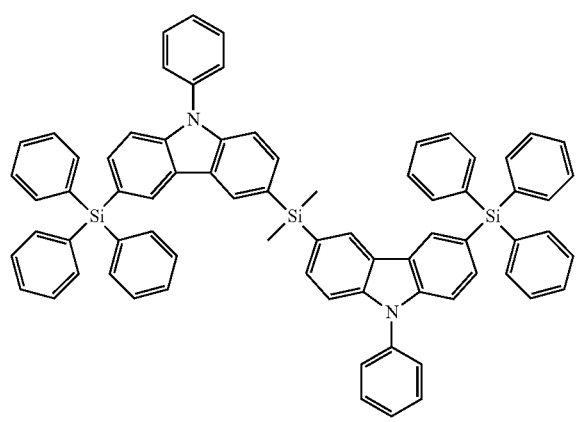
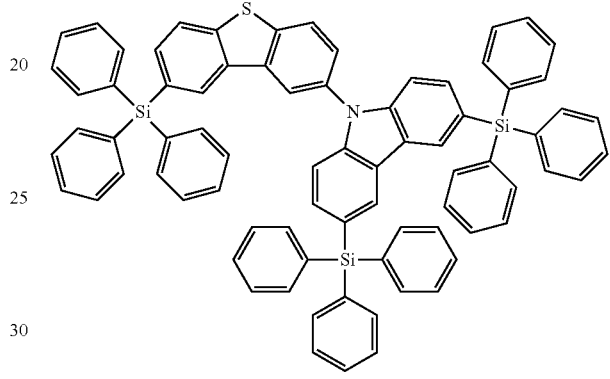
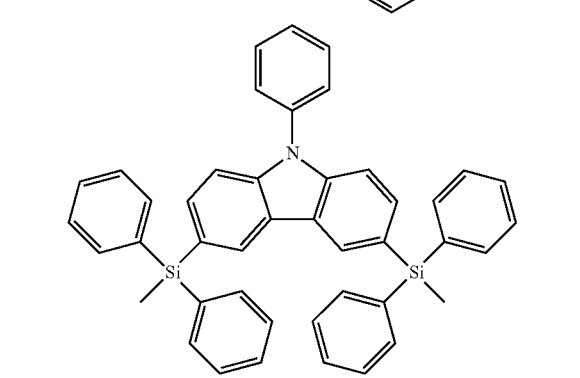
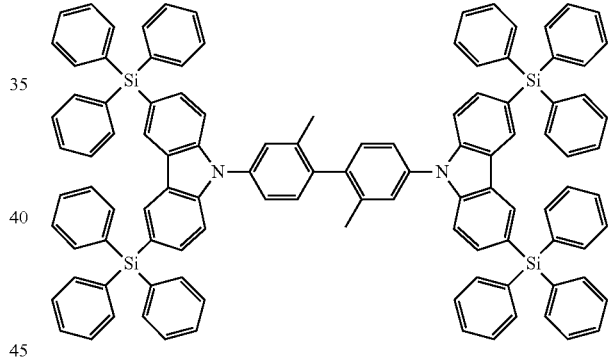
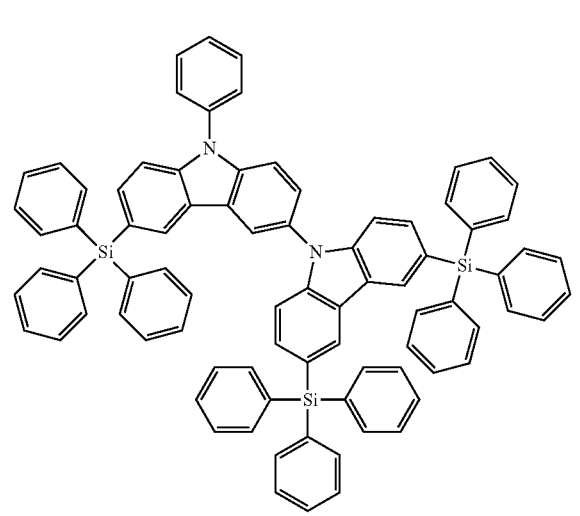
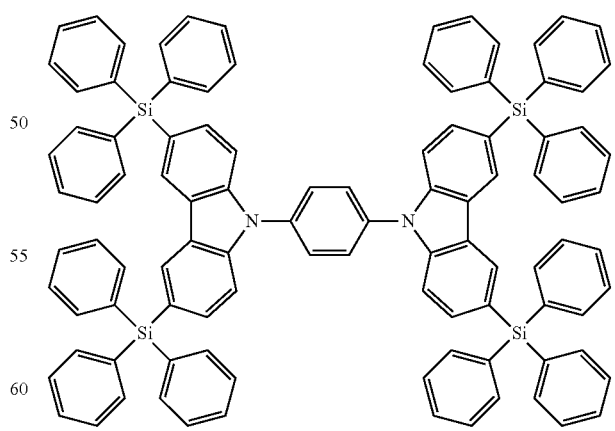
ii) preferred compounds of the formula (I) in which X is O, S, SO, SO$_2$:
iia) compounds of the formula (I) which are more preferably suitable as a matrix and/or electron/exciton blocker:

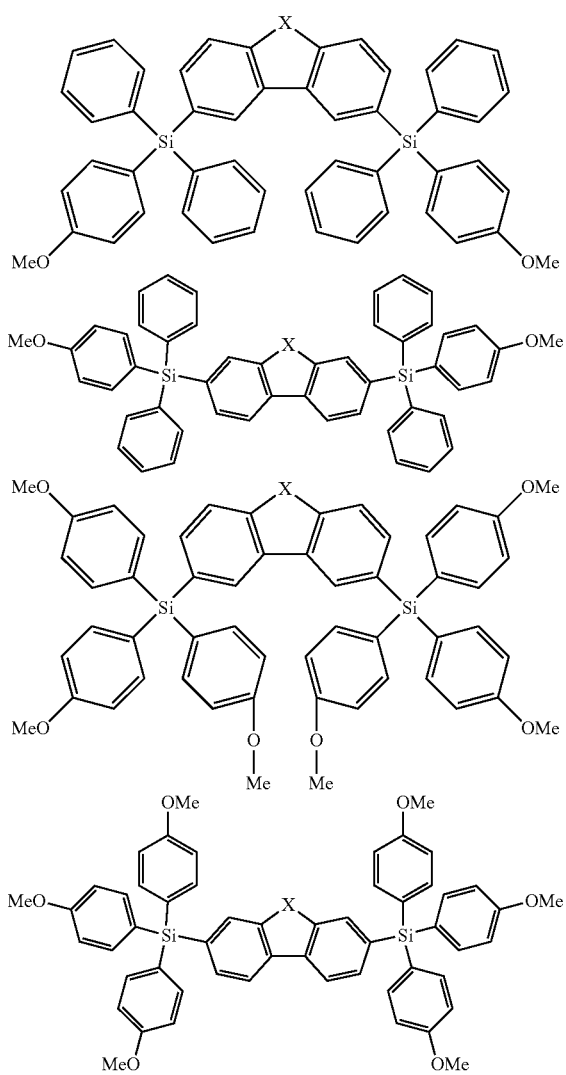
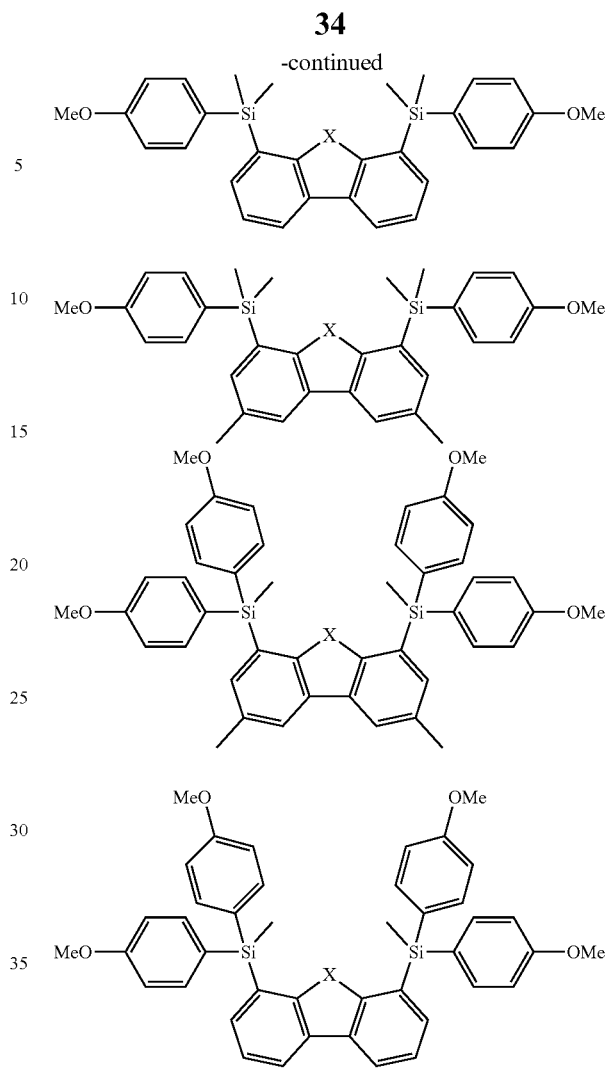
iib) compounds of the formula (I) which are more preferably suitable as a matrix and/or hole/exciton blocker:
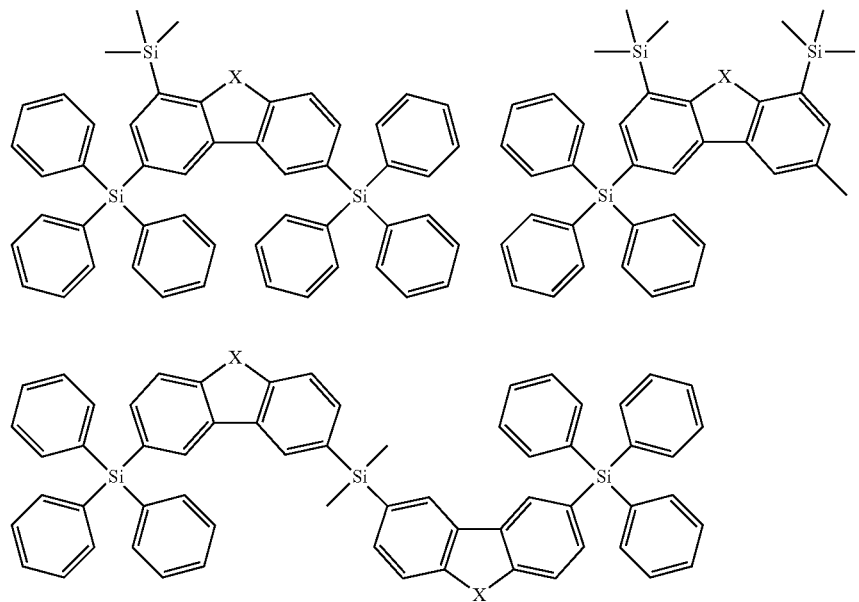

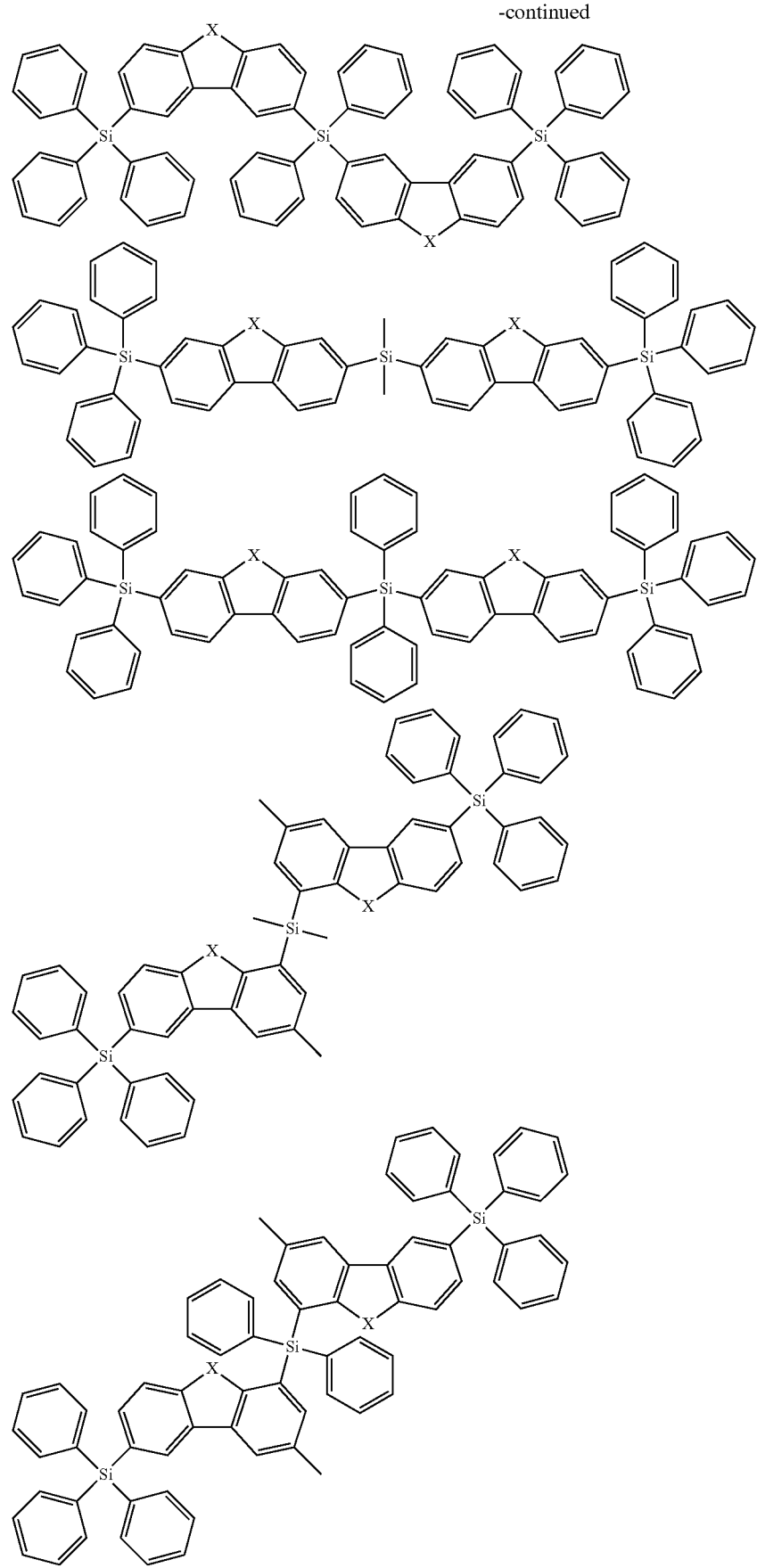

-continued
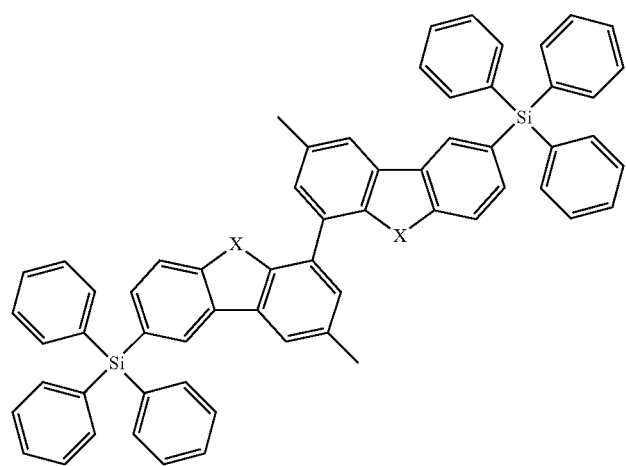
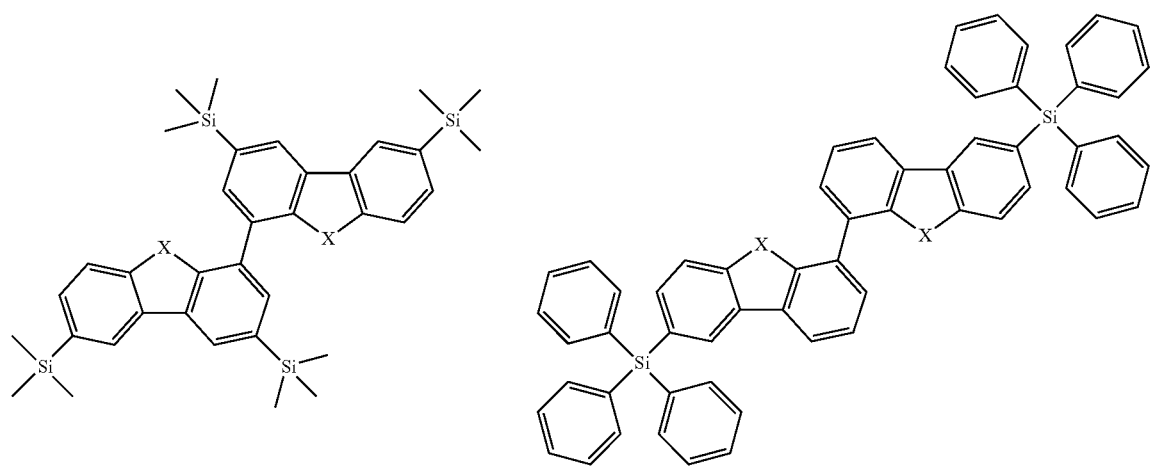
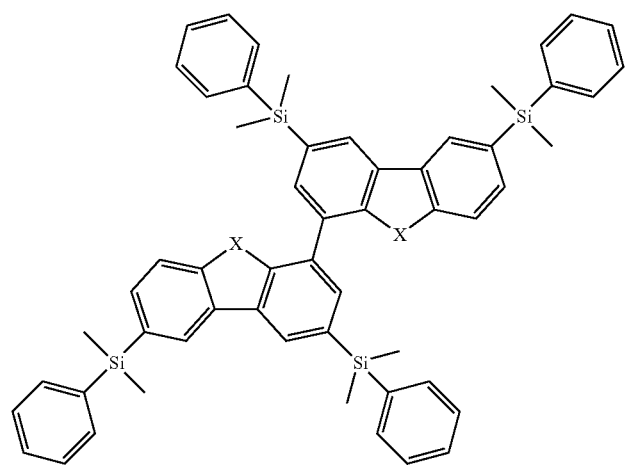

-continued
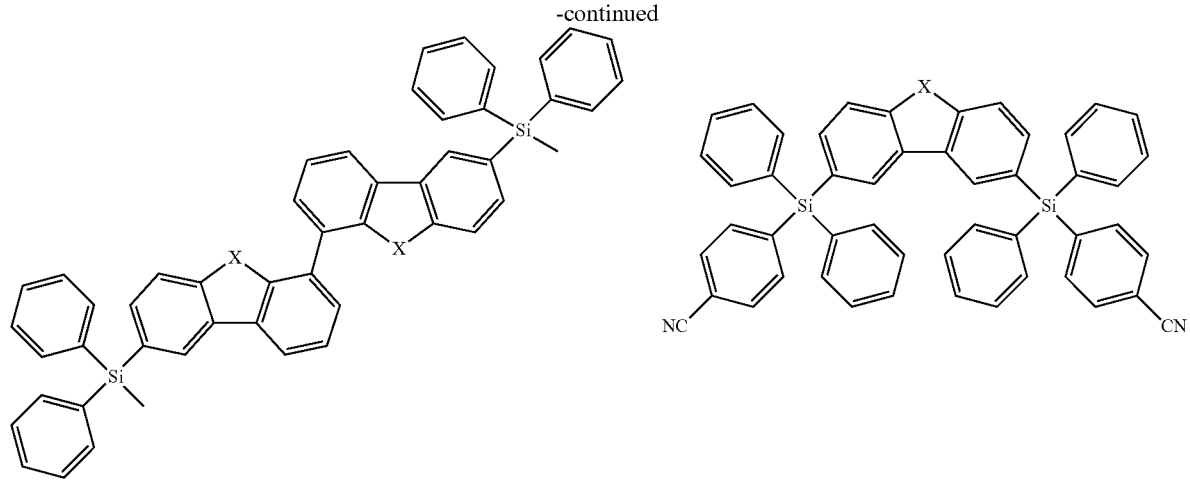
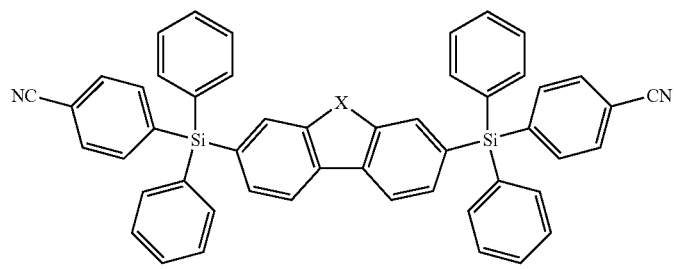
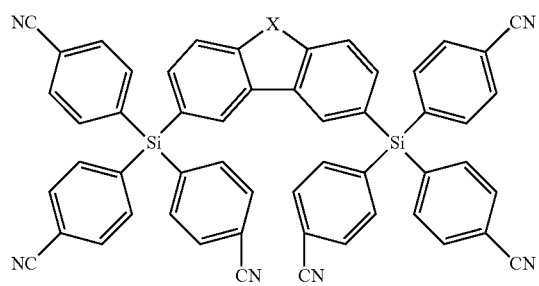
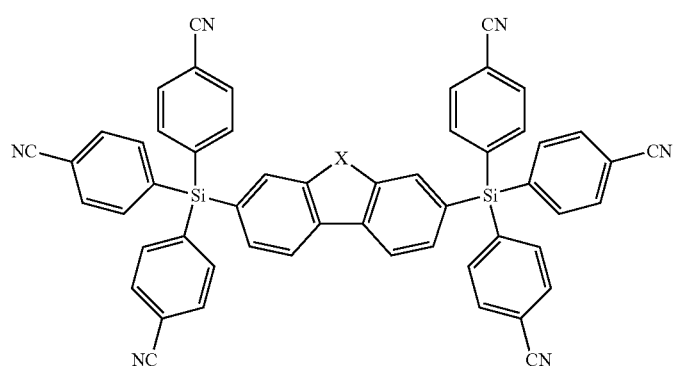
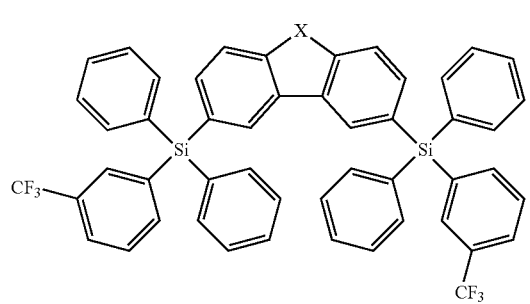

-continued
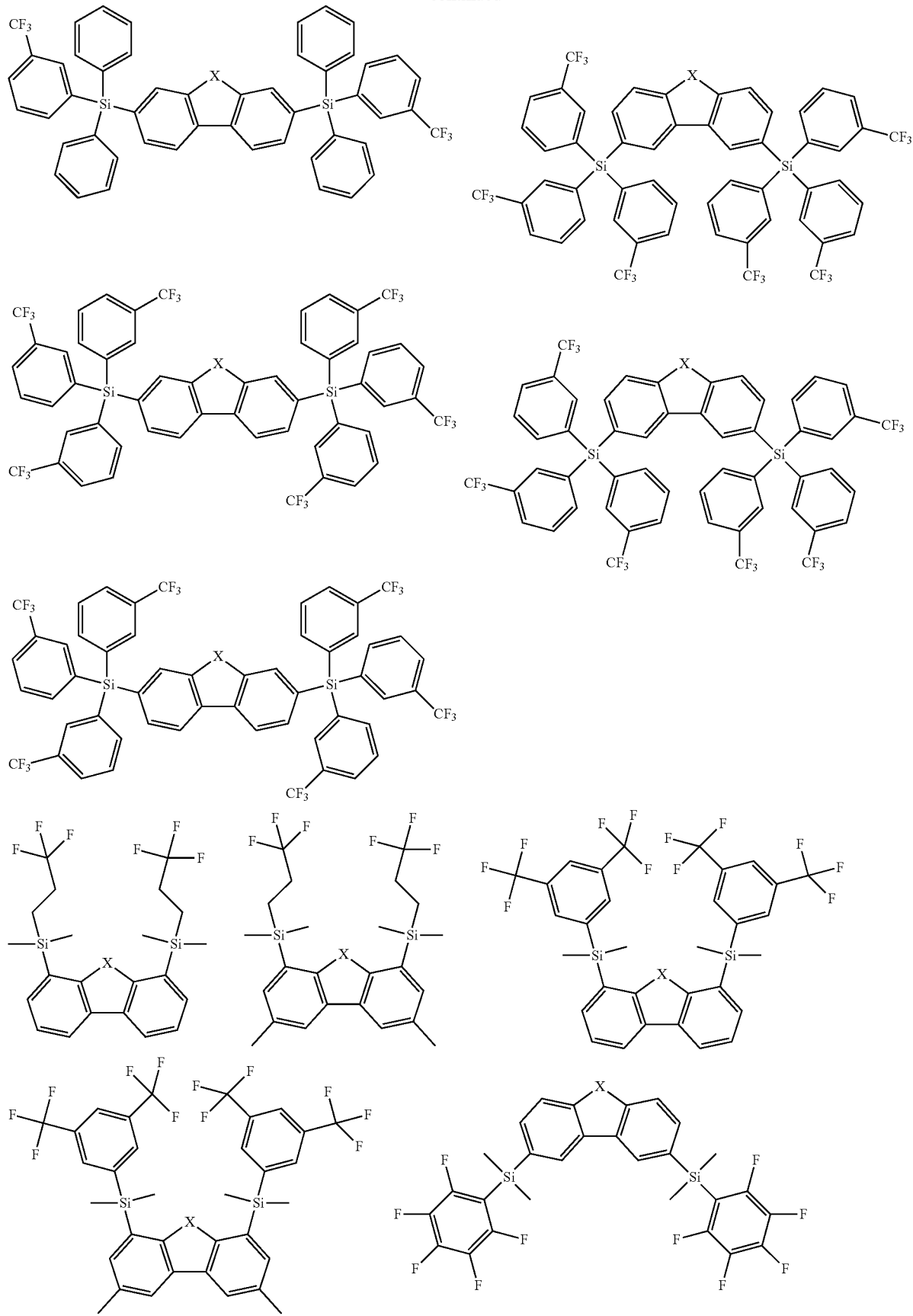

-continued
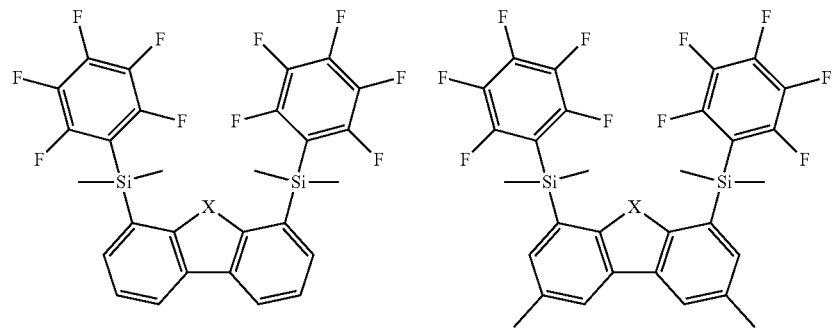
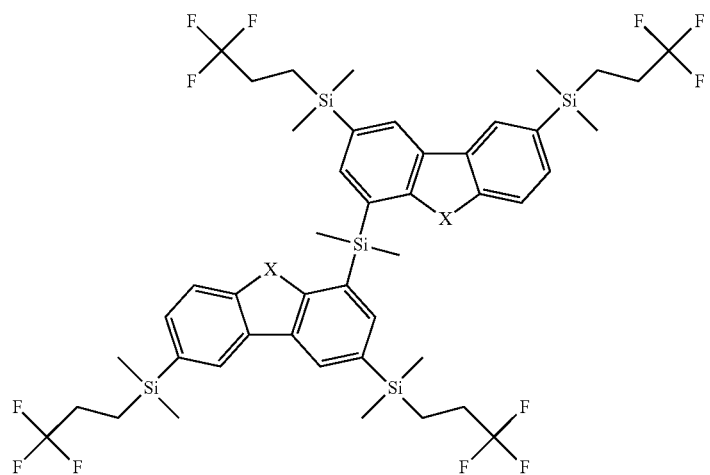
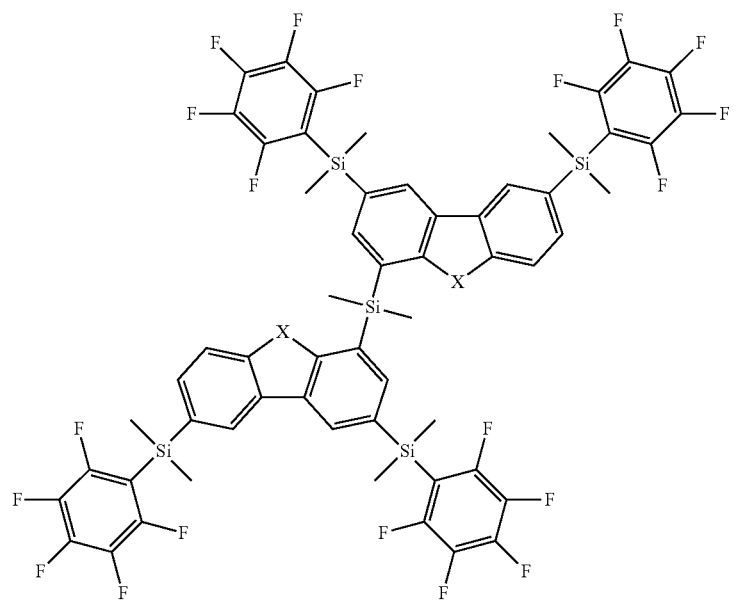

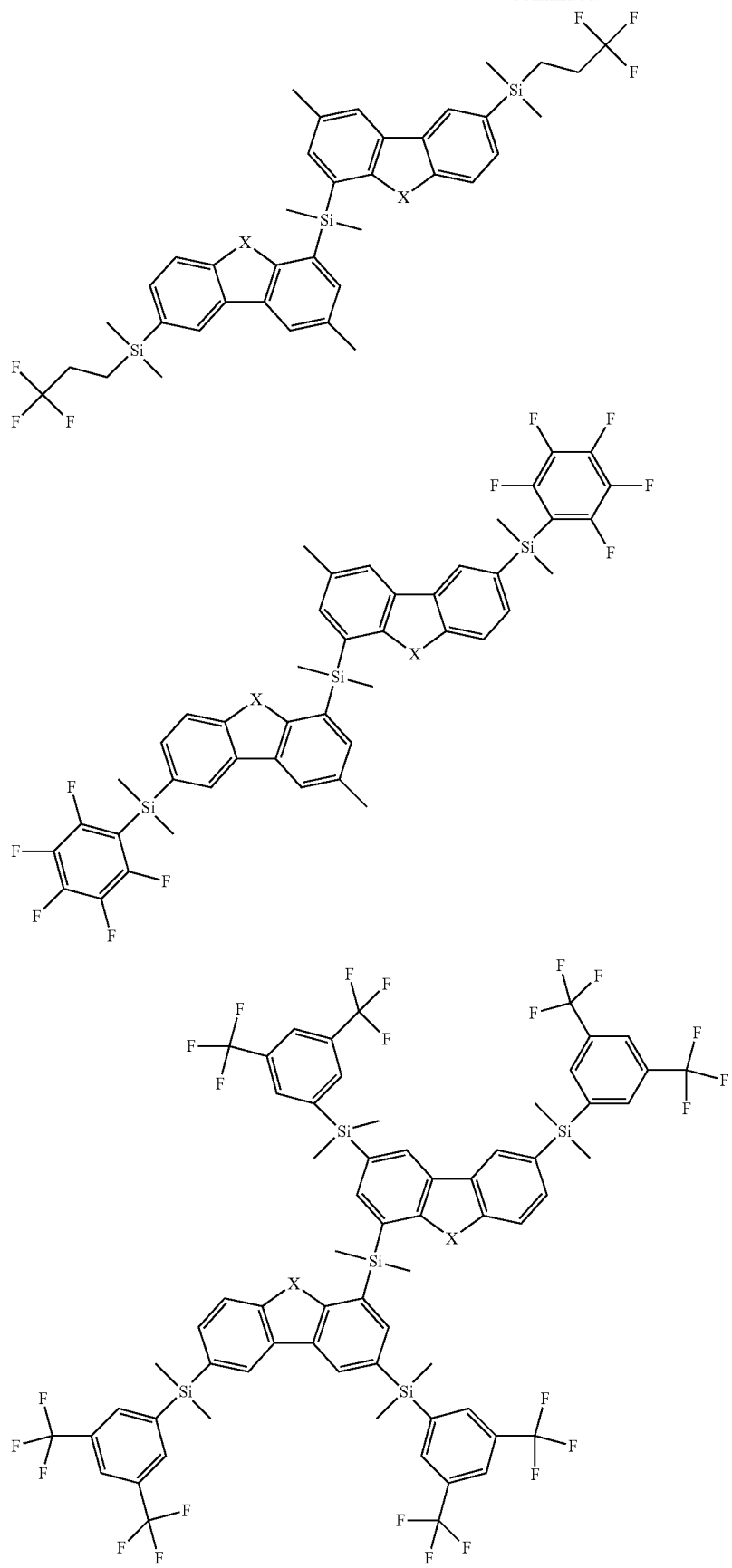

-continued
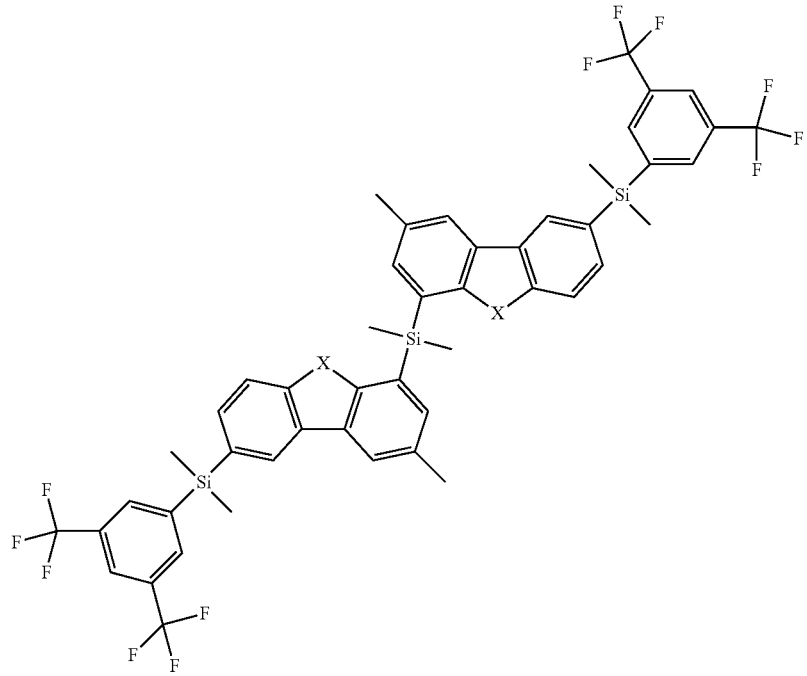
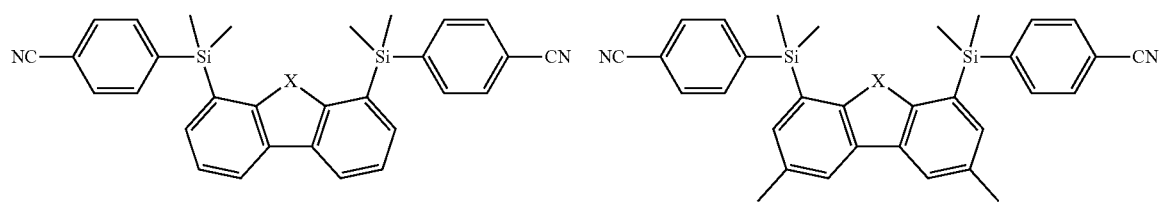
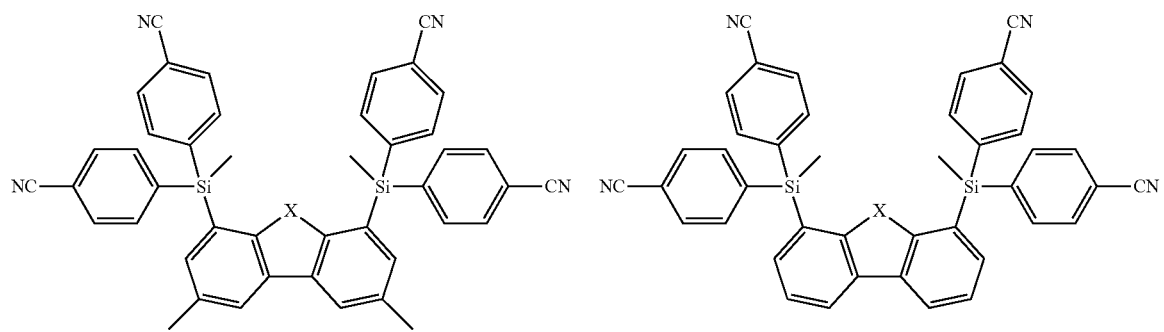
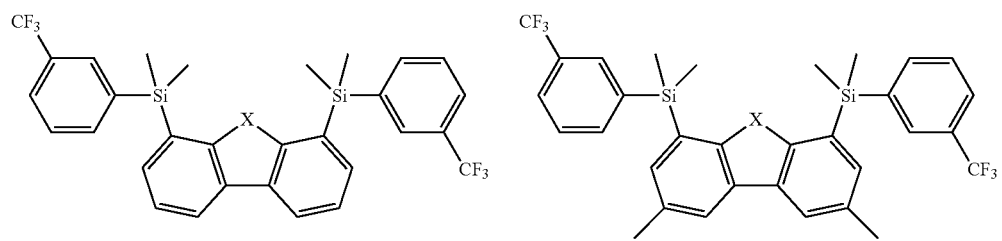

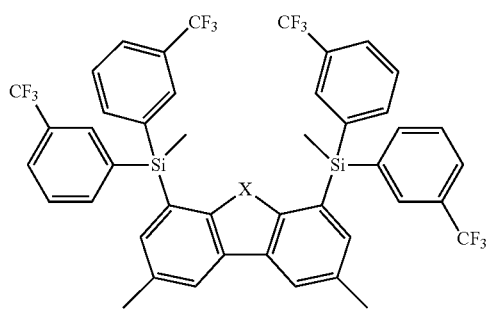
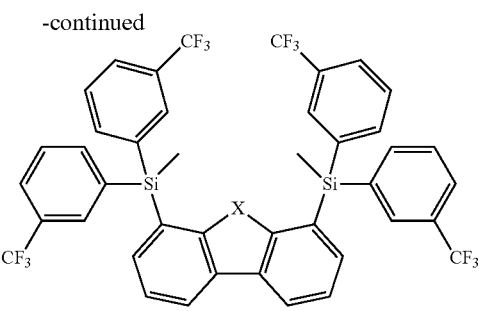

X in the formulae specified under iia) and iib) is preferably O, S, SO or $SO_2$.

In a further preferred embodiment, the present invention relates to an organic light-emitting diode in which a compound of the formula (I) is used, in which the $R^1$ radical and/or at least one of the radicals from the group of $R^2$, $R^3$ and $R^4$ and/or at least one of the radicals from the group of $R^5$, $R^6$ and $R^7$ is independently substituted or unsubstituted $C_6$-aryl of the following formula:

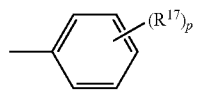

in which
p is 0, 1, 2, 3, 4 or 5, preferably 0, 1, 2 or 3, more preferably 0, 1 or 2;
$R^{17}$ is hydrogen, substituted or unsubstituted $C_1$-$C_{20}$-alkyl, substituted or unsubstituted $C_6$-$C_{30}$-aryl, substituted or unsubstituted heteroaryl having from 5 to 30 ring atoms, a substituent with donor or acceptor action, suitable substituents with donor or acceptor action having been specified above, or a radical of the general formula a or b

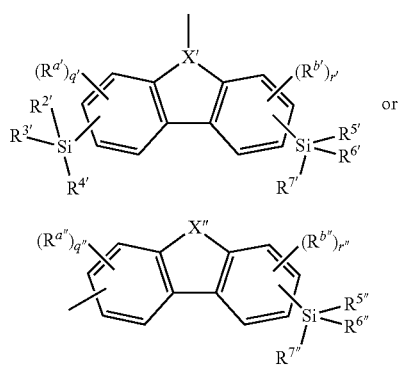

in which
X' is N or P, and
the radicals and indices X", $R^{2'}$, $R^{3'}$, $R^{4'}$, $R^{5'}$, $R^{5''}$, $R^{6'}$, $R^{6''}$, $R^{7'}$, $R^{7''}$, $R^{a'}$, $R^{a''}$, $R^{b'}$, $R^{b''}$, q', q", r' and r" are each independently as defined for the radicals and indices X, $R^2$, $R^3$, $R^4$, $R^5$, $R^6$, $R^7$, $R^a$, $R^b$, q and r;
or
one of the $R^2$, $R^3$ and $R^4$ radicals and/or one of the $R^5$, $R^6$ and $R^7$ radicals is a radical of the general formula c

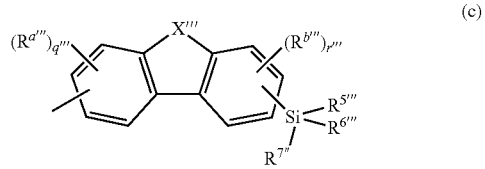

in which the radicals and indices X''', $R^{5'''}$, $R^{6'''}$, $R^{7'''}$, $R^{a'''}$, $R^{b'''}$, q''' and r''' are each independently as defined for the radicals and indices X, $R^5$, $R^6$, $R^7$, $R^a$, $R^b$, q and r.

Preferred $R^{17}$ radicals are selected from the group consisting of hydrogen, substituted or unsubstituted $C_1$-$C_6$-alkyl, substituted or unsubstituted $C_6$-$C_{10}$-aryl, substituted or unsubstituted heteroaryl having from 5 to 13 ring atoms, preferably carbazolyl, a substituent with donor or acceptor action selected from the group consisting of $C_1$- to $C_{20}$-alkoxy, preferably $C_1$-$C_6$-alkoxy, more preferably ethoxy or methoxy; $C_6$-$C_{30}$-aryloxy, preferably $C_6$-$C_{10}$-aryloxy, more preferably phenyloxy; $SiR^{14}R^{15}R^{16}$; halogen radicals, preferably F, Cl, Br, more preferably F or Cl, most preferably F, halogenated $C_1$-$C_{20}$-alkyl radicals, preferably halogenated $C_1$-$C_6$-alkyl radicals, most preferably fluorinated $C_1$-$C_6$-alkyl radicals, e.g. $CF_3$, $CH_2F$, $CHF_2$ or $C_2F_5$; amino, preferably dimethylamino, diethylamino or diphenylamino, more preferably diphenylamino; OH, pseudohalogen radicals, preferably CN, SCN or OCN, more preferably CN; C(O)$OC_1$-$C_4$-alkyl, preferably —C(O)OMe, P(O)Ph$_2$, $SO_2$Ph, where $R^{14}$, $R^{15}$ and $R^{16}$ are each independently substituted or unsubstituted $C_1$- to $C_6$-alkyl or substituted or unsubstituted $C_6$- to $C_{10}$-aryl and—in the case of $SiR^{14}R^{15}R^{16}$—are preferably each independently substituted or unsubstituted $C_1$-$C_{20}$-alkyl or substituted or unsubstituted phenyl; more preferably, at least one of the $R^{14}$, $R^{15}$ and $R^{16}$ radicals is substituted or unsubstituted phenyl; most preferably, at least one of the $R^{14}$, $R^{15}$ and $R^{16}$ radicals is substituted phenyl, suitable substituents having been specified above. More preferably, the $R^{17}$ radicals are each independently selected from the group consisting of methoxy, phenyloxy, unsubstituted $C_1$-$C_4$-alkyl, preferably methyl, halogenated $C_1$-$C_4$-alkyl, preferably $CF_3$, $CHF_2$, $CH_2F$, $C_2F_6$, CN, halogen, preferably F, —C(O)O—$C_1$-$C_4$-alkyl, preferably —C(O)OMe, P(O)Ph$_2$, and substituted or unsubstituted heteroaryl having from 5 to 13 ring atoms, preferably carbazolyl, where, in the case that the compound of the general formula (I) is present exclusively in the light-emitting layer or in the light-emitting layer and in the hole conductor layer and the X group is $NR^1$, at least one of the $R^1$ to $R^7$, $R^a$ or $R^b$ radicals in the compounds of the formula (I) comprises at least one heteroatom.

In a further embodiment of the present invention, the indices r and q in the compounds of the formula (I) are each 0, i.e.

all substitutable positions of the aryl groups bear hydrogen atoms. For all other radicals and indices, the aforementioned definitions apply.

The compounds of the formula (I) used in accordance with the invention may be used in different layers of the inventive organic light-emitting diode, suitable and preferred layer sequences in the inventive OLEDs having been specified above.

In one embodiment, the present invention relates to organic light-emitting diodes in which the compounds of the formula (I) are used as a matrix in the light-emitting layer E, where, in the case that the compound of the general formula (I) is present exclusively in the light-emitting layer or in the light-emitting layer and in the hole conductor layer and the X group is $NR^1$, at least one of the $R^1$ to $R^7$, $R^a$ or $R^b$ radicals in the compounds of the formula (I) comprises at least one heteroatom.

In a further embodiment, the present invention relates to an inventive organic light-emitting diode in which the compounds of the formula (I) are used in the blocking layer for electrons as an electron/exciton blocker and/or in the hole injection layer and/or in the hole conductor layer, where, in the case that the compound of the general formula (I) is present exclusively in the light-emitting layer or in the light-emitting layer and in the hole conductor layer and the X group is $NR^1$, at least one of the $R^1$ to $R^7$, $R^a$ or $R^b$ radicals in the compounds of the formula (I) comprises at least one heteroatom. It is likewise possible that the compounds of the formula (I) are additionally present in the light-emitting layer E and/or one or more of the layers specified below.

In a further embodiment, the present invention relates to an inventive organic light-emitting diode in which the compounds of the formula (I) are used in the blocking layer for holes as a hole/exciton blocker and/or in the electron injection layer and/or in the electron conductor layer. It is likewise possible that the compounds of the formula (I) are additionally present in the light-emitting layer E and/or one or more of the aforementioned layers.

Depending on the layer in which the compounds of the formula (I) are used, the compounds of the formula (I) have different preferred $R^2$, $R^3$, $R^4$, $R^5$, $R^6$, $R^7$, $R^a$ and $R^b$ radicals and different X groups. In addition to the function of the layer in which the compounds of the formula (I) can be used in the inventive OLED, the $R^1$ to $R^7$, $R^a$ and $R^b$ radicals and the X group of the compounds of the formula (I) are additionally dependent on the electronic properties (relative positions of the HOMOs and LUMOs) of the particular layers used in the inventive OLED. It is thus possible, by virtue of suitable substitution of the compounds of the formula (I), to adjust the HOMO and LUMO orbital positions to the further layers used in the inventive OLED, and thus to achieve a high stability of the OLED and hence a long operative lifetime and good efficiencies.

The principles regarding the relative positions of HOMO and LUMO in the individual layers of an OLED are known to those skilled in the art. The principles, by way of example with regard to the properties of the blocking layer for electrons and of the blocking layer for holes, in relation to the light-emitting layer are detailed hereinafter:

The LUMO of the blocking layer for electrons is energetically higher than the LUMO of the materials used in the light-emitting layer (both of the emitter material and of any matrix materials used). The greater the energetic difference of the LUMOs of the blocking layer for electrons and of the materials in the light-emitting layer, the better are the electron- and/or exciton-blocking properties of the blocking layer for electrons. Suitable substitution patterns of the compounds of the formula (I) suitable as electron and/or exciton blocker materials thus depend upon factors including the electronic properties (especially the position of the LUMO) of the materials used in the light-emitting layer.

The HOMO of the blocking layer for electrons is energetically higher than the HOMOs of the materials present in the light-emitting layer (both of the emitter materials and of any matrix materials present). The greater the energetic difference of the HOMOs of the blocking layer for holes and of the materials present in the light-emitting layer, the better are the hole- and/or exciton-blocking properties of the blocking layer for holes. Suitable substitution patterns of the compounds of the formula (I) suitable as hole and/or exciton blocker materials thus depend upon factors including the electronic properties (especially the position of the HOMOs) of the materials present in the light-emitting layer.

Comparable considerations relating to the relative position of the HOMOs and LUMOs of the different layers used in the inventive OLED apply to the further layers which may be used in the OLED and are known to those skilled in the art.

Preferably suitable $R^1$, $R^2$, $R^3$, $R^4$, $R^5$, $R^6$, $R^7$, $R^a$ and $R^b$ radicals of the compounds of the formula (I), depending on their use in different layers of the inventive OLED, are specified below. It is pointed out that preferred substitutions of the compounds of the formula (I) other than those specified below may in principle be suitable for use in the different layers—depending on the electronic properties of the further layers of the OLED, especially depending on the electronic properties of the light-emitting layer.

Compounds of the General Formula (I) which are Especially Suitable for Use in the Light-emitting Layer E as Matrix Materials, and for Use in the Blocking Layer for Electrons, in the Hole Injection Layer and/or in the Hole Conductor Layer A preferred embodiment of the present invention relates to an organic light-emitting diode in which the compounds of the formula (I) are used in a blocking layer for electrons, in a hole injection layer and/or in a hole conductor layer and/or in the light-emitting layer E as matrix materials.

Preferred compounds of the formula (I) which can be used in at least one of the aforementioned layers have at least one $R^1$, $R^2$, $R^3$, $R^4$, $R^5$, $R^6$ or $R^7$ radical which is substituted or unsubstituted $C_1$-$C_{20}$-alkyl, heteroaryl having from 5 to 30 ring atoms, $C_6$-$C_{30}$-aryl substituted by at least one substituent with donor action, or $C_6$-$C_{30}$-aryl substituted by heteroaryl having from 5 to 30 ring atoms, or a substituent with donor action or, in the case of $R^2$, $R^3$, $R^4$, $R^5$, $R^6$ or $R^7$, hydrogen, where, in the case that the compound of the general formula (I) is present exclusively in the light-emitting layer or in the light-emitting layer and in the hole conductor layer and the X group is $NR^1$, at least one of the $R^1$ to $R^7$, $R^a$ or $R^b$ radicals in the compounds of the formula (I) comprises at least one heteroatom.

Suitable substituents with donor action (electron-donating radicals) are selected from the group consisting of substituted and unsubstituted $C_1$-$C_6$-alkyl, preferably methyl, substituted and unsubstituted $C_6$-$C_{10}$-aryl, substituted and unsubstituted electron-rich heteroaryl having from five to 30 ring atoms, preferably selected from the group consisting of carbazolyl, pyrrolyl, imidazolyl, pyrazolyl, triazolyl, oxazolyl, thiophenyl, preferably carbazolyl, pyrrolyl and thiophenyl, more preferably carbazolyl, $C_1$-$C_{20}$-alkoxy, preferably $C_1$-$C_6$-alkoxy, more preferably methoxy and ethoxy, $C_6$-$C_{30}$-aryloxy, preferably $C_6$-$C_{10}$-aryloxy, more preferably phenyloxy, $C_1$-$C_{20}$-alkylthio, preferably $C_1$-$C_6$-alkylthio, more preferably —$SCH_3$, $C_6$-$C_{30}$-arylthio, preferably $C_6$-$C_{10}$-arylthio, more preferably —SPh, F, $SiR^{14}R^{15}R^{16}$ where $R^{14}$, $R^{15}$ and $R^{16}$ are preferably donor-substituted phenyl groups, amino (—NR$^{14}$R$^{15}$), preferably diphenylamino, phosphine (PR$^{14}$R$^{15}$) hydrazine radicals, OH, donor-substituted vinyl groups, where R$^{14}$, R$^{15}$ and R$^{16}$ are each as defined above and are preferably donor-substituted phenyl groups.

Very particularly preferred substituents with donor action are selected from the group consisting of diphenylamino, carbazolyl, methoxy, phenoxy, very particular preference being given especially to methoxy and carbazolyl.

More preferably, the at least one radical which is used in the aforementioned layers is a C$_6$-aryl radical of the formula (d) substituted by at least one substituent with donor action and/ or at least one heteroaryl radical having from 5 to 30 ring atoms

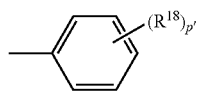

(d)

in which:
p' is 1, 2, 3, 4 or 5, preferably 1, 2 or 3, more preferably 1 or 2, and
R$^{18}$ is in each case independently substituted or unsubstituted C$_1$-C$_6$alkyl, preferably methyl, substituted or unsubstituted C$_6$-C$_{10}$-aryl, C$_1$-C$_{20}$-alkoxy, preferably C$_1$-C$_6$-alkoxy, more preferably methoxy and ethoxy, C$_6$-C$_{30}$-aryloxy, preferably C$_6$-C$_{10}$-aryloxy, more preferably phenyloxy, C$_1$-C$_{20}$-alkylthio, preferably C$_1$-C$_6$-alkylthio, more preferably —SCH$_3$, C$_6$-C$_{30}$-arylthio, preferably C$_6$-C$_{10}$-arylthio, more preferably —SPh, SiR$^{14}$R$^{15}$R$^{16}$ where R$^{14}$, R$^{15}$ and R$^{16}$ are each as defined above and are preferably each donor-substituted phenyl groups, amino (—NR$^{14}$R$^{15}$), preferably diphenylamino, amido (—NR$^{14}$(C═O(R$^{15}$)), phosphine (—PR$^{14}$R$^{15}$), hydrazine radicals, OH, donor-substituted vinyl groups, where R$^{14}$, R$^{15}$ and R$^{16}$ are each as defined above and are preferably each donor-substituted phenyl groups, or R$^{18}$ is substituted or unsubstituted electron-rich heteroaryl having from five to 30 ring atoms, preferably selected from the group consisting of carbazolyl, pyrrolyl, imidazolyl, pyrazolyl, triazolyl, oxazolyl, thiophenyl, more preferably carbazolyl, pyrrolyl and thiophenyl.

Preferred R$^{18}$ groups are selected from the group consisting of methoxy, ethoxy, phenoxy, very particular preference being given especially to methoxy, and carbazolyl, pyrrolyl, imidazolyl, pyrazolyl, triazolyl, oxazolyl and thiophenyl, very particular preference being given to methoxy, phenyloxy, carbazolyl and NR$^{14}$R$^{15}$ where R$^{14}$ and R$^{15}$ are each phenyl or tolyl.

More preferably, the compounds of the formula (I) used in the aforementioned layers have at least one R$^1$, R$^2$, R$^3$, R$^4$, R$^5$, R$^6$ or R$^7$ radical selected from the group consisting of

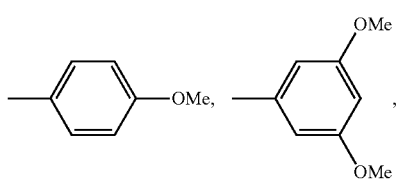

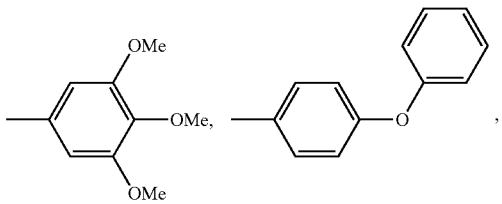

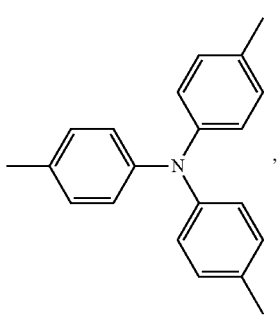

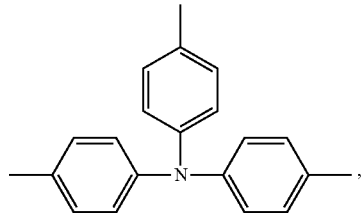

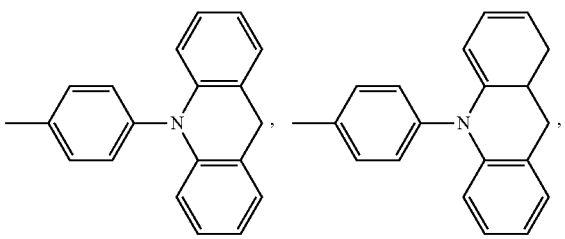

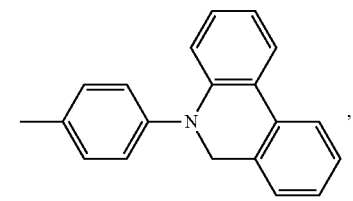

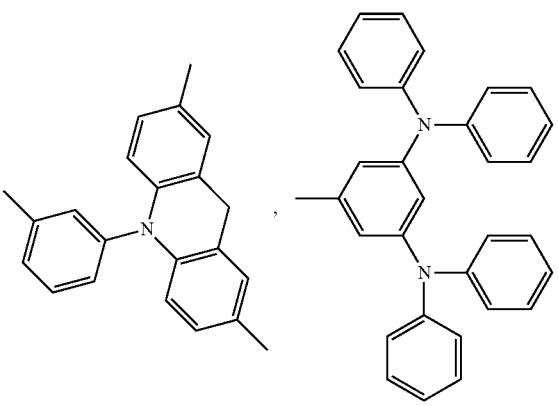

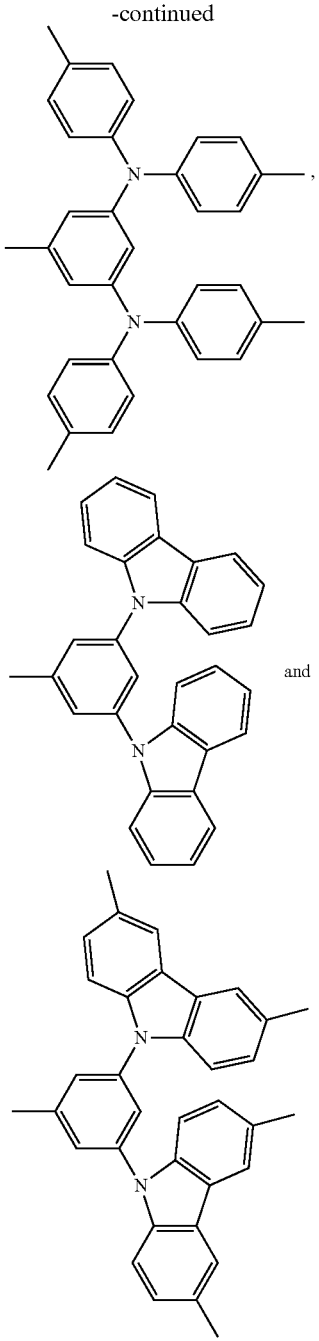

In a preferred embodiment, at least one $R^1$ radical is a $C_6$-aryl radical of the formula (d) substituted by at least one substituent with donor action and/or at least one heteroaryl radical having from 5 to 30 ring atoms;
and the $R^2$, $R^3$, $R^4$, $R^5$, $R^6$ and $R^7$ radicals are preferably each phenyl, methyl or methoxy- or phenyloxy substituted phenyl.
Use of the Compounds of the Formula (I) in the Light-emitting Layer E as Matrix Material and/or in a Blocking Layer for Holes, an Electron Injection Layer and/or an Electron Conductor Layer The present invention further relates to an inventive organic light-emitting diode in which at least one compound of the formula (I) is present in at least one of the layers selected from light-emitting layer E, blocking layer for holes, electron injection layer and electron conductor layer.

Preferred compounds of the formula (I) used in the aforementioned layers have at least one $R^1$, $R^2$, $R^3$, $R^4$, $R^5$, $R^6$ or $R^7$ radical which is $C_1$- to $C_{20}$-alkyl substituted by at least one substituent with acceptor action (electron-withdrawing radical), $C_6$-$C_{30}$-aryl substituted by at least one substituent with acceptor action, $C_6$-$C_{30}$-aryl substituted by at least one heteroaryl radical having from 5 to 30 ring atoms, or a substituent with acceptor action.

Suitable substituents with acceptor action (electron-withdrawing radicals) are selected from the group consisting of electron-deficient heteroaryls having from 5 to 30 ring atoms, carbonyl (—CO($R^{14}$)), carbonylthio (—C=O(S$R^{14}$)), carbonyloxy (—C=O(O$R^{14}$)), oxycarbonyl (—OC=O($R^{14}$)), thiocarbonyl (—SC=O($R^{14}$)), OH, halogen, halogen-substituted $C_1$-$C_{20}$-alkyl, pseudohalogen radicals, amido (—C=O(N$R^{14}$), phosphonate (—P(O) (O$R^{14}$)$_2$), phosphate (—OP(O) (O$R^{14}$)$_2$), phosphine oxide (—P(O)$R^{14}R^{15}$), sulfonyl (—S(O)$_2R^{14}$), sulfonate (—S(O)$_2$OR)sulfate (—OS(O)$_2$O$R^{14}$), sulfoxide (—S(O)$R^{14}$), sulfonamide (—S(O)$_2$N$R^{14}R^{15}$), NO$_2$, boronic esters (—OB(O$R^{14}$)$_2$), imino (—C=N$R^{14}R^{15}$)), hydrazone radicals, oxime radicals, nitroso groups, diazo groups, sulfoximines, Si$R^{14}R^{15}R^{16}$, borane radicals, stannane radicals, acceptor-substituted vinyl groups, boroxines and borazines, where $R^{14}$, $R^{15}$ and $R^{16}$ are each substituted or unsubstituted $C_1$-$C_{20}$-alkyl, preferably substituted or unsubstituted $C_1$-$C_6$-alkyl, or substituted or unsubstituted $C_6$-$C_{30}$-aryl, preferably substituted or unsubstituted $C_6$-$C_{10}$-aryl.

Preferred substituents with acceptor action are selected from the group consisting of halogen, preferably F, halogen-substituted alkyl, preferably CF$_3$, CH$_2$F, CHF$_2$, C$_2$F$_5$, C$_3$F$_3$H$_4$, pseudohalogen, preferably CN, carbonyloxy (—C=O(O$R^{14}$)), preferably —C=O(OCH$_3$), phosphine oxide, preferably P(O)Ph$_2$, and sulfonyl, preferably S(O)$_2$Ph$_2$.

The at least one radical which is used in the aforementioned layers is more preferably a substituted $C_6$-aryl radical of the formula (e)

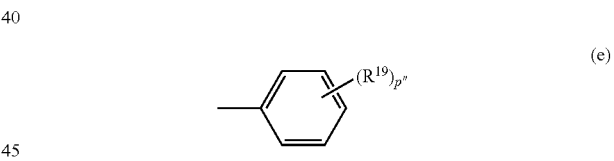

(e)

in which:
p″ is 1, 2, 3, 4 or 5, preferably 1, 2 or 3, more preferably 1 or 2; and
$R^{19}$ is carbonyl (—CO($R^{14}$)), carbonylthio (—C=O(S$R^{14}$)), carbonyloxy (—C=O(O$R^{14}$)), oxycarbonyl (—OC=O($R^{14}$)), thiocarbonyl (—SC=O($R^{14}$)), OH, halogen, halogen-substituted $C_1$-$C_{20}$-alkyl, pseudohalogen radicals, amido (—C=O(N$R^{14}$), phosphonate (—P(O) (O$R^{14}$)$_2$), phosphate (—OP(O) (O$R^{14}$)$_2$), phosphine oxide (—P(O)$R^{14}R^{15}$), sulfonyl (—S(O)$_2R^{14}$), sulfonate (—S(O)$_2$O$R^{14}$), sulfate (—OS(O)$_2$O$R^{14}$), sulfoxide (—S(O)$R^{14}$), sulfonamide (—S(O)$_2$N$R^{14}R^{15}$), NO$_2$, boronic esters (—OB(O$R^{14}$)$_2$, imino (—C=N$R^{14}R^{15}$)), hydrazone radicals, oxime radicals, nitroso groups, diazo groups, sulfoximines, Si$R^{14}R^{15}R^{16}$, and borane radicals, stannane radicals, acceptor-substituted vinyl groups, boroxines and borazines, where $R^{14}$, $R^{15}$ and $R^{16}$ are each substituted or unsubstituted $C_1$-$C_{20}$-alkyl, preferably substituted or unsubstituted $C_1$-$C_6$-alkyl, or substituted or unsubstituted $C_6$-$C_{30}$-aryl, preferably substituted or unsubstituted $C_6$-$C_{10}$-aryl; preferably halogen, preferably F, halogen-substituted alkyl, preferably $CF_3$, $CH_2F$, $CHF_2$, $C_2F_5$, $C_3F_3H_4$, pseudohalogen, preferably CN, carbonyloxy (—C=O($OR^{14}$)), preferably —C=O($OCH_3$), phosphine oxide, preferably P(O)$Ph_2$, and sulfonyl, preferably S(O)$_2$ $Ph_2$;

or $R^{19}$ is substituted or unsubstituted electron-deficient heteroaryl having from five to 30 ring atoms, preferably selected from the group consisting of pyridine, pyrimidine and triazine.

More preferably, the compounds of the formula (I) used in the aforementioned layers have at least one $R^1$, $R^2$, $R^3$, $R^4$, $R^5$, $R^6$ or $R^7$ radical, selected from the group consisting of:

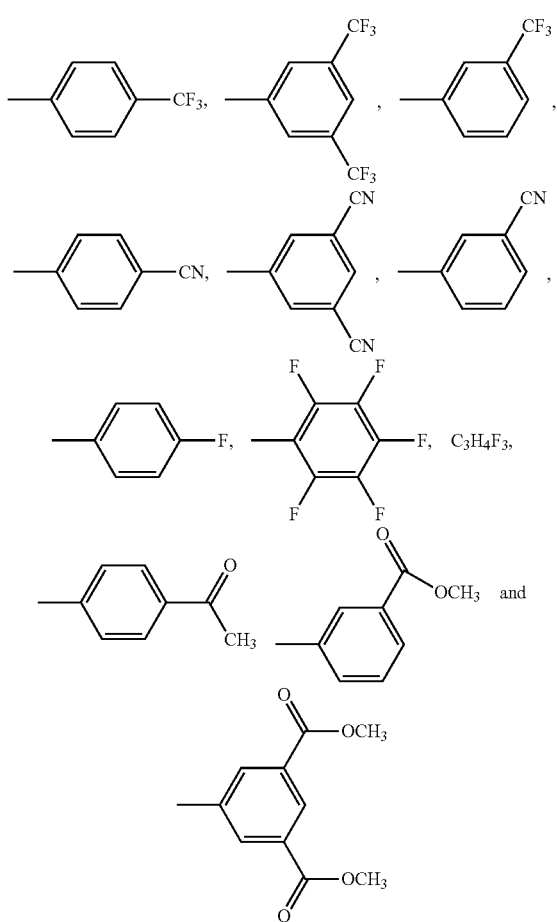

Preparation of the Compounds of the Formula (I) Used in Accordance with the Invention The compounds of the formula (I) can in principle be prepared by processes known to those skilled in the art; for example, carbazoles of the formula (I) (X=$NR^1$) can be prepared thermally or photochemically by oxidative ring closure from diphenylamine (or suitably substituted derivatives thereof) and, if appropriate, subsequent substitution, for example on the nitrogen. In addition, the carbazoles of the formula (I) can be obtained proceeding from the suitably substituted tetrahydrocarbazoles by oxidation. A typical carbazole synthesis is the Borsche-Drechsel cyclization (Borsche, Ann., 359, 49 (1908); Drechsel, J. prakt. Chem., [2], 38, 69, 1888). The aforementioned tetrahydrocarbozoles can be prepared by processes known to those skilled in the art, for example by condensation of, if appropriate, suitably substituted phenylhydrazine with, if appropriate, suitably substituted cyclohexanone to obtain the corresponding imine. In a subsequent step, an acid-catalyzed rearrangement and ring closure reaction is effected to obtain the corresponding tetrahydrocarbozole. It is likewise possible to carry out the preparation of the imine and the rearrangement and ring closure reaction in one step. The imine is—as mentioned above—oxidized to the desired carbazole.

The compounds of the formula (I) are prepared preferably proceeding from the corresponding base structure of the formula (II):

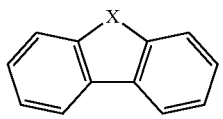

(II)

where X is $NR^1$, SO, $SO_2$, S, O or $PR^1$ or NH or PH or PPh. Suitable base structures of the formula (II) are either commercially available (especially in the cases when X is $SO_2$, S, O, NH or PPh) or can be prepared by processes known to those skilled in the art (X=PH or SO).

In the case that X is NH or PH, the $R^1$ radicals may be introduced before or after the introduction of the $R^a$, $R^b$, $SiR^2R^3R^4$ and $SiR^5R^6R^7$ radicals, provided that the $R^a$ and $R^b$ radicals are present in the compounds of the formula (I) or precursor compounds suitable for introducing the $R^a$, $R^b$, $SiR^2R^3R^4$ and $SiR^5R^6R^7$ radicals. Thus, three variants—in the case that X=$NR^1$ and $PR^1$—are possible:

Variant a)
ia) preparing a precursor compound suitable for introducing the $R^a$, $R^b$, $SiR^2R^3R^4$ and $SiR^5R^6R^7$ radicals,
iia) introducing the $R^1$ radical,
iiia) introducing the $R^a$, $R^b$ radicals, where present, and the $SiR^2R^3R^4$ and $SiR^5R^6R^7$ radicals.

Variant b)
Variant b) is preferred especially when $R^1$ is substituted or unsubstituted $C_1$-$C_{20}$-alkyl or $C_6$-$C_{30}$-aryl or $C_1$-$C_{20}$-alkyl-substituted $C_6$-$C_{30}$-aryl.
ib) introducing the $R^1$ radical,
iib) preparing a precursor compound suitable for introducing the $R^a$, $R^b$, $SiR^2R^3R^4$ and $SiR^5R^6R^7$ radicals,
iiib) introducing the $R^a$, $R^b$ radicals, where present, and the $SiR^2R^3R^4$ and $SiR^5R^6R^7$ radicals.

Variant c)
ic) preparing a precursor compound suitable for introducing the $R^a$, $R^b$, $SiR^2R^3R^4$ and $SiR^5R^6R^7$ radicals,
iic) introducing the $R^a$, $R^b$ radicals, where present, and the $SiR^2R^3R^4$ and $SiR^5R^6R^7$ radicals,
iiic) introducing the $R^1$ radical.

In the case that X in formula (I) is $NR^1$, SO, $SO_2$, S, O or $PR^1$, the step of "introducing the $R^1$ radical" is dispensed with, such that the process comprises the following steps (Variant d):
id) preparing a precursor compound suitable for introducing the $R^a$, $R^b$, $SiR^2R^3R^4$ and $SiR^5R^6R^7$ radicals,
iid) introducing the $R^a$, $R^b$ radicals, where present, and the $SiR^2R^3R^4$ and $SiR^5R^6R^7$ radicals.

Steps ia), iib), ic) and id)
Suitable precursor compounds for introducing the $R^a$, $R^b$, $SiR^2R^3R^4$ and $SiR^5R^6R^7$ radicals are especially the corresponding halogenated, preferably brominated, compounds of the general formula (III):

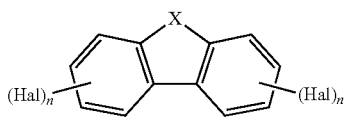

where Hal is halogen, preferably bromine or iodine, more preferably bromine, n is in each case 0, 1 or 2 (where the sum of the two n in formula (III) is at least 1), preferably in each case 1, and X in steps ia) and ic) is NH or PH, X in step ib) is $NR^1$ or $PR^1$, and X in step id) is $NR^1$, SO, $SO_2$, S, O or $PR^1$.

The halogenation can be carried out by processes known to those skilled in the art. Preference is given to brominating or iodinating in the 3 and 6 position of the base structure of the formula (II).

Particular preference is given to brominating with $Br_2$ in glacial acetic acid or chloroform at low temperatures, for example 0° C. Suitable processes are, for example, described in M. Park, J. R. Buck, C. J. Rizzo, Tetrahedron, 1998, 54, 12707-12714 for X=NPh, and in W. Yang et al., J. Mater. Chem. 2003, 13, 1351 for X=S. In addition, some brominated products of the formula (III) are commercially available (for X=NH and S).

Steps iia), ib) and iiic)

The $R^1$ radical is introduced by processes known to those skilled in the art.

The radical is introduced preferably by reacting the base structure of the formula (II) or the compound of the formula (III) with an alkyl halide or aryl halide or heteroaryl halide of the formula $R^1$-Hal where $R^1$ has already been defined above and Hal is F, Cl, Br or I, preferably Br, I or F.

The introduction of the $R^1$ radical is generally carried out in the presence of a base. Suitable bases are known to those skilled in the art and are preferably selected from the group consisting of alkali metal and alkaline earth metal hydroxides such as NaOH, KOH, $Ca(OH)_2$, alkali metal hydrides such as NaH, KH, alkali metal amides such as $NaNH_2$, alkali metal or alkaline earth metal carbonates such as $K_2CO_3$ or $Cs_2CO_3$, and alkali metal alkoxides such as NaOMe, NaOEt. Additionally suitable are mixtures of the aforementioned bases. Particular preference is given to NaOH, KOH, $K_2CO_3$ or NaH.

The N-alkylation (for example disclosed in M. Tosa et al., Heterocycl. Communications, Vol. 7, No. 3, 2001, p. 277-282) or N-arylation or N-heteroarylation (for example (N-arylation) disclosed in H. Gilman and D. A. Shirley, J. Am. Chem. Soc. 66 (1944) 888; D. Li et al., Dyes and Pigments 49 (2001) 181-186) is preferably carried out in a solvent. Suitable solvents are, for example, polar aprotic solvents such as dimethyl sulfoxide, dimethylformamide or alcohols. It is likewise possible to use an excess of the alkyl halide or (hetero)aryl halide used as the solvent. The reaction can additionally be performed in a nonpolar aprotic solvent, for example toluene, when a phase transfer catalyst, for example tetra-n-butylammonium hydrogensulfate, is present (as disclosed, for example, in I. Gozlan et al., J. Heterocycl. Chem. 21 (1984) 613-614).

The N-(hetero)arylation can, for example, be effected by copper-catalyzed coupling of the compound of the formula (II) or (III) to a (hetero)aryl halide, for example an aryl iodide (Ullmann reaction).

Preference is given to introducing the $R^1$ radical by reacting the compound of the formula (II) or (III) with an alkyl fluoride, aryl fluoride or heteroaryl fluoride in the presence of NaH in DMF (nucleophilic substitution), or by reaction with an alkyl bromide or iodide, aryl bromide or iodide or heteroaryl bromide or iodide under Cu/base (Ullmann, see above) or Pd catalysis.

The molar ratio of the compound of the formula (II) or (III) to the alkyl halide or (hetero)aryl halide of the formula $R^1$—Hal is generally from 1:1 to 1:15, preferably from 1:1 to 1:6, more preferably 1:4.

The N-alkylation or N-(hetero)arylation is performed generally at a temperature of from 0 to 220° C., preferably from 20 to 200° C. The reaction time is generally from 0.5 to 48 h, preferably from 1 to 24 h. In general, the N-alkylation or N-arylation is performed at standard pressure.

The resulting crude product is worked up by processes known to those skilled in the art.

Preferred embodiments of steps iia), ib) and iiic) are detailed hereinafter in general form using the example of $R^1$=substituted phenyl (R=aforementioned substituent on the aryl radical; q=0, 1, 2, 3, 4 or 5):

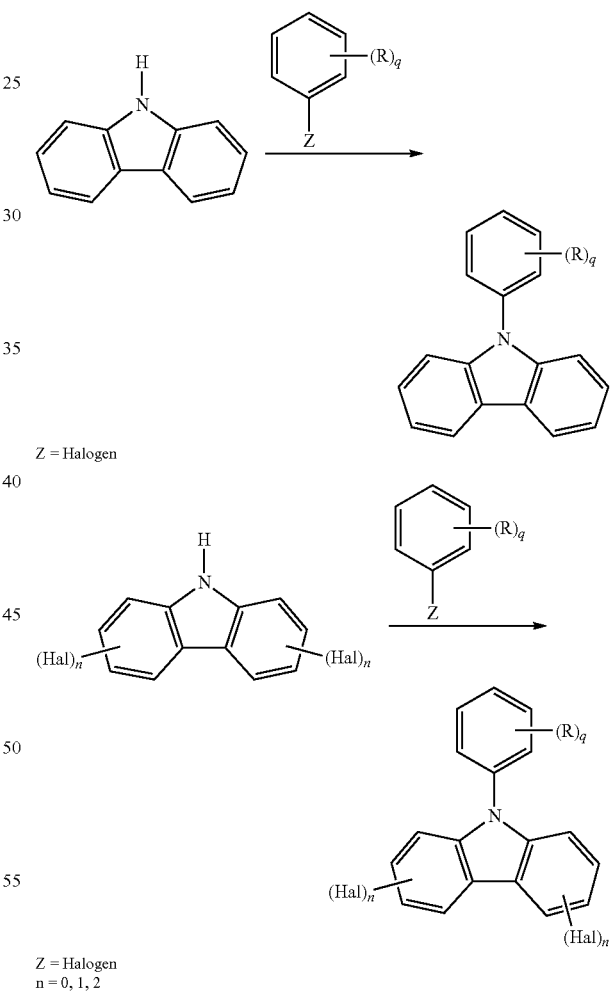

Steps iiia), iiib), iic) and iid)

The desired silylated compounds of the formula (I) are prepared proceeding from the halogenated precursor compounds of the formula (III) generally by halogen/metal exchange and subsequent silylation by processes known to those skilled in the art.

Preference is given to effecting the preparation, in a first step, by halogen/metal exchange by reaction of the halogenated compounds of the formula (III) with alkyllithium compounds or Mg at temperatures of generally from −80° C. to +80° C., preferably at from −78° C. to 0° C. (for alkyllithium compounds) or from 0° C. to 80° C. (for Mg), more preferably from 0° C. to 40° C. (for Mg). Particular preference is given to using alkyllithium compounds, especially n-BuLi or tert-BuLi. The reaction is effected generally in a solvent, preferably in THF (or ether, preferably diethyl ether). In a directly subsequent second step, a silylation is effected to give the desired compounds of the formula (I), preferably by reaction with $SiR_mCl_{(4-m)}$ or $SiR_m(OR')_{(4-m)}$, where m is 1, 2 or 3 and R' is $C_1$- to $C_6$-alkyl. The silylation is generally carried out in a solvent. Preferred solvents are THF or ethers, preferably diethyl ether. In general, the silylation is effected directly after the reaction in the first step, without workup or isolation of the product obtained after the first step. The halogen/metal exchange and the subsequent silylation are generally repeated sufficient times for all n halogen radicals in the compound of the formula (III) to be replaced by silyl groups. Tsai et al., Adv. Mater., 2006, Vol. 18, No. 9, pages 1216 to 1220.

In the case when the halogen/metal exchange and the subsequent silylation are performed on a compound of the formula (III) in which X=NH or PH (variant c), step iic)), it is necessary to protect the NH or PH group by means of a protecting group and to deprotect again after the silylation.

The protecting group is introduced by processes known to those skilled in the art. In general, initial deprotonation is followed by introduction of a protecting group. Suitable N—H and P—H protecting groups are known to those skilled in the art, and silyl protecting groups, especially $SiR_3$ where R=alkyl or aryl, preferably methyl, ethyl, phenyl, are particularly suitable for this process. The deprotonation is effected typically with bases, for example with NaH, nBuLi or tert-BuLi.

The deprotection is likewise effected by processes known to those skilled in the art. Suitable reagents for deprotection are guided by the protecting groups used. When $SiR_3$ is used as the protecting group, the deprotection is effected generally with an acid or TBAF (tetrabutylammonium fluoride).

Preferred embodiments of steps iiia), iiib) and iid) are shown below in general form (X=$NR^1$, SO, $SO_2$, S, O or $PR^1$):

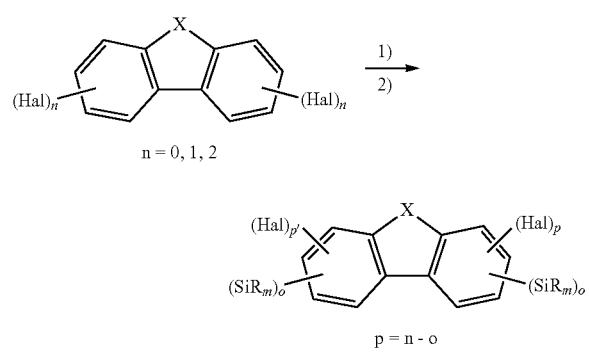

1) Halogen/metal exchange
2) Silylation, $SiR_m(Cl)_{4-m}$ or $SiR_m(OR')_{4-m}$ When p=1 or 2, step 1 and 2 can be repeated once again until p=0.

In step iic) (X=NH or PH), the halogen/metal exchange with subsequent silylation is generally preceded by the introduction of a protecting group. A preferred embodiment of step iic) is shown below using the example of X=NH:

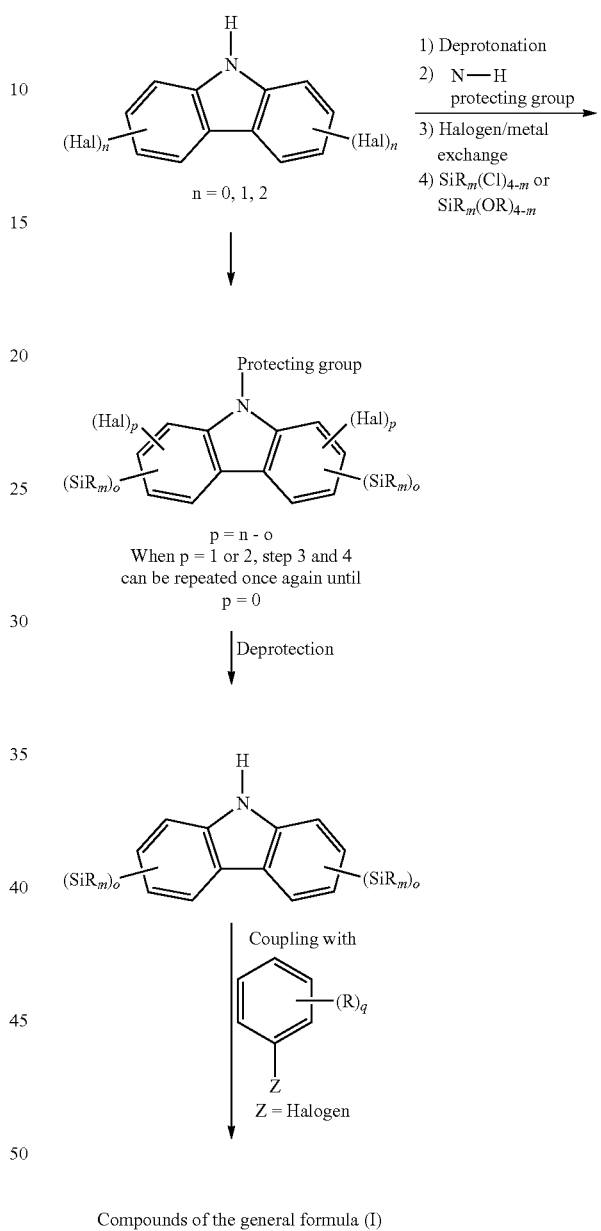

Compounds of the general formula (I)

Use of the inventive compounds of the formula (I) as matrix materials in the light-emitting layer and/or in at least one further layer of the inventive OLEDs selected from disilylcarbazoles, disilyldibenzofurans, disilyldibenzothiophenes, disilyldibenzophospholes, disilyldibenzothiophene S-oxides and disilyldibenzothiophene S,S-dioxides allows OLEDs with high efficiency and lifetime to be obtained. The efficiency of the inventive OLEDs can additionally be improved by optimizing the other layers. For example, highly efficient cathodes such as Ca or Ba, if appropriate in combination with an intermediate layer of LiF, can be used. Shaped substrates and novel hole-transporting materials which bring about a reduction in the operating voltage or an increase in the quantum efficiency can likewise be used in the inventive OLEDs. In addition, additional layers may be present in the OLEDs in order to adjust the energy level of the different layers and in order to facilitate electroluminescence.

The inventive OLEDs can be used in all devices in which electroluminescence is useful. Suitable devices are preferably selected from stationary and mobile visual display units and illumination units. Stationary visual display units are, for example, visual display units of computers, televisions, visual display units in printers, kitchen appliances and advertising panels, illuminations and information panels. Mobile visual display units are, for example, visual display units in cellphones, laptops, digital cameras, vehicles and destination displays on buses and trains.

In addition, the compounds of the formula (I) can be used in OLEDs with inverse structure. Preference is given to using the compounds of the formula (I) used in accordance with the invention in these inverse OLEDs, in turn, as matrix materials in the light-emitting layer and/or in at least one further layer of the OLED. The structure of inverse OLEDs and the materials customarily used therein are known to those skilled in the art.

The present invention further relates to a light-emitting layer comprising at least one compound of the formula (I) according to the present invention and at least one emitter material. Preferred compounds of the formula (I) and emitter materials are specified above.

In general, the proportion of the at least one compound of the formula (I) in the light-emitting layer of the inventive OLED is from 10 to 99% by weight, preferably from 50 to 99% by weight, more preferably from 70 to 97% by weight. The proportion of the at least one emitter material in the light-emitting layer is generally from 1 to 90% by weight, preferably from 1 to 50% by weight, more preferably from 3 to 30% by weight, where the proportions of the at least one compound of the formula (I) and the at least one emitter compound add up to 100% by weight. However, it is also possible that the light-emitting layer, as well as the at least one compound of the general formula (I) and the at least one emitter material, comprises further substances, for example further diluent material, further matrix material other than the compounds of the formula (I), further diluent material, for example, being specified above.

The present invention further provides for the use of compounds of the general formula I according to the present application as matrix material, hole/exciton blocker material and/or electron/exciton blocker material and/or hole injection material and/or electron injection material and/or hole conductor material and/or electron conductor material in an organic light-emitting diode. Preference is given to using the compounds of the formula (I) as matrix materials and/or hole/exciton blocker materials in the inventive OLED.

Preferred compounds of the formula (I), preferred emitter materials and preferred embodiments relating to the use of compounds of the formula (I) which have particular substituents in specific layers of the inventive OLEDs are specified above.

The present invention further relates to a device selected from the group consisting of stationary visual display units such as visual display units of computers, televisions, visual display units in printers, kitchen appliances and advertising panels, illuminations, information panels and mobile visual display units, such as visual display units in cellphones, laptops, digital cameras, vehicles and destination displays on buses and trains, and illumination units comprising at least one inventive organic light-emitting diode or at least one inventive light-emitting layer.

The examples which follow provide additional illustration of the invention.

EXAMPLES

A Preparation Examples

Example 1

Bromination of N-substituted Carbazoles

Example 1a

Synthesis of 9-(3,5-bis(trifluoromethyl)phenyl)-3,6-dibromocarbazole

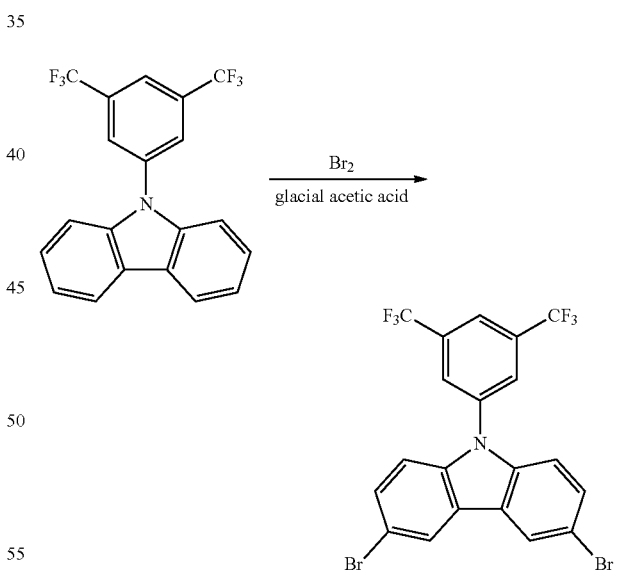

A solution of 9-(3,5-bis(trifluoromethyl)phenyl)-9H-carbazole (2.7 g, 1 eq) in glacial acetic acid (210 ml) is slowly admixed with a solution of bromine (2.3 g, 2.0 eq) in glacial acetic acid (7 ml). After stirring for 1 h, the mixture is admixed with ice-water (1000 ml) and stirred for 1 h. The precipitate is filtered off and washed with water. The residue is recrystallized in ethyl acetate. Yield 55%. $^1$H NMR (THF-d8, 400 MHz): δ=7.3 (d, 2H), 7.6 (d, 2H), 8.2 (s, 1H), 8.3 (s, 2H), 8.4 (s, 2H).

Example 1b

Synthesis of 9-(3-cyanophenyl)-3,6-dibromocarbazole

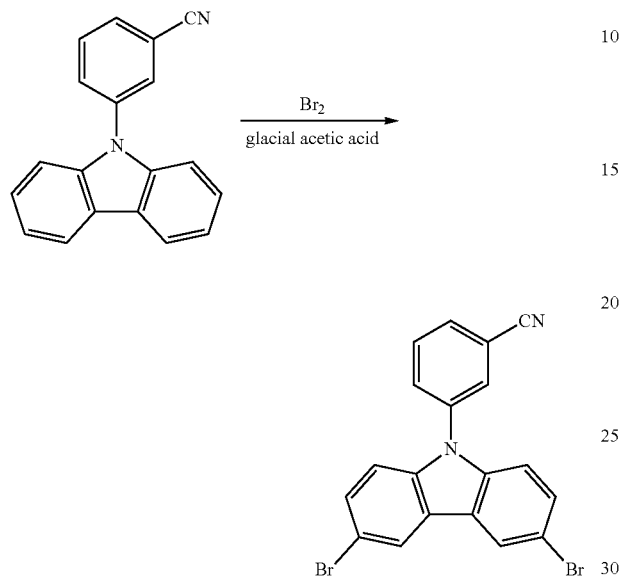

A solution of 9-(3-cyanophenyl)-9H-carbazole (3.5 g, 1 eq) in glacial acetic acid (150 ml) is admixed slowly with a solution of bromine (4.1 g, 2.0 eq) in glacial acetic acid (5 ml). After stirring for 3 h, the mixture is admixed with ice-water (500 ml) and stirred for 1 h. The precipitate is filtered off and washed with water. The residue is recrystallized in ethanol. Yield 69%. $^1$H NMR (CDCl$_3$, 400 MHz): δ=7.2 (d, 2H), 7.5 (d, 2H), 7.75 (m, 3H), 7.8 (s, 1H), 8.2 (s, 2H).

Example 2

N-Arylation of Carbazole (X in the General Formula II is N—H)

General Procedure:

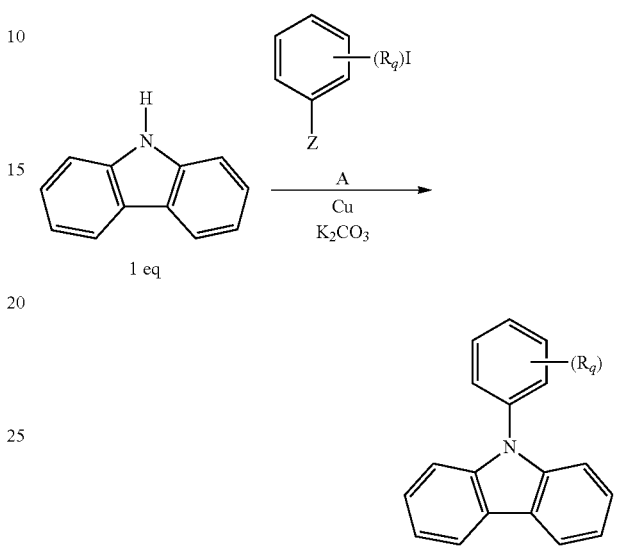

Carbazole (1 eq), phenyl halide A, potassium carbonate and copper powder are heated to 160-200° C. and stirred overnight at this temperature. After cooling to room temperature, the mixture is extracted with acetone or methylene chloride. The precipitate is filtered off and purified by column chromatography (silica gel, methylene chloride/cyclohexane).

The table which follows summarizes the data of various N-arylations of carbazole which have been carried out according to the general method:

| A | Equiv. A | Equiv. K$_2$CO$_3$ | Mol % Cu | T (° C.) | Yield | Analysis |
|---|---|---|---|---|---|---|
| 2a (3,5-bis(CF$_3$)-iodobenzene) | 1.1 | 1.5 | 12 | 165 | 41 | $^1$H NMR (CDCl$_3$, 400 MHz): δ = 7.35 (m, 4H), 7.4 (m, 2H), 7.9 (s, 1H), 8.1 (s, 2H), 8.2 (d, 2H). MALDI-MS: m/z = 379 |
| 2b (3,5-dimethoxy-bromobenzene) | 1.1 | 1.2 | 12.5 | 180 | 76 | $^1$H NMR (CDCl$_3$, 400 MHz): δ = 3.8 (s, 6H), 6.6 (s, 1H), 6.7 (s, 2H), 7.3 (dd, 2H), 7.4 (dd, 2H), 7.5 (d, 2H), 8.1 (d, 2H); MALDI-MS: m/z = 303 |

| A | Equiv. A | Equiv. $K_2CO_3$ | Mol % Cu | T (° C.) | Yield | Analysis |
|---|---|---|---|---|---|---|
| 2c (2,6-dimethoxy-4-bromo-anisole) | 1.1 | 1.2 | 12.5 | 180-200 | 73 | $^1$H NMR (CDCl$_3$, 400 MHz): δ = 3.8 (s, 6H), 3.9 (s, 3H), 6.8 (s, 2H), 7.3 (m, 2H), 7.4 (virtually d, 4H), 8.2 (d, 2H). |
| 2d (3-iodobenzonitrile) | 1.1 | 1.2 | 12.5 | 175 | 73 | $^1$H NMR (CDCl$_3$, 400 MHz): δ = 7.3 (m, 4H), 7.45 (dd, 2H), 7.7 (dd, 2H), 7.8 (dd, 1H), 7.9 (s, 1H), 8.2 (d, 2H). |

Example 3

N-Arylation of Brominated Carbazole Derivatives (X in the General Formula II is N—H)

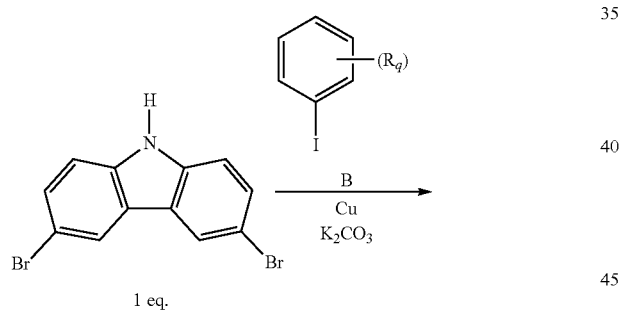

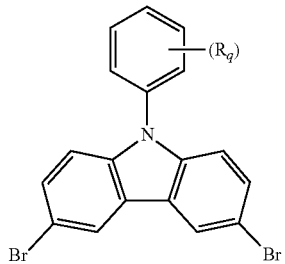

General Procedure:

Carbazole (1 eq), phenyl iodide B, potassium carbonate and copper powder are heated to 130-160° C. and stirred at this temperature for 48 h. Cooling to room temperature is followed by extraction with methylene chloride. Recrystallization from EtOH gives the desired product.

The table which follows summarizes the data of various N-arylations of brominated carbazole derivatives which have been carried out according to the general procedure:

| B | Equiv. B | Equiv. $K_2CO_3$ | Mol % Cu | T (° C.) | Yield | Analysis |
|---|---|---|---|---|---|---|
| 3a | 4 | 2.5 | 21 | 130 | 70 | $^1$H NMR (CDCl$_3$, 400 MHz): δ = 3.9 (s.6H), 4.0 (s, 3H), 6.6 (s, 2H), 7.2 (d, 2H), 7.5 (d, 2H), 8.2 (s, 2H). |

| B | Equiv. B | Equiv. $K_2CO_3$ | Mol % Cu | T (°C.) | Yield | Analysis |
|---|---|---|---|---|---|---|
| 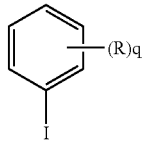 3b | 2.9 | 2.6 | 18 | 125 | 68 | $^1$H NMR (CDCl$_3$, 400 MHz): δ = 1.4 (s, 9H), 7.25 (d, 2H). 7.37 (d, 2H), 7.47 (d, 2H), 7.6 (d, 2H), 8.2 (s, 2H). |
| 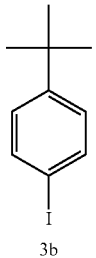 3c | 2 | 1.25 | 11 | 130 | 60 | $^1$H NMR (CDCl$_3$, 400 MHz): δ = 3.9 (s, 3H), 7.1 (d, 2H), 7.2 (d, 2H), 7.4 (d, 2H), 7.5(d, 2H), 8.2 (s, 2H). |

Example 4

Coupling of Brominated N-arylated Carbazole Derivatives and Brominated Dibenzothiophene Derivatives with Silyl Compounds

Example 4a

Synthesis of 2,8-bis(triphenylsilyl)dibenzothiophene

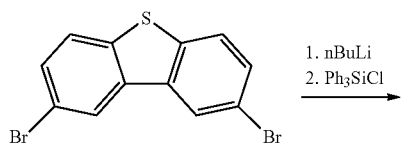

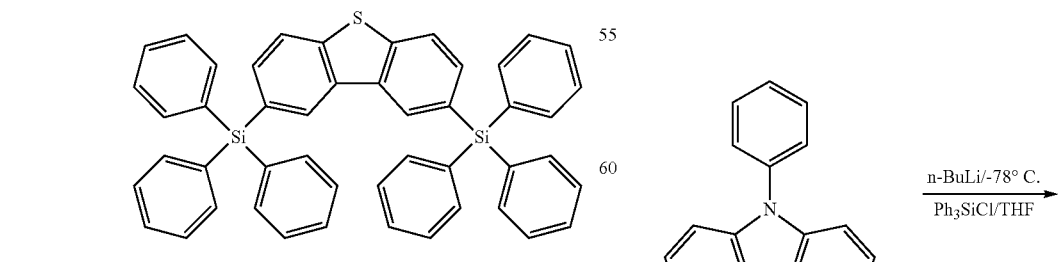

A solution of 2,8-dibromodibenzothiophene (3.0 g, 1 eq) in dry THF (165 ml) at −78° C. under argon is admixed slowly with n-butyllithium (1.6 M in hexane, 13.7 ml, 2.5 eq), and stirred at −78° C. for 1 h. After adding a solution of chlorotriphenylsilane (6.5 g, 2.5 eq) in dry THF (14 ml) at −78° C., the mixture is warmed to room temperature with stirring overnight. Excess butyllithium is hydrolyzed with saturated ammonium chloride solution. The precipitated product is filtered off and washed thoroughly with THF, water and methyl tert-butyl ether. The combined THF filtrates are concentrated to dryness and stirred with a little ethyl acetate. The precipitate is filtered off and purified by column chromatography (silica gel, ethyl acetate/cyclohexane). Yield: 46%. $^1$H NMR (CD$_2$Cl$_2$, 400 MHz): δ=7.35-7.41 (m, 12H), 7.44-7.49 (m, 6H), 7.55-7.59 (m, 12H), 7.65 (d, J=8.0, 2H), 7.92 (d, J=8.0, 2H), 8.16 (s, 2H).

Example 4b

Synthesis of 9-phenyl-3,6-bis(triphenylsilyl)-carbazole

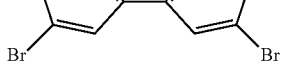

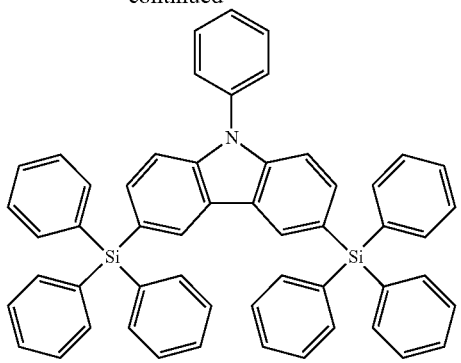

A solution of 9-phenyl-3,6-dibromo-9H-carbazole (6.0 g, 1 eq) in dry THF (500 ml) at −78° C. under argon is admixed slowly with n-butyllithium (1.6 M in hexane, 28.2 ml, 3.0 eq) and stirred at −78° C. for 1 h. After adding a solution of chlorotriphenylsilane (13.5 g, 3.0 eq) in dry THF (100 ml) at −78° C., the mixture is warmed to room temperature with stirring overnight. Excess butyllithium is hydrolyzed with saturated ammonium chloride solution. The precipitated product is filtered off and washed thoroughly with $CH_2Cl_2$. The product precipitates out of the combined $CH_2Cl_2$ filtrates. Yield: 40%. If the product does not precipitate out, the combined $CH_2Cl_2$ filtrates are concentrated to dryness. Recrystallization with ethyl acetate gives the product. $^1H$ NMR (CDCl$_3$, 400 MHz): δ=7.35 (m, 12H), 7.45 (m, 9H), 7.52-7.6 (m, 18H), 8.2 (s, 2H).

Example 4c

Synthesis of 9-(3,4,5-trimethoxyphenyl)-3,6-bis(triphenylsilyl)-carbazole

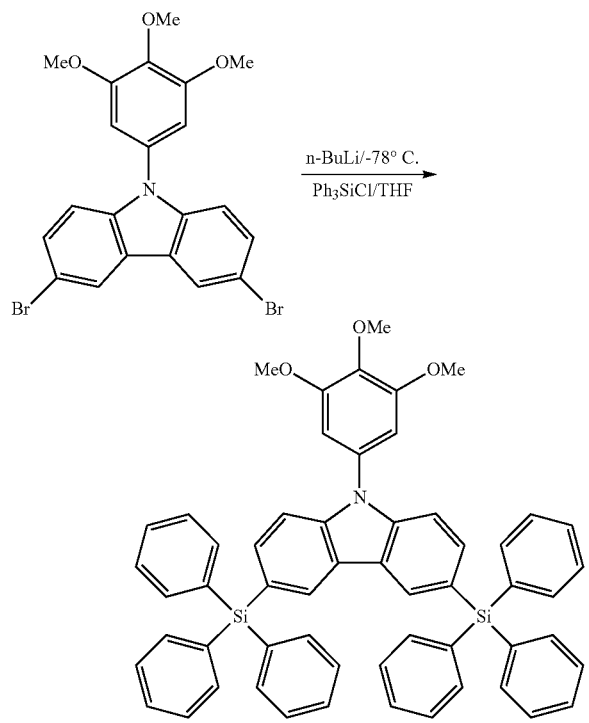

A solution of 9-(3,4,5-trimethoxyphenyl)-3,6-dibromo-9H-carbazole (1.5 g, 1 eq) in dry THF (100 ml) at −78° C. under argon is admixed slowly with n-butyllithium (1.6 M in hexane, 5.6 ml, 3.0 eq) and stirred at −78° C. for 1 h. After adding a solution of chlorotriphenylsilane (2.7 g, 3.0 eq) in dry THF (40 ml) at −78° C., the mixture is warmed to room temperature with stirring overnight. Excess butyllithium is hydrolyzed with saturated ammonium chloride solution. The precipitated product is filtered off and washed thoroughly with methylene chloride. The combined methylene chloride filtrates are concentrated to dryness. The solid is stirred in methanol and filtered off. Yield: 63%. $^1H$ NMR (CDCl$_3$, 400 MHz): δ=3.8 (s, 6H), 3.9 (s, 3H), 6.75 (s, 2H), 7.3 (m, 12H), 7.4 (m, 8H), 7.6 (m, 14H), 8.2 (s, 2H).

Example 4d

Synthesis of 3,6-bis[(3,5-bis(trifluoromethyl)phenyl)dimethylsilyl]-9-phenyl-carbazole

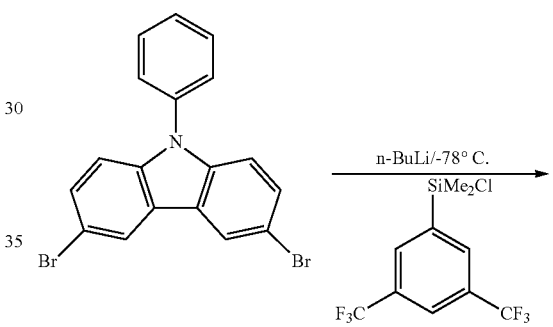

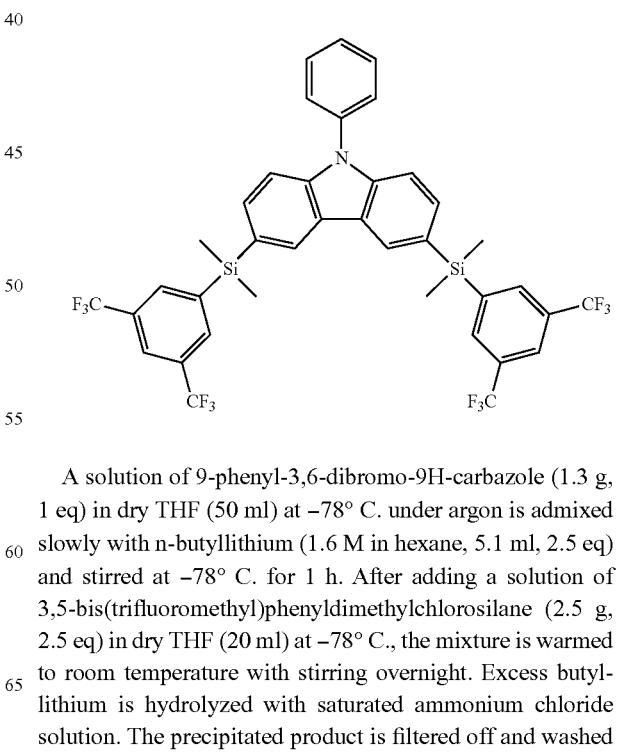

A solution of 9-phenyl-3,6-dibromo-9H-carbazole (1.3 g, 1 eq) in dry THF (50 ml) at −78° C. under argon is admixed slowly with n-butyllithium (1.6 M in hexane, 5.1 ml, 2.5 eq) and stirred at −78° C. for 1 h. After adding a solution of 3,5-bis(trifluoromethyl)phenyldimethylchlorosilane (2.5 g, 2.5 eq) in dry THF (20 ml) at −78° C., the mixture is warmed to room temperature with stirring overnight. Excess butyllithium is hydrolyzed with saturated ammonium chloride solution. The precipitated product is filtered off and washed thoroughly with CH$_2$Cl$_2$. The combined methylene chloride filtrates are extracted with water and concentrated to dryness. The residue is purified by column chromatography (silica gel, methylene chloride/cyclohexane). Yield 60%. $^1$H NMR (CDCl$_3$, 400 MHz): δ=0.7 (s, 12H), 7.4-7.7 (m, 9H), 7.8 (s, 2H), 8.0 (s, 4H), 8.3 (s, 2H).

Example 4e

Synthesis of 3,6-bis[(4-methoxyphenyl)dimethylsilyl]-9-phenylcarbazole

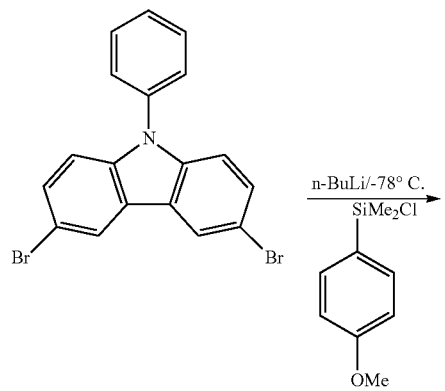

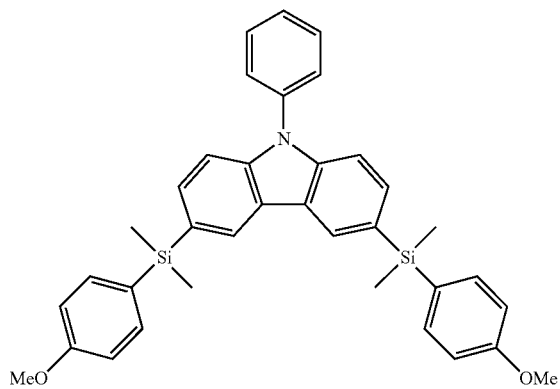

A solution of 9-phenyl-3,6-dibromo-9H-carbazole (1.6 g, 1 eq) in dry THF (20 ml) at −78° C. under argon is admixed slowly with n-butyllithium (1.6 M in hexane, 6.1 ml, 2.5 eq) and stirred at −78° C. for 1 h. After adding a solution of 4-methoxyphenyl-dimethylchlorosilane (2.4 g, 3.1 eq) in dry THF (10 ml) at −78° C., the mixture is warmed to room temperature with stirring overnight. Excess butyllithium is hydrolyzed with saturated ammonium chloride solution. The precipitated product is filtered off and washed thoroughly with CH$_2$Cl$_2$. The combined methylene chloride filtrates are extracted with water and concentrated to dryness. The residue is purified by column chromatography (silica gel, hexane/ethyl acetate). Yield 40%. MALDI-MS: m/z=571. HPLC: 99% purity.

Example 4f

Synthesis of 9-(3-methoxyphenyl)-3,6-bis(triphenylsilyl)carbazole

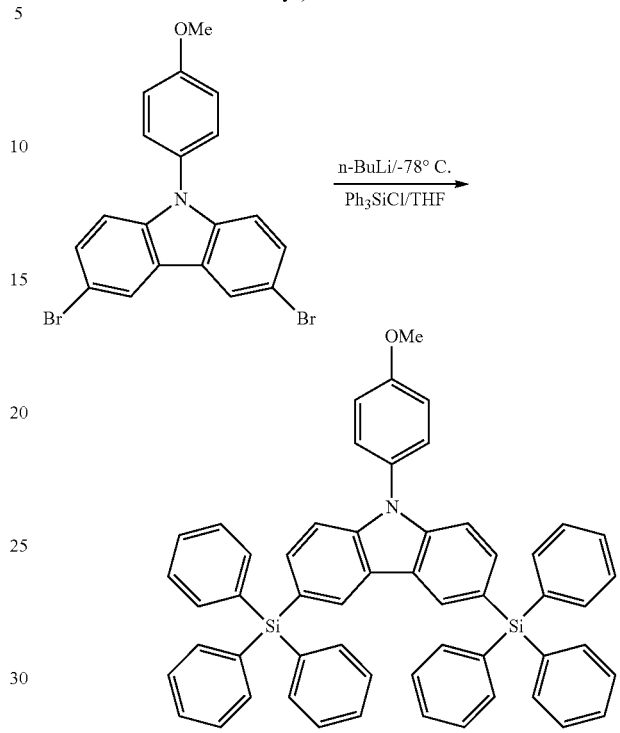

A solution of 9-(3-methoxyphenyl)-3,6-dibromo-9H-carbazole (2.5 g, 1 eq) in dry THF (100 ml) at −78° C. under argon is admixed slowly with n-butyllithium (1.6 M in hexane, 5.6 ml, 2.5 eq) and stirred at −78° C. for 1 h. After adding a solution of chlorotriphenylsilane (4.3 g, 2.5 eq) in dry THF (40 ml) at −78° C., the mixture is warmed to room temperature with stirring overnight. Excess butyllithium is hydrolyzed with saturated ammonium chloride solution. The precipitated product is filtered off and washed thoroughly with methylene chloride. The combined methylene chloride filtrates are extracted with water and concentrated to dryness. The residue is purified by column chromatography (silica gel, cyclohexane/methylene chloride). Yield 41%. $^1$H NMR (CDCl$_3$, 400 MHz): δ=3.9 (s, 3H), 7.05 (d, 2H), 7.15 (m, 14H), 7.20 (m, 8H), 7.55 (d, 2H), 7.60 (d, 12H), 8.2 (s, 2H).

Example 4g

Synthesis of 2,8-bis(triphenylsilyl)dibenzofuran

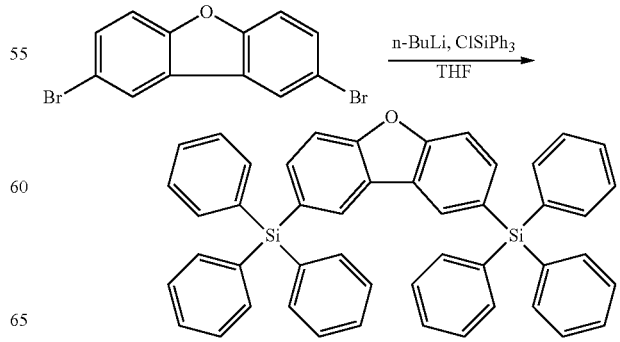

Reaction Procedure:

6.02 g (18.47 mmol) of 2,8-dibromodibenzofuran are suspended in 120 ml of THF and admixed cautiously at −78° C. with 22.9 ml (36.64 mmol) of n-BuLi (1.6M in hexane). Thereafter, the mixture is stirred at −78° C. for 3 h. The reaction mixture is admixed with a solution of 10.91 g (37.00 mmol) of chlorotriphenylsilane in 120 ml of THF, allowed to warm to room temperature and stirred at room temperature for 16 h. The mixture is quenched cautiously with 10 ml of methanol and then concentrated to dryness. The residue is digested first in methanol, then in water and subsequently in methanol again, filtered off and dried. The crude product is dissolved in methylene chloride, filtered through silica gel and crystallized by blanketing with cyclohexane. The crystals are filtered off and dried. 9.28 g (73%) of white powder are obtained.

$^1$H NMR: (CD$_2$Cl$_2$, 500 MHz):

δ=7.35-7.38 (m, 12 H, CH$_{Ar}$), 7.41-7.44 (m, 6 H, CH$_{Ar}$), 7.56-7.57 (m, 12 H, CH$_{Ar}$), 7.58-7.63 (m, 4 H, CH$_{Ar}$), 8.09 (s, 2 H, CH$_{Ar}$).

$^{13}$C NMR (CD$_2$Cl$_2$, 125 MHz):

δ=111.5 (2C, CH$_{Ar}$), 124.0 (2C, C$_{quart}$), 128.1 (12C, CH$_{Ar}$), 128.3 (2C, C$_{quart}$), 129.2 (2C, CH$_{Ar}$), 129.8 (6C, CH$_{Ar}$), 134.4 (6C, C$_{quart}$), 135.6 (2C, CH$_{Ar}$), 136.5 (12C, CH$_{Ar}$), 157.5 (2C, C$_{quart}$).

Mass (EI): m/e=684 (M$^+$)

Example 4h

Synthesis of 3-bromo-9-phenyl-6-triphenylsilylcarbazole

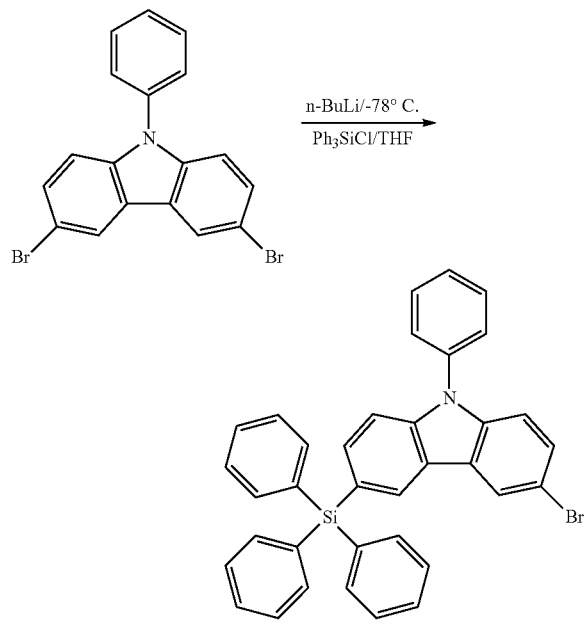

Reaction Procedure:

A solution of 9-(3-methoxyphenyl)-3,6-dibromo-9H-carbazole (26 g, 1 eq) in dry THF (700 ml) is admixed slowly at −78° C. under argon with n-butyllithium (1.6 M in hexane, 41 ml, 1 eq) and stirred at −78° C. for 2 h. After a solution of chlorotriphenylsilane (30 g, 1.5 eq) in dry THF (150 ml) had been added at −78° C., the mixture was warmed to room temperature overnight with stirring. Excess butyllithium is hydrolyzed with saturated ammonium chloride solution. The precipitated reaction product is filtered off and washed thoroughly with methylene chloride. The combined methylene chloride filtrates are extracted with water and concentrated to dryness. The residue is stirred with acetone and filtered off. Yield 74%.

$^1$H NMR (CDCl$_3$, 400 MHz):

δ=8.15 (s, 1H), 8.28 (s, 1H), 7.3-7.7 (m, 24H).

Example 4i

Synthesis of 3,6-bis(methyldiphenylsilyl)-9-phenylcarbazole

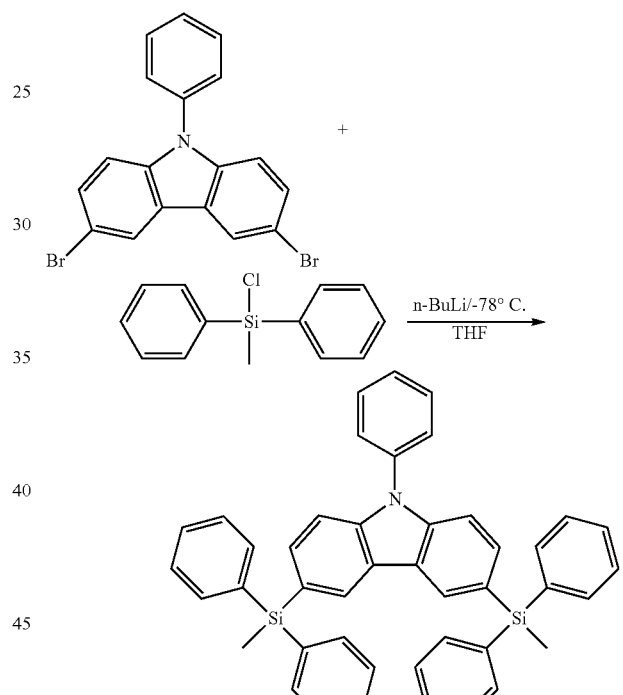

Reaction Procedure:

A solution of 9-phenyl-3,6-dibromo-9H-carbazole (3.1 g, 1 eq) in dry THF (150 ml) is admixed slowly at −78° C. under argon with n-butyllithium (1.6 M in hexane, 12.2 ml, 2.5 eq) and stirred at −78° C. for 1 h. After a solution of diphenylmethylchlorosilane (5.6 g, 3.0 eq) in dry THF (10 ml) has been added at −78° C., the mixture is warmed to room temperature overnight with stirring. Excess butyllithium is hydrolyzed with saturated ammonium chloride solution. The precipitated product is filtered off and washed thoroughly with CH$_2$Cl$_2$. Column chromatography (SiO$_2$, 15:1 cyclohexane/CH$_2$Cl$_2$) gives the product. Yield 60%.

$^1$H NMR (CDCl$_3$, 400 MHz):

δ=0.9 (s, 6H), 7.3-7.4 (m, 14H), 7.4-7.5 (m, 3H), 7.5-7.6 (m, 12H), 8.25 (s, 2H).

Example 4j

Synthesis of 3,6-bis(dimethylpentafluorophenylsilyl)-9-phenylcarbazole

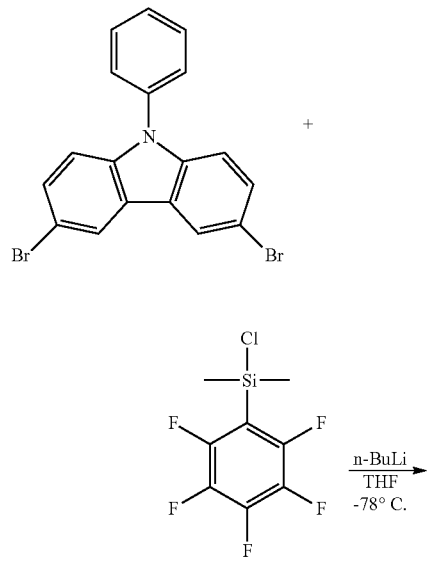

Reaction Procedure:

A solution of 9-phenyl-3,6-dibromo-9H-carbazole (3.1 g, 1 eq) in dry THF (150 ml) is admixed slowly at −78° C. under argon with n-butyllithium (1.6 M in hexane, 12.2 ml, 2.5 eq) and stirred at −78° C. for 1 h. After a solution of flophemesyl chloride (6.1 g, 3.0 eq) in dry THF (10 ml) has been added at −78° C., the mixture is warmed to room temperature overnight with stirring. Excess butyllithium is hydrolyzed with saturated ammonium chloride solution. The precipitated product is filtered off and washed thoroughly with $CH_2Cl_2$. Column chromatography (C18-$SiO_2$, MeCN) gives the product. Yield 65%.

$^1$H NMR ($CDCl_3$, 400 MHz):

δ=0.8 (s, 12H), 7.38 (d, 2H), 7.5 (m, 3H), 7.6 (m, 4H), 8.35 (s, 2H).

Example 4k

Synthesis of bis(9-phenyl-3-triphenylsilylcarbazolyl)-dimethylsilane

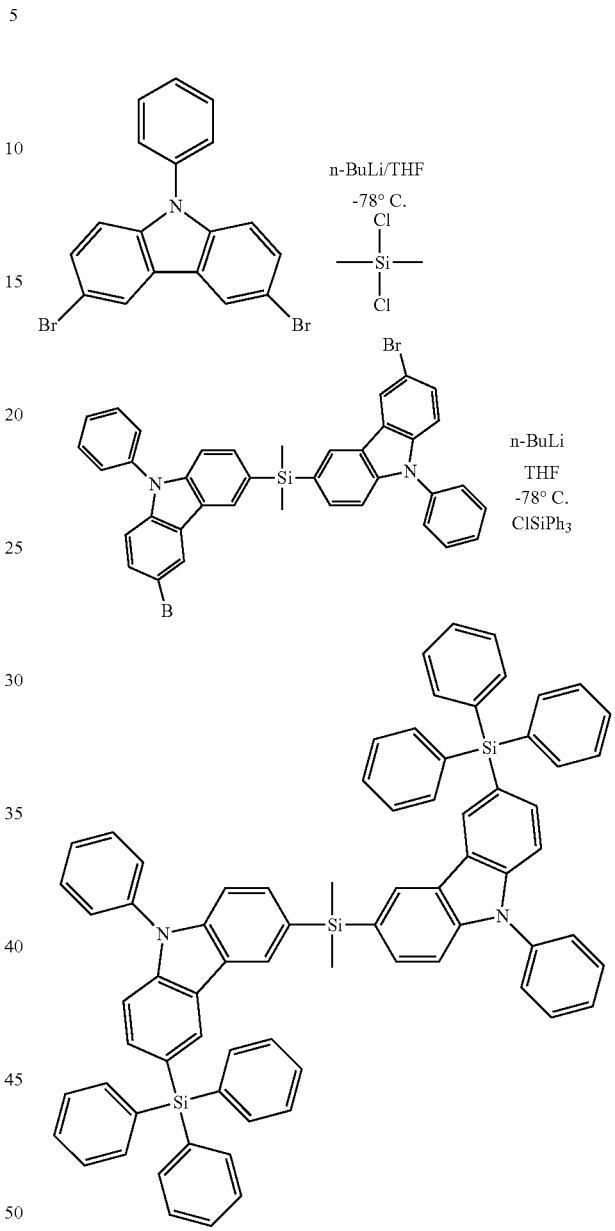

Reaction Procedure:

Step 1:

A solution of 9-phenyl-3,6-dibromo-9H-carbazole (12 g, 1 eq) in dry THF (230 ml) is admixed slowly at −78° C. under argon with n-butyllithium (1.6 M in hexane, 18.8 ml, 1 eq) and stirred at −78° C. for 1.5 h. After a solution of dichlorodimethylsilane (1.9 g, 0.5 eq) in dry THF (20 ml) has been added at −78° C., the mixture is warmed to room temperature overnight with stirring. Excess butyllithium is hydrolyzed with saturated ammonium chloride solution. The precipitated product is filtered off and washed thoroughly with $CH_2Cl_2$. Column chromatography ($SiO_2$, 10:1 hexane/EtOAc) gives the product. Yield 74%.

$^1$H NMR ($CDCl_3$, 400 MHz): δ=0.7 (s, 6H), 7.25 (dd, 4H), 7.40 (d, 2H), 7.42-7.50 (m, 6H), 7.55-7.65 (m, 6H) 8.22 (s, 2H), 8.30 (s, 2H).

Step 2:

A solution of product from step 1 (3.5 g, 1 eq) in dry THF (100 ml) is admixed slowly at −78° C. under argon with n-butyllithium (1.6 M in hexane, 7.8 ml, 2.5 eq) and stirred at −78° C. for 1.5 h. After a solution of chlorotriphenylsilane (3.6 g, 2.5 eq) in dry THF (20 ml) has been added at −78° C., the mixture is warmed to room temperature overnight with stirring. Excess butyllithium is hydrolyzed with saturated ammonium chloride solution. The precipitated product is filtered off and washed thoroughly with $CH_2Cl_2$. Boiling with acetone and filtering off gives the product. Yield: 45%.

$^1$H NMR ($CDCl_3$, 400 MHz):

δ=0.65 (s, 6H), 7.28-7.38 (m, 22H), 7.42 (t, 2H), 7.51 (m, 12H), 7.61 (d, 12H) 8.20 (s, 2H), 8.32 (s, 2H).

Example 5

Coupling of Brominated Carbazole Derivatives (X=N—H) to Silyl Compounds

Example 5a

Synthesis of 3,6-bis(triphenylsilyl)-9H-carbazole without Intermediate Isolation (Method 1)

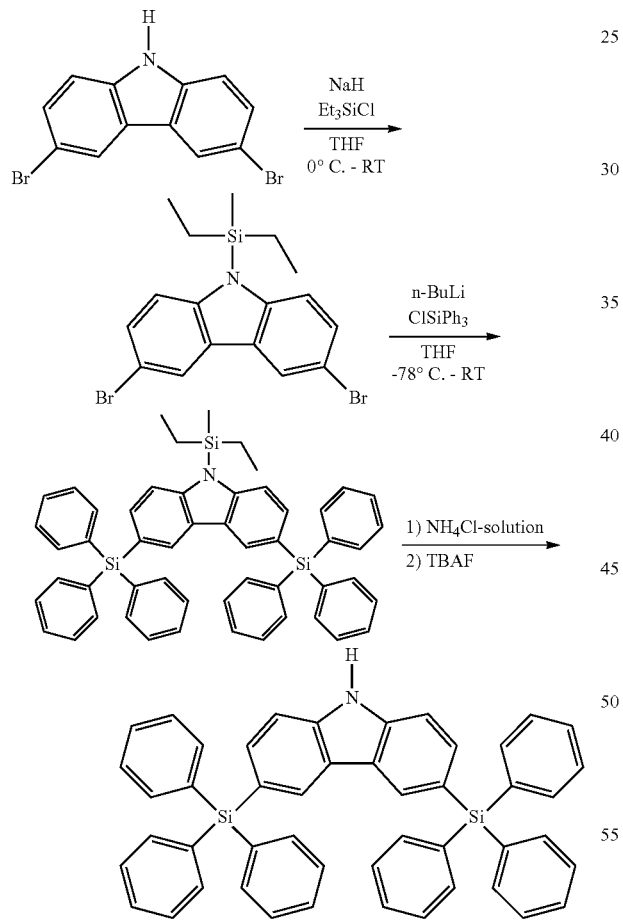

A solution of 3,6-dibromocarbazole (9.1 g, 1 eq) in dry THF (400 ml) at 0° C. under argon is admixed slowly with NaH (60% in mineral oil, 1.3 g, 1.2 eq) and stirred at 0° C. for 2 h. After adding a solution of chlorotriethylsilane (5.1 g, 1.2 eq) in dry THF (80 ml), the solution is stirred at RT (room temperature) for 1 h. The solution is cooled to −78° C. and admixed with n-butyllithium (1.6 M in hexane, 43.8 ml, 2.5 eq) and stirred at −78° C. for 1 h. After adding a solution of chlorotriphenylsilane (29.8 g, 3.5 eq) in dry THF (100 ml) at −78° C., the mixture is warmed to room temperature overnight with stirring. Excess butyllithium is hydrolyzed with saturated ammonium chloride solution. The precipitated product is filtered off and washed thoroughly with methylene chloride. The combined methylene chloride filtrates are extracted by shaking with water and dried over sodium sulfate. The organic phase is admixed with tetra-n-butylammonium fluoride (TBAF, 1 M in THF, 2 ml) and stirred at RT for 4 h. The mixture is concentrated down to 100 ml. The resulting precipitate is filtered and washed with n-hexane. Yield 66%.

$^1$H NMR ($CDCl_3$, 400 MHz): δ=7.4 (m, 20H), 7.6 (m, 14H), 8.18 (s, 2H), 8.20 (s, 1H).

Example 5b

Synthesis of 3,6-bis(triphenylsilyl)-9H-carbazole with Intermediate Isolation

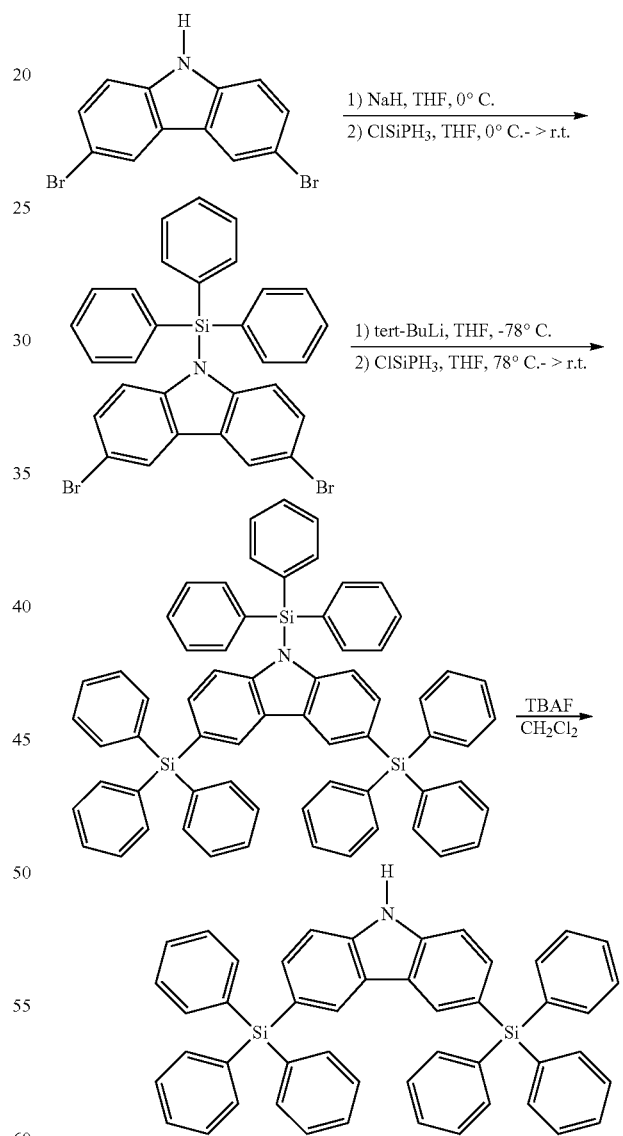

i) 3,6-Dibromo-9-triphenylsilylcarbazole

NaH (60% dispersion in oil, 1.5 g, 37 mmol) is added slowly to a cold solution (0° C.) of 3,6-dibromocarbazole (10.4 g, 31 mmol) in dry THF (1000 ml). After stirring for two hours, a solution of $ClSiPh_3$ (18.7 g, 62 mmol) in dry THF (200 ml) is added at 0° C. The mixture is stirred overnight, and saturated NH₄Cl solution is added. The resulting salt is filtered off, and the organic phase is separated from the aqueous phase. The aqueous phase is extracted with CH₂Cl₂. The organic phase is washed twice with water. The combined organic phases are dried over Na₂SO₄. Filtration through SiO₂ gives the desired product (quantitative).

ii) 3,6,9-Tris(triphenylsilyl)carbazole tert-BuLi (1.7 M in pentane, 58 ml, 99 mmol) is added slowly to a cold solution (−78° C.) of 3,6-dibromo-9-triphenylsilylcarbazole (90% purity, see i), 13 g, 22 mmol) in dry THF (1000 ml). After stirring at −78° C. for two hours, ClSiPh₃ (34 g, 115 mmol) in dry THF is added. The mixture is stirred overnight, and saturated NH₄Cl solution is added. The resulting salt is filtered off, and the organic phase is separated from the aqueous phase. The aqueous phase is extracted with CH₂Cl₂. The organic phase is washed twice with water. The combined organic phases are dried over Na₂SO₄. After column chromatography (SiO₂; 5:1 cyclohexane:CH₂Cl₂), the pure product is obtained ($R_f$~0.3, 11 g, 53%).

iii) 3,6-Bis(triphenylsilyl)-9H-carbazole

A TBAF solution (1M in THF, 4.6 ml, 4.6 mmol) is added to a solution of 3,6,9-tris-(triphenylsilyl)carbazole (8.7 g, 9.2 mmol) in CH₂Cl₂ (150 ml). After stirring for one hour, thin layer chromatography shows complete deprotection. The solvent is removed under reduced pressure, and the residue is heated under reflux in cyclohexane (150 ml). After cooling, the suspension is filtered. The residue is filtered through SiO₂ (10:1 cyclohexane:EtOAc) to obtain the desired product (7.6 g, 97%). ¹H NMR (CDCl₃, 400 MHz): δ=7.4 (m, 20H), 7.6 (m, 14H), 8.18 (s, 2H), 8.20 (s, 1H).

Example 6

N-Arylation of 3,6-silylated carbazole derivatives (X=N—H)

General Procedure:

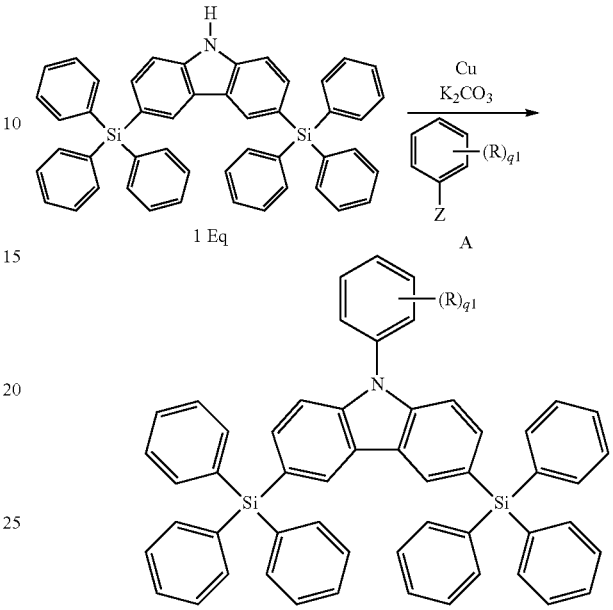

3,6-Bis(triphenylsilyl)-9H-carbazole (1 eq), phenyl halide A, potassium carbonate and copper powder are heated to 150-200° C. and stirred overnight at this temperature. After cooling to room temperature, the mixture is extracted with methylene chloride. The precipitate is filtered off and purified by column chromatography (silica gel, methylene chloride/cyclohexane).

The table which follows summarizes the data for different N-arylations of silylated carbazole derivatives which have been carried out according to the general procedure:

| A | Equiv. A | Equiv. K₂CO₃ | Mol % Cu | T (° C.) | Yield | Analysis |
|---|---|---|---|---|---|---|
| 6a (3,5-bis(CF₃)-iodobenzene) | 14.5 | 2.5 | 21 | 170 | 61 | ¹H NMR (CDCl₃, 400 MHz): δ = 7.3 (dd, 12H), 7.4 (m, 8H), 7.6 (d, 12H), 7.65 (d, 2H), 7.95 (s, 1H), 8.1 (s, 2H), 8.2 (s, 2H). |
| 6b (4-OMe-iodobenzene) | 6 | 2.5 | 21 | 160 | 71 | ¹H NMR (CDCl₃, 400 MHz): δ = 3.9 (s, 3H), 7.1 (d, 2H), 7.35 (m, 14H), 7.45 (m, 8H), 7.55 (d, 2H), 7.6 (d, 12H), 8.2 (s, 2H). |

-continued

| A | Equiv. A | Equiv. $K_2CO_3$ | Mol % Cu | T (°C.) | Yield | Analysis |
|---|---|---|---|---|---|---|
| 6c (3-iodobenzonitrile) | 4 | 2.5 | 21 | 170 | 50 | $^1$H NMR (DMF-d7, 400 MHz): δ = 7.5 (m, 18H), 7.6 (d, 12H), 7.7 (m, 4H), 8.0 (t, 1H), 8.1 (d, 1H), 8.2 (d, 1H), 8.3 (s, 2H), 8.35 (s, 1H). |
| 6d (3-iodobenzotrifluoride) | 4 | 2.5 | 21 | 155 | 80 | $^1$H NMR (CDCl$_3$, 400 MHz): δ = 7.3-7.5 (m, 20H), 7.6 (d, 14H), 7.7 (d, 2H), 7.8 (m, 1H), 7.9 (s, 1H), 8.2 (d, 2H). |
| 6e (4-iodopyridine) | 1.0 | $Cs_2CO_3$ 1.75 | 10 (CuI) | 110 In nitrobenzene with 0.2 equiv. of phenanthroline | 62 | $^1$H-NMR (CD$_2$Cl$_2$, 400 MHz): δ = 7.38 (dd, 12H), 7.43 (m, 6H), 7.58 (d, 12H), 7.65 (m, 6H), 8.2 (s, 2H), 8.8 (br, 2H). |
| 6f (5-bromopyrimidine) | 2.0 | 2.5 | 20 | 160 | 73 | $^1$H-NMR (CD$_2$Cl$_2$, 400 MHz): δ = 7.38 (m, 12H), 7.42 (m, 8H), 7.58 (d, 12H), 7.61 (d, 2H), 8.2 (s, 2H), 9.05 (s, 2H), 9.15 (s, 1H). |
| 6g | 2.0 | 2.5 | 22 | 190 | 56 | $^1$H-NMR (CDCl$_3$, 400 MHz): δ = 7.3-7.7 (m, 58H), 8.15 (s, 1H), 8.22 (s, 2H), 8.28 (s, 1H). |

-continued
| A | Equiv. A | Equiv. K₂CO₃ | Mol % Cu | T (° C.) | Yield | Analysis |
|---|---|---|---|---|---|---|
| 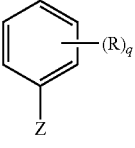<br>6h | 3.9 | 2.5 | 20 | 180 | 40 | ¹H-NMR (CDCl₃, 400 MHz): δ = 7.32 (t, 12H), 7.35-7.50 (m, 17H), 7.6 (m, 22H), 7.75 (d, 2H), 8.2 (s, 2H). |
| 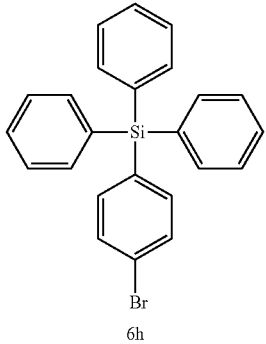<br>6i | 3.9 | 2.5 | 20 | 170 | 45 | ¹H-NMR (CDCl₃, 400 MHz): δ = 2.5 (s, 6H), 7.20 (d, 2H), 7.3-7.5 (m, 20H), 7.50-7.61 (m, 16H), 7.65 (d, 2H), 7.8 (dd, 2H), 7.9 (d, 2H), 8.2 (s, 2H). |
| 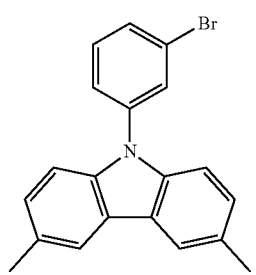<br>6j | 8.0 | 2.5 | 20 | 130 | 55 | ¹H-NMR (CDCl₃, 400 MHz): δ = 4.0 (s, 6H), 7.30-7.45 (m, 20H), 7.6 (2x d, total 14H), 8.2 (s, 2H), 8.45 (s, 2H), 8.75 (s, 1H). |
| 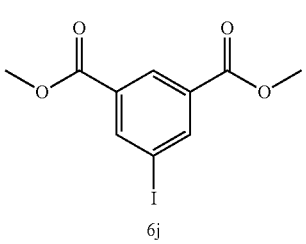<br>6k | 3.1 | 2.5 | 20 | 160 | 40 | ¹H-NMR (CDCl₃, 400 MHz): δ = 7.35 (dd, 12H), 7.42, (m, 6H), 7.50 (m, 6H), 7.58 (m, 16H), 7.72 (m, 6H), 7.88 (dd, 2H), 8.2 (s, 2H). |
| 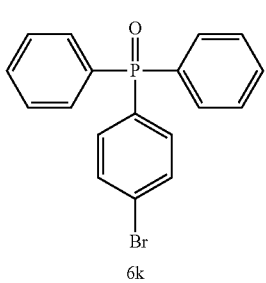<br>6l | 3.0 | 2.5 | 20 | 180 | 65 | ¹H-NMR (CDCl₃, 400 MHz): δ = 2.25 (s, 6H), 7.05 (m, 10H), 7.14, (s, 1H), 7.35 (m, 13H), 7.42 (m, 8H), 7.5 (d, 2H), 7.6 (d, 12H), 8.18 (s, 2H). |

| A | Equiv. A | Equiv. K$_2$CO$_3$ | Mol % Cu | T (° C.) | Yield | Analysis |
|---|---|---|---|---|---|---|
| 6m | 6.0 | 2.5 | 20 | 155 | 85 | $^1$H-NMR (CD$_2$Cl$_2$, 400 MHz): δ = 7.30-7.50 (m, 20H), 7.60 (m, 15H), 7.95 (br, 1H), 8.2 (s, 2H), 8.7 (br, 1H), 8.8 (br, 1H). |
| 6n | 3.5 | 2.5 | 20 | 140 | 57 | $^1$H-NMR (CDCl$_3$, 400 MHz): δ = 1.35 (t, 3H). 4.40 (q, 2H), 7.4 (m, 20H), 7.60 (m, 14H), 7.63 (t, 1H), 7.75 (d, 1H), 8.12 (d, 1H), 8.19 (s, 2H), 8.22 (s, 1H). |
| 6o | 0.5 | 1.5 | 20 | 200 | 37 | $^1$H-NMR (CDCl$_3$, 400 MHz); δ = 7.32 (dd, 24H), 7.40 (t, 12H), 7.56 (m, 28H), 7.62 (d, 2H), 7.94 (d, 4H), 8.10 (t, 1H), 8.18 (s, 4H). |
| 6p Synthesis of reactant analogous to 4g | 2 | 5 | 40 | 210 | 54 | MALDI-MS (m/z) = 1124 |
Example 7
Trisubstitution of 2,4,6-trichloro-1,3,5-triazine (cyanuric chloride) to prepare 2,4,6-tris-(3,6-bis(triphenylsilanyl)carbazol-9-yl)-1,3,5-triazine
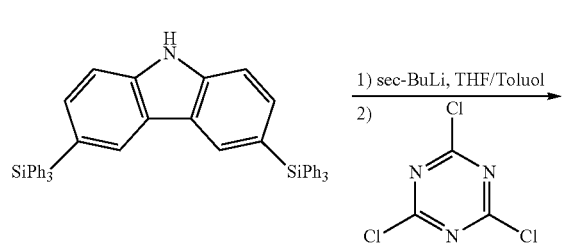
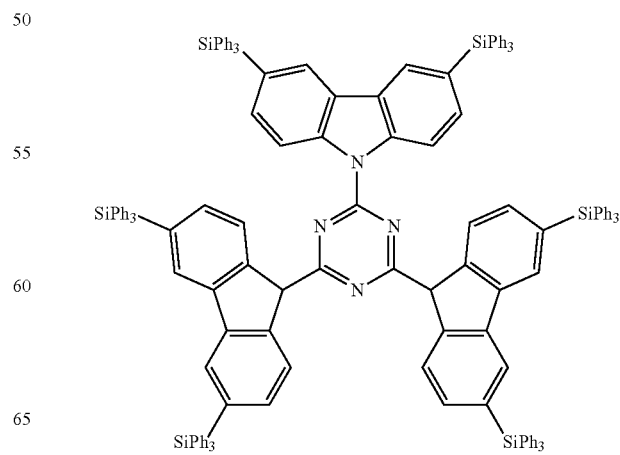

General method: 1.70 g (2.50 mmol) of 3,6-bis(triphenylsilanyl)-9H-carbazole are dissolved in 50 ml of absolute toluene under a nitrogen atmosphere in a 100 ml 2-neck flask equipped with nitrogen inlet and septum. Subsequently, the solution is admixed at room temperature with 1.92 ml (2.50 mmol) of sec-butyllithium (1.3M in cyclohexane) over a period of 10 minutes and stirred for a further 10 minutes. In a 250 ml 3-neck flask equipped with nitrogen inlet, reflux condenser and septum, 0.14 g (0.75 mmol) of cyanuric chloride is dissolved in a mixture of 10 ml of absolute THF and 20 ml of absolute toluene under a nitrogen atmosphere. The carbazole solution is added dropwise to the cyanuric chloride solution by means of a transfer canula over a period of 20 minutes. The reaction mixture is subsequently boiled under reflux for 4 hours. After cooling to room temperature, the solvent is evaporated and the residue is stirred in 200 ml of hot hexane for 10 minutes. The solid obtained by filtration is washed with diethyl ether, slurried in hot ethanol and hot-filtered. The product is purified by means of column chromatography with a hexane/toluene eluent mixture (1/4, V/V) to obtain 0.84 g (53%) of 2,4,6-tris(3,6-bis(triphenylsilanyl)carbazol-9-yl)-1,3,5-triazine as a white solid.

$^1$H NMR (250 MHz, CDCl$_3$)

δ (ppm): 8.97 (d, 6H), 8.08 (s, 6H), 7.63 (d, 6H), 7.60-7.53 (m, 30H), 7.42-7.16 (m, 60H).

MALDI-TOF: m/z=2126.53 (M$^+$)

B Use Examples

Example 1

Typical Working Method for the Production of an OLED

The ITO substrate used as the anode is first cleaned with commercial detergents for LCD production (Deconex® 20NS and 250RGAN-ACID® neutralizing agent) and then in an acetone/isopropanol mixture in a ultrasound bath. To remove possible organic residues, the substrate is exposed to a continuous ozone flow in an ozone oven for a further 25 minutes. This treatment also improves the hole injection properties of the ITO.

Thereafter, the organic materials specified below are applied by vapor deposition to the cleaned substrate at a rate of approx. 0.5-5 nm/min at approx 10$^{-8}$ mbar. The hole conductor and exciton blocker applied to the substrate is Ir(dpbic)$_3$ with a thickness of 45 nm.

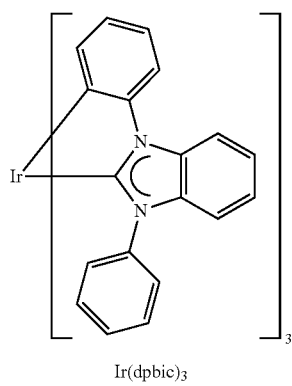

Ir(dpbic)$_3$ (for preparation see Ir complex (7) in the application WO 2005/019373).

Subsequently, a mixture of 7.5% by weight of compound V5

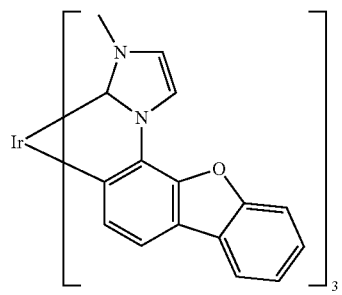

and 92.5% by weight of the compound 9-phenyl-3,6-bis(triphenylsilyl)carbazole (example 4b) is applied by vapor deposition in a thickness of 40 nm, the former compound functioning as the emitter, the latter as the matrix material.

Subsequently, the material 9-phenyl-3,6-bis(triphenylsilyl)carbazole (example 4b) is applied by vapor deposition with a thickness of 10 nm as an exciton and hole blocker.

Next, an electron transporter BCP (2,9-dimethyl-4,7-diphenyl-1,10-phenanthroline) is applied by vapor deposition in a thickness of 50 nm, as are a 0.75 nm-thick lithium fluoride layer and finally a 110 nm-thick Al electrode.

To characterize the OLED, electroluminescence spectra are recorded at different currents and voltages. In addition, the current-voltage characteristic is measured in combination with the light output emitted. The light output can be converted to photometric parameters by calibration with a photometer.

Table 1 reports the electroluminescence data (power efficiency, quantum efficiency (QE) and voltage) for different inventive OLEDs. The construction of the particular OLED is specified in the right-hand column of table 1 (device structure). The particular OLED is produced according to the typical working method specified above. The values for power efficiency, quantum efficiency (QE) and voltage reported in table 1 are relative values, based in each case on a reference OLED which is identical in terms of structure to the particular OLED and differs from the particular inventive OLED in that 9-phenyl-3,6-bis(triphenylsilyl)carbazole (example 4b) is used both as a matrix and as an exciton and hole blocker. The values for the power efficiency, quantum efficiency (QE) and voltage reported in table 1 are defined as 100% for the particular reference OLED. A comparison of a diode in which 9-phenyl-3,6-bis(triphenylsilyl)carbazole (example 4b) is used both as the matrix and as an exciton and hole blocker with a diode having an identical structure in which, instead of 9-phenyl-3,6-bis(triphenylsilyl)carbazole (example 4b), (the synthetically significantly more difficult to obtain) 9-(4-tert-butylphenyl)-3,6-bis(triphenylsilyl)carbazole is used shows that the electroluminescence data of the two OLEDs differ from one another only insignificantly. The OLED used in each case as the reference OLED, which comprises 9-phenyl-3,6-bis(triphenylsilyl)carbazole (example 4b) both as the matrix and as an exciton and hole blocker thus also serves as the reference for an OLED which comprises 9-(4-tert-butylphenyl)-3,6-bis(triphenylsilyl)carbazole both as the matrix and as an exciton and hole blocker.

As Originally Filed

| Material | Structure | Function | (Power efficiency (max/power efficiency (max, stardard)) 100% | QE (max)/ QE (max, standard) 100% | Voltage at 300 nits/ voltage at 300 nits (standard) 100% | Device structure (ITO 125 +/− 20 nm (analogous to typical working method, exchange of 4b for novel material) |
|---|---|---|---|---|---|---|
| 4b (standard) | 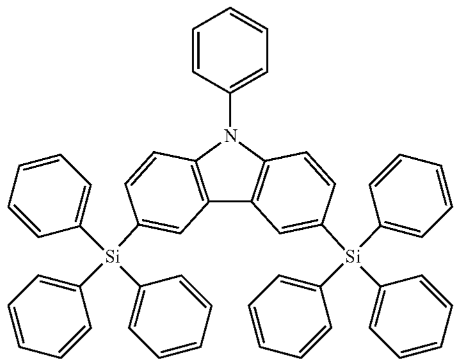 [SMILES: c1ccc(-n2c3ccc([Si](c4ccccc4)(c4ccccc4)c4ccccc4)cc3c3cc([Si](c4ccccc4)(c4ccccc4)c4ccccc4)ccc32)cc1] | matrix + blocker | 100 | 100 | 100 | See working method specified above |
| 6a | 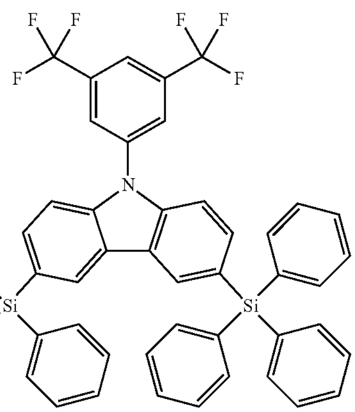 | blocker | 121 | 123 | 99 | V1 (45 nm)//8.5% V5: 4b (40 nm)//6a (10 nm)//BCP (50 nm)//LiF//Alu |
| | | matrix | 106 | 100 | 103 | V1 (45 nm)//8.5% V5: 6a (40 nm)//4b (10 nm)//BCP (50 nm)//LiF//Alu |
| | | matrix + blocker | 111 | 100 | 93 | V1 (45 nm)//8.5% V5: 6a (40 nm)//6a (10 nm)//BCP (50 nm)//LiF//Alu |
| 6b | 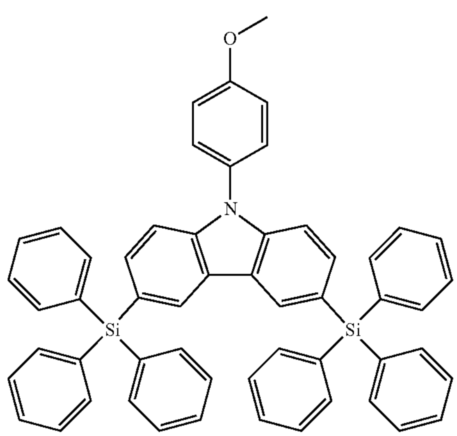 [SMILES: COc1ccc(-n2c3ccc([Si](c4ccccc4)(c4ccccc4)c4ccccc4)cc3c3cc([Si](c4ccccc4)(c4ccccc4)c4ccccc4)ccc32)cc1] | blocker | 99 | 98 | 100 | V1 (45 nm)//8.5% V5: 4b (40 nm)//6b (10 nm)//BCP (50 nm)//LiF//Alu |
| | | matrix | 109 | 108 | 95 | V1 (45 nm)//8.5% V5: 6b (40 nm)//4b (10 nm)//BCP (50 nm)//LiF//Alu |
| | | matrix + blocker | 106 | 106 | 98 | V1 (45 nm)//8.5% V5: 6b (40 nm)//6b (10 nm)//BCP (50 nm)//LiF//Alu |

-continued

| Material | Structure | Function | (Power efficiency (max/power efficiency (max, stardard)) 100% | QE (max)/ QE (max, standard) 100% | Voltage at 300 nits/ voltage at 300 nits (standard) 100% | Device structure (ITO 125 +/- 20 nm (analogous to typical working method, exchange of 4b for novel material) |
|---|---|---|---|---|---|---|
| 6c | 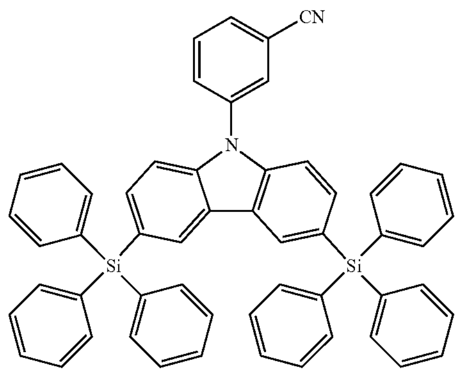 [SMILES: N#Cc1cccc(-n2c3ccc([Si](c4ccccc4)(c4ccccc4)c4ccccc4)cc3c3cc([Si](c4ccccc4)(c4ccccc4)c4ccccc4)ccc32)c1] | matrix + blocker | no comparable reference values available | no comparable reference values available | 75 | V1 (40 nm)//7.5% V5: 6c (40 nm)//6c (5 nm)//BCP (50 nm)//LiF//Alu |
| 6d | 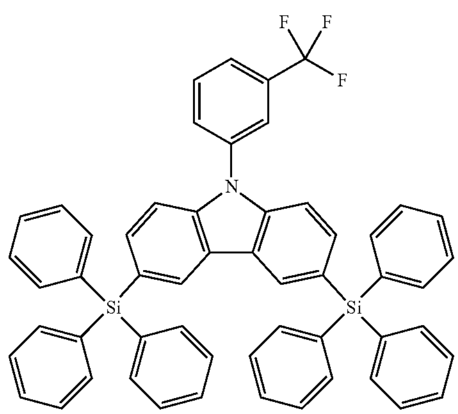 [SMILES: FC(F)(F)c1cccc(-n2c3ccc([Si](c4ccccc4)(c4ccccc4)c4ccccc4)cc3c3cc([Si](c4ccccc4)(c4ccccc4)c4ccccc4)ccc32)c1] | matrix + blocker | no comparable reference values available | no comparable reference values available | 87 | V1 (40 nm)//7.5% V5: 6d (40 nm)//6d (5 nm)//BCP (50 nm)//LiF//Alu |
| 6e | 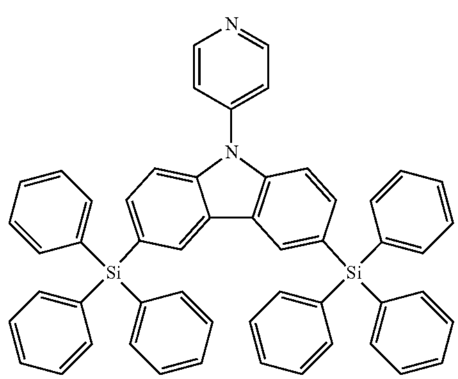 [SMILES: c1ccc([Si](c2ccccc2)(c2ccccc2)c2ccc3c(c2)c2cc([Si](c4ccccc4)(c4ccccc4)c4ccccc4)ccc2n3-c2ccncc2)cc1] | blocker | 124 | 130 | 94 | 10% MoO$_3$: V1 (35 nm)// V1(10 nm)//7.5% V5: 4b (40 nm)//6e (10 nm)//BCP (50 nm)//LiF//Alu |
| | | matrix | 118 | 109 | 84 | 10% MoO$_3$: V1 (35 nm)// V1(10 nm)//7.5% V5: 6e (40 nm)//4b (10 nm)// BCP (50 nm)//LiF//Alu |
| | | matrix + blocker | 144 | 139 | 78 | 10% MoO$_3$: V1 (35 nm)// V1(10 nm)//7.5% V5: 6e (40 nm)//6e (10 nm)// BCP (50 nm)//LiF//Alu |

| Material | Structure | Function | (Power efficiency (max/power efficiency (max, standard)) 100% | QE (max)/ QE (max, standard) 100% | Voltage at 300 nits/ voltage at 300 nits (standard) 100% | Device structure (ITO 125 +/− 20 nm (analogous to typical working method, exchange of 4b for novel material) |
|---|---|---|---|---|---|---|
| 6f | 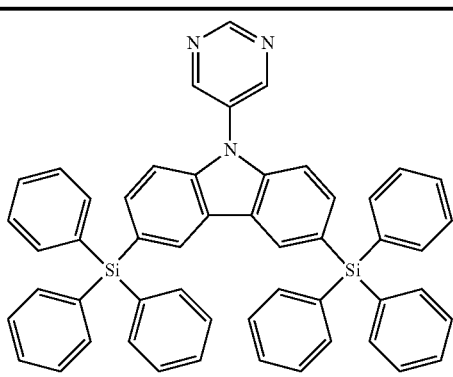 | blocker | 158 | 177 | 92 | V1 (45 nm)//7.5% V5: V1 (10 nm)//7.5% V5: 4b (40 nm)//6f (10 nm)//BCP (40 nm)//LiF//Alu |
| | | matrix | 125 | 117 | 74 | V1 (45 nm)//8.5% V5: V1 (10 nm)//8.5% V5: 6f (40 nm)//4b (10 nm)// BCP (40 nm)//LiF//Alu |
| | | matrix + blocker | 138 | 137 | 65 | V1 (45 nm)//8.5% V5: V1 (10 nm)//8.5% V5: 6f (40 nm)//6f (10 nm)// BCP (40 nm)//LiF//Alu |
| 6m | 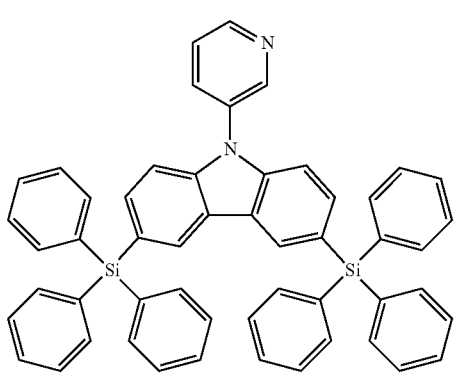 [SMILES: c1ccc([Si](c2ccccc2)(c2ccccc2)c2ccc3c(c2)c2cc([Si](c4ccccc4)(c4ccccc4)c4ccccc4)ccc2n3-c2cccnc2)cc1] | blocker | 113 | 113 | 86 | NPD (45 nm)//8.5% V5: 4b (40 nm)//6m (10 nm)// BCP (40 nm)//LiF//Alu |
| | | matrix | 126 | 124 | 87 | NPD (45 nm)//8.5% V5: 6m (40 nm)//4b (10 nm)// BCP (40 nm)//LiF//Alu |
| | | matrix + blocker | 151 | 149 | 94 | NPD (45 nm)//8.5% V5: 6m (40 nm)//6m (10 nm)// BCP (40 nm)//LiF//Alu |
| | | matrix + blocker | 130 | 135 | 78 | V1 (45 nm)//8.5% V5: V1 (10 nm)//8.5% V5: 6m (40 nm)//6m (10 nm)// BCP (40 nm)//LiF//Alu |

Example 2

The OLEDs specified below in table 2 are produced according to the typical working method specified in example 1. The table which follows reports the electroluminescence data (power efficiency, quantum efficiency (QE) and voltage) for various inventive OLEDs. In the OLEDs specified below, instead of the material 9-phenyl-3,6-bis(triphenylsilyl)carbazole (example 4b) according to the typical working method of example 1, another compound of the formula II was used in each case as the matrix material and/or blocker material. Otherwise, the OLEDs specified below do not differ from the OLED described above.

TABLE 2

| Material | | Function | Power efficiency (max) (cd/A) | QE (max) (%) | V at 300 nits (V) | Device structure (ITO 125 +/−20 nm) (analagous to typical working method, exchange of 4b for novel material) |
|---|---|---|---|---|---|---|
| 4a | 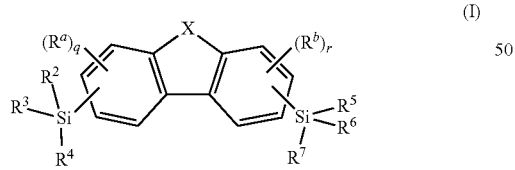 | matrix + blocker | 10.8 | 7.2 | 8.7 | V1 (45 nm)//8.5% V5: 4a (40 nm)//4a (10 nm)//TPBI (50 nm)//LiF//Alu |
| 4g | 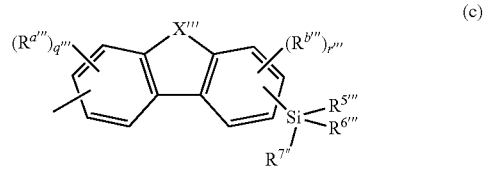 | blocker | 7.9 | 7.0 | 9.7 | 10% MoO$_3$: V1 (35 nm)//V1 (10 nm)//7.5% V5: 4b (40 nm)//4g (10 nm)//BCP (40 nm)//LiF//Alu |
| | | matrix | 8.4 | 7.1 | 8.9 | 10% MoO$_3$: V1 (35 nm)//V1 (10 nm)//7.5% V5: 4g (40 nm)//4b (10 nm)//BCP (40 nm)//LiF//Alu |
| | | matrix + blocker | 9.7 | 8.2 | 8.1 | 10% MoO$_3$: V1 (35 nm)//V1 (10 nm)//7.5% V5: 4g (40 nm)//4g (10 nm)//BCP (40 nm)//LiF//Alu |

The invention claimed is:

1. An organic light-emitting diode comprising an anode and a cathode Ka and a light-emitting layer E and optionally at least one further layer, selected from the group consisting of: at least one blocking layer for electrons/excitons, at least one blocking layer for holes/excitons, at least one hole injection layer, at least one hole conductor layer, at least one electron injection layer and at least one electron conductor layer, wherein the organic light-emitting diode comprises at least one hole/exicton blocker layer, the compound of the general formula (I) is present exclusively in the light-emitting layer and in the hole/exciton blocker layer, $$(I)$$
$(R^a)_q$ — [structure with X] — $(R^b)_r$
$R^2$
$R^3$—Si
$R^4$
$R^5$
Si—$R^6$
$R^7$ in which:

X is NR$^1$ or O

R$^1$ is substituted C6-C30-aryl, or substituted or unsubstituted heteroaryl having from 5 to 30 ring atoms, wherein R$^1$ radical comprises N, O or F;

R$^2$, R$^3$, R$^4$, R$^5$, R$^6$, R$^7$ are each independently substituted or unsubstituted C$_1$-C$_{20}$-alkyl, or substituted or unsubstituted C$_6$-C$_{30}$-aryl, or a structure of the general formula (c)

$$(c)$$
$(R^{a'''})_{q'''}$ — [structure with X'''] — $(R^{b'''})_{r'''}$
Si—$R^{5'''}$
$R^{6'''}$
$R^{7'''}$ R$^a$, R$^b$ are each independently substituted or unsubstituted C$_1$-C$_{20}$-alkyl, substituted or unsubstituted C$_6$-C$_{30}$-aryl, or substituted or unsubstituted heteroaryl having from 5 to 30 ring atoms or a substituent with donor or acceptor action selected from the group consisting of: C$_1$-C$_{20}$-alkoxy, C$_6$-C$_{30}$-aryloxy, C$_1$-C$_{20}$-alkylthio, C$_6$-C$_{30}$-arylthio, SiR$^{14}$R$^{15}$R$^{16}$, halogen radicals, halogenated C$_1$-C$_{20}$-alkyl radicals, carbonyl (—CO (R$^{14}$)), carbonylthio (—C=O(SR$^{14}$)), carbonyloxy (—C=O(OR$^{14}$)), oxycarbonyl (—OC=O(R$^{14}$)), thiocarbonyl (—SC=O(R$^{14}$)), amino (—NR$^{14}$R$^{15}$), OH, pseudohalogen radicals, amido (—C=O (NR$^{14}$)), —NR$^{14}$C=O(R$^{15}$), phosphonate (—P(O) (OR$^{14}$)$_2$, phosphate (—OP(O)(OR$^{14}$)$_2$), phosphine (—PR$^{14}$R$^{15}$), phosphine oxide (—P(O)R$^{14}$$_2$), sulfate (—OS(O)$_2$OR$^{14}$), sulfoxide (—S(O)R$^{14}$), sulfonate (—S(O)$_2$OR$^{14}$), sulfonyl (—S(O)$_2$R$^{14}$), sulfonamide (—S(O)$_2$NR$^{14}$R$^{15}$), NO$_2$, boronic esters (—OB (OR$^{14}$)$_2$), imino (—C=NR$^{14}$R$^{15}$)), borane radicals, stannane radicals, hydrazine radicals, hydrazone radicals, oxime radicals, nitroso groups, diazo groups, vinyl groups, sulfoximines, alanes, germanes, boroximes and borazines;

$R^{14}$, $R^{15}$, $R^{16}$
are each independently substituted or unsubstituted C1-C20-alkyl, or substituted or unsubstituted C6-C30-aryl; and q,r are each independently 0, 1, 2 or 3; where, in the case when q or r is 0, all substitutable positions of the aryl radical are substituted by hydrogen, where the radicals and indices $X'''$, $R^{5'''}$, $R^{6'''}$, $R^{7'''}$, $R^{a'''}$, $R^{b'''}$, q''' and r''' in formula (c) are each independently as defined for the radicals and indices X, $R^5$, $R^6$, $R^7$, $R^a$, $R^b$, q and r of the compounds of formula (I).

2. The organic light-emitting diode according to claim 1, wherein at least one of the $R^2$, $R^3$ and $R^4$ radicals and/or at least one of the $R^5$, $R^6$ and $R^7$ radicals is substituted or unsubstituted $C_6$-$C_{30}$-aryl.

3. The organic light-emitting diode according to claim 1, wherein the compound of the general formula (I) is a 3,6-disilyl-substituted compound of the general formula (Ia):

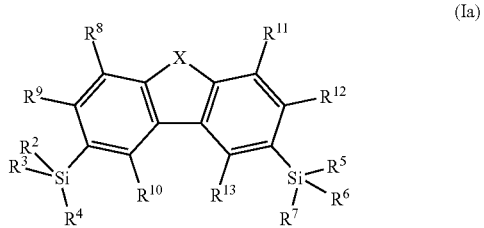

(Ia)

in which:
X is $NR^1$ or O;
$R^1$ is substituted $C_6$-$C_{30}$-aryl, or substituted or unsubstituted heteroaryl having from 5 to 30 ring atoms, wherein $R^1$ comprises N, O or F;
$R^2$, $R^3$, $R^4$, $R^5$, $R^6$, R7
are each independently substituted or unsubstituted $C_1$-$C_{20}$-alkyl or substituted or unsubstituted $C_6$-$C_{30}$-aryl or a structure of the general formula (c); and
$R^8$, $R^9$, $R^{10}$, $R^{11}$, $R^{12}$, $R^{13}$
are each independently hydrogen or are each independently substituted or unsubstituted $C_1$-$C_{20}$-alkyl, substituted or unsubstituted $C_6$-$C_{30}$-aryl, substituted or unsubstituted heteroaryl having from 5 to 30 ring atoms or a substituent with donor or acceptor action; or $SiR^{14}R^{15}R^{16}$; where $R^{14}$, $R^{15}$ and $R^{16}$ are each independently substituted or unsubstituted $C_1$-$C_{20}$-alkyl or substituted or unsubstituted phenyl.

4. The organic light-emitting diode according to claim 3, wherein:
X is $NR^1$;
$R^1$ is substituted $C_6$-$C_{30}$-aryl, wherein $R^1$ comprises N, O or F;
$R^2$, $R^3$, $R^4$, $R^5$, $R^6$, $R^7$
are each independently substituted or unsubstituted $C_1$-$C_{20}$-alkyl or substituted or unsubstituted $C_6$-$C_{30}$-aryl, or a structure of the general formula (c) where at least one of the $R^2$, $R^3$ and $R^4$ radicals and/or at least one of the $R^5$, $R^6$ and $R^7$ radicals is substituted or unsubstituted $C_6$-$C_{30}$-aryl;
$R^8$, $R^9$, $R^{10}$, $R^{11}$, $R^{12}$, $R^{13}$
are each independently hydrogen or are each independently substituted or unsubstituted $C_1$-$C_{20}$-alkyl, substituted or unsubstituted $C_6$-$C_{30}$-aryl, substituted or unsubstituted heteroaryl having from 5 to 30 ring atoms or a substituent with donor or acceptor action; or $SiR^{14}R^{15}R^{16}$; and
$R^{14}$, $R^{15}$, $R^{16}$
are each independently substituted or unsubstituted $C_1$-$C_{20}$-alkyl or substituted or unsubstituted $C_6$-$C_{30}$-aryl.

5. The organic light-emitting diode according to claim 1, wherein the $R^1$ radical is substituted $C_6$-aryl of the following formula:

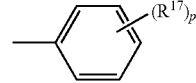

in which
p is 1, 2, 3, 4 or 5; and
$R^{17}$ is $C_1$-$C_6$ alkoxy, CN, $CF_3$ or F.

6. A method of making the organic light-emitting diode according to claim 1, comprising providing the compound of general formula (I) wherein the organic light-emitting diode comprises at least one hole/exciton blocker layer such that the compound of the general formula (I) is provided exclusively to the light-emitting layer and the hole/exciton blocker layer.

7. A device selected from the group consisting of a stationary visual display unit, a mobile visual display unit and an illumination unit comprising at least one organic light-emitting diode according to claim 1.

* * * * *